(12) United States Patent
Berger et al.

(10) Patent No.: US 8,030,340 B2
(45) Date of Patent: Oct. 4, 2011

(54) INDAZOLYL SULPHONAMIDE DERIVATIVES USEFUL AS GLUCOCORTICOID MODULATORS

(75) Inventors: Markus Berger, Berlin (DE); Lena Bergstrom, Lund (SE); Jan Dahmen, Lund (SE); Anders Eriksson, Lund (SE); Balint Gabos, Lund (SE); Martin Hemmerling, Lund (SE); Krister Henriksson, Lund (SE); Svetlana Ivanova, Lund (SE); Matti Lepisto, Lund (SE); Stinabritt Nilsson, Lund (SE); Camilla Taflin, Lund (SE); Hartmut Rehwinkel, Berlin (DE); Darren McKerrecher, Alderley (GB)

(73) Assignees: AstraZeneca AB, Sodertalje (SE); Bayer Schering Pharma Aktiengesellschaft, Berlin (DE)

( * ) Notice: Subject to any disclaimer, the term of this patent is extended or adjusted under 35 U.S.C. 154(b) by 349 days.

(21) Appl. No.: 11/986,555

(22) Filed: Nov. 21, 2007

(65) Prior Publication Data

US 2008/0207721 A1    Aug. 28, 2008

(30) Foreign Application Priority Data

Nov. 23, 2006 (SE) .................................... 0602501

(51) Int. Cl.
*A01N 43/56* (2006.01)

(52) U.S. Cl. .................... 514/403; 548/361.1; 548/361.5
(58) Field of Classification Search .................. 514/403; 548/361.1, 361.5
See application file for complete search history.

(56) References Cited

U.S. PATENT DOCUMENTS

| | | | |
|---|---|---|---|
| 3,992,441 A | 11/1976 | Helland | |
| 4,443,477 A | 4/1984 | Witte et al. | |
| 4,948,809 A | 8/1990 | Witte et al. | |
| 5,861,401 A | 1/1999 | Bradbury | |
| 6,323,199 B1 | 11/2001 | Lehmann et al. | |
| 7,297,709 B2 * | 11/2007 | Dai et al. | 514/406 |
| 2004/0235892 A1 * | 11/2004 | Dai et al. | 514/314 |
| 2007/0265326 A1 | 11/2007 | Biggadike et al. | |
| 2008/0207721 A1 | 8/2008 | Berger et al. | |
| 2008/0214641 A1 | 9/2008 | Berger et al. | |
| 2009/0093485 A1 | 4/2009 | Bladh et al. | |
| 2009/0124607 A1 | 5/2009 | Bladh et al. | |
| 2009/0170898 A1 | 7/2009 | Bengtsson et al. | |

FOREIGN PATENT DOCUMENTS

| | | |
|---|---|---|
| EP | 0031954 | 7/1981 |
| EP | 0201735 | 11/1986 |
| EP | 0261539 | 3/1988 |
| EP | 0558258 | 9/1993 |
| EP | 0569193 | 11/1993 |
| EP | 0610896 | 8/1994 |
| EP | 0679641 | 11/1995 |
| EP | 0947500 | 10/1999 |
| EP | 0976722 | 2/2000 |
| EP | 1190710 | 3/2002 |
| EP | 1447401 | 8/2004 |
| GB | 0607840.6 | 4/2006 |
| WO | WO95/02580 | 1/1995 |
| WO | WO95/03279 | 2/1995 |
| WO | WO95/33461 | 12/1995 |
| WO | WO96/06822 | 3/1996 |
| WO | WO96/36595 | 11/1996 |
| WO | WO99/33786 | 7/1999 |
| WO | WO99/38845 | 8/1999 |
| WO | WO01/24786 | 4/2001 |
| WO | WO01/46172 | 6/2001 |
| WO | WO02/20474 | 3/2002 |
| WO | WO02/28820 | 4/2002 |
| WO | WO03/028641 | 4/2003 |
| WO | WO03/076401 | 9/2003 |
| WO | WO03/086294 | 11/2003 |
| WO | WO03/099773 | 12/2003 |
| WO | WO2004/018414 | 3/2004 |
| WO | WO2004/019935 | 3/2004 |
| WO | WO2004/050631 | 6/2004 |
| WO | WO2004/073634 | 9/2004 |
| WO | WO2004/089913 | 10/2004 |
| WO | WO2004/110418 | 12/2004 |
| WO | WO2005/004810 | 1/2005 |
| WO | WO2005/060963 | 7/2005 |
| WO | WO2005/077895 | 8/2005 |

(Continued)

OTHER PUBLICATIONS

Bradbury et al., "New Non-Peptide Endothelin-A Receptor Antagonists: Synthesis, Biological Properties, and Structure-Activity Relationships of 5-(Dimethylamino)-*N*-pyridyl-, -*N*-pyrimidinyl-*N*-pyridazinyl-, and -*N*-pyrazinyl-1-naphthalenesulfonamides", *J. Med. Chem.* 40:996-1004 (1997).

(Continued)

*Primary Examiner* — Andrew D Kosar
*Assistant Examiner* — Valerie Rodriguez-Garcia
(74) *Attorney, Agent, or Firm* — Fish & Richardson P.C.

(57) ABSTRACT

Compounds of formula (I):

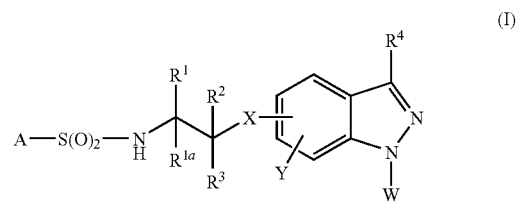

or a pharmaceutically acceptable salt thereof, compositions comprising them, processes for preparing them and their use in medical therapy (for example modulating the glucocorticoid receptor in a warm blooded animal).

12 Claims, No Drawings

FOREIGN PATENT DOCUMENTS

| | | |
|---|---|---|
| WO | WO2005/086904 | 9/2005 |
| WO | WO2005/123688 | 12/2005 |
| WO | WO2006/046914 | 5/2006 |
| WO | WO2006/046916 | 5/2006 |
| WO | WO2006/135826 | 12/2006 |
| WO | WO2006/138373 | 12/2006 |
| WO | WO 2007/046747 A1 * | 4/2007 |
| WO | WO2007/054294 | 5/2007 |
| WO | WO2007/114763 | 10/2007 |
| WO | WO2007/122165 | 11/2007 |
| WO | WO2008/008882 | 1/2008 |
| WO | WO2008/043788 | 4/2008 |
| WO | WO2008/043789 | 4/2008 |
| WO | WO2008/051532 | 5/2008 |
| WO | WO2008/057856 | 5/2008 |
| WO | WO2008/057857 | 5/2008 |
| WO | WO2008/063116 | 5/2008 |
| WO | WO2008/070507 | 6/2008 |
| WO | WO2008/076048 | 6/2008 |
| WO | WO2008/079073 | 7/2008 |
| WO | WO2008/124665 | 10/2008 |
| WO | WO2008/124745 | 10/2008 |
| WO | WO2008/135578 | 11/2008 |
| WO | WO2009/050218 | 4/2009 |
| WO | WO2009/050220 | 4/2009 |
| WO | WO2009/050221 | 4/2009 |
| WO | WO2009/050243 | 4/2009 |
| WO | WO2009/050244 | 4/2009 |
| WO | WO2009/062950 | 5/2009 |
| WO | WO2009/074590 | 6/2009 |
| WO | WO2009/108525 | 9/2009 |
| WO | WO2009/111214 | 9/2009 |

OTHER PUBLICATIONS

Fabiana et al., "Mode of Action of Sulfanilyl Fluoroquinolones", *Antimicrobial Agents and Chemotherapy* 42:1495-1498 (1998).

Gaedcke et al., "Structure dependence of antiplasmodic activity of 3-IN-(4'-amidosulphonylphenypamin~methyl] quinoline", *Arch. Pharm* (Weinheim) 313:166-173 (1930).

Jansen et al., "Hydantoin-Substituted 4,6-Dichloroindole-2-carboxylic Acids as Ligands with High Affinity for the Glycine Building Site of the NMDA Receptor", *J. Med. Chem.* 46:64-73 (2003).

STN International file Registry: RN 321722-44-5, RN 321704-10-3, RN 321704-02-3, RN 321703-82-6, RN 321703-77-9, RN 321703-75-7.

STN International file Registry: RN 674768-65-1, RN 343372-84-9, RN 343372-70-3, RN 339016-98-7, RN 519018-69-0, RN 261623-54-5.

Clark et al., "1*H*-Pyrazolo[3,4-g]hexahydro-isoquinolines as selective glucocorticoid receptor antagonists with high functional activity", *Bioorg. Med. Chem. Lett.* 18:1312-1317 (2008).

Mohler et al., "Dissociated non-steroidal glucocorticoids: tuning out untoward effects", *Expert Opin. Ther. Patents* 17:37-58 (2007).

Mohler et al., "Non-steroidal glucocorticoid receptor antagonists: the race to replace RU-486 for anti- glucocorticoid therapy", *Expert Opin. Ther. Patents* 17:59-81 (2007).

Schäcke et al., "Dissociated non-steroidal glucocorticoid receptor modulators: an update on new compounds", *Expert Opin. Ther. Patents* 18:339-352 (2008).

USPTO Notice of Allowance in U.S. Appl. No. 12/005,066, mailed Mar. 24, 2009, 10 pages.

Fish & Richardson P.C., Request for Continued Examination in U.S. Appl. No. 12/005,066, filed Jun. 19, 2009, 6 pages.

USPTO Notice of Allowance in U.S. Appl. No. 12/005,066, mailed Sep. 9, 2009, 6 pages.

Fish & Richardson P.C., Request for Continued Examination in U.S. Appl. No. 12/005,066, filed Nov. 10, 2009, 5 pages.

USPTO Notice of Allowance in U.S. Appl. No. 12/005,066, mailed Jan. 13, 2010, 8 pages.

* cited by examiner

INDAZOLYL SULPHONAMIDE DERIVATIVES USEFUL AS GLUCOCORTICOID MODULATORS

The present invention relates to novel indazolyl sulphonamide derivatives, to pharmaceutical compositions comprising such derivatives, to processes for preparing such novel derivatives and to the use of such derivatives as medicaments (for example in the treatment of an inflammatory disease state).

Sulphonamide derivatives are disclosed as anti-inflammatories in WO 2004/019935 and WO 2004/050631. Pharmaceutically active sulphonamides are also disclosed in Arch. Pharm. (1980) 313 166-173, J. Med. Chem. (2003) 46 64-73, J. Med. Chem (1997) 40 996-1004, EP 0031954, EP 1190710 (WO 200124786), U.S. Pat. No. 5,861,401, U.S. Pat. No. 4,948,809, U.S. Pat. No. 3,992,441 and WO 99/33786.

It is known that certain non-steroidal compounds interact with the glucocorticoid receptor (GR) and, as a result of this interaction, produce a suppression of inflammation (see, for example, U.S. Pat. No. 6,323,199). Such compounds can show a clear dissociation between anti-inflammatory and metabolic actions making them superior to earlier reported steroidal and non-steroidal glucocorticoids. The present invention provides further non-steroidal compounds as modulators (for example agonists, antagonists, partial agonists or partial antagonists) of the glucocorticoid receptor.

The present invention provides a compound of formula (I):

(I)

$$A-S(O)_2-\underset{H}{N}-\underset{R^{1a}}{\overset{R^1}{C}}-\underset{R^3}{\overset{R^2}{C}}-X-\text{[indazolyl with } R^4, Y, W\text{]}$$

wherein:

A is $C_{1-10}$alkyl, $C_{5-10}$aryl, $C_{5-10}$aryl$C_{1-6}$alkyl, $C_{5-10}$heteroaryl, $C_{5-10}$heteroaryl$C_{1-6}$alkyl, $C_{5-10}$aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)OC$_{1-6}$alkyl, $C_{5-10}$aryloxy$C_{1-10}$alkyl or NR$^5$R$^6$C$_{0-6}$alkyl whereby the aryl is optionally substituted with one or more substituents selected from B;

R$^1$ and R$^{1a}$ are independently selected from hydrogen, $C_{1-4}$alkyl, $C_{1-4}$haloalkyl, $C_{1-4}$hydroxyalkyl and $C_{1-4}$alkylOC$_{1-4}$alkyl;

R$^2$ is hydrogen or $C_{1-4}$alkyl;

R$^3$ is $C_{3-7}$ cycloalkyl (optionally substituted by halogen or $C_{1-6}$ alkyl), $C_{5-10}$aryl$C_{0-3}$alkyl, $C_{5-10}$arylOC$_{0-3}$alkyl, $C_{5-10}$heteroaryl$C_{0-3}$alkyl, $C_{1-6}$alkyl, $C_{1-6}$alkenyl or $C_{1-6}$alkynyl which are optionally substituted by one or more B;

B is $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-3}$alkylS(O)$_n$$C_{0-4}$alkyl, $C_{1-6}$haloalkyl, $C_{1-4}$haloalkoxy, halogen, nitro, cyano, $C_{1-4}$alkylOC$_{1-6}$alkyl, $C_{0-6}$alkylOC$_{1-4}$alkyl OC$_{0-4}$alkyl, $C_{0-6}$alkylC(O)C$_{0-6}$alkyl, $C_{0-4}$alkylC(O) OC$_{0-4}$alkyl, $C_{0-4}$alkylOC(O)C$_{0-4}$alkyl, NR$^5$R$^6$C$_{0-4}$alkyl, NR$^5$R$^6$C(O)C$_{0-4}$alkyl, NR$^5$R$^6$OC(O)C$_{0-4}$alkyl, NR$^5$R$^6$C(O) OC$_{0-4}$alkyl, R$^6$C(O)R$^5$NC$_{0-4}$alkyl, $C_{0-4}$alkylOC(O)C$_{0-4}$alkylNH, $C_{0-4}$alkylC(O)OC$_{0-4}$alkylNH, $C_{0-4}$alkylC(O)C$_{0-4}$alkylNH or NR$^5$R$^6$S(O)$_n$$C_{0-4}$alkyl;

R$^4$ is hydrogen, hydroxy, halogen, $C_{1-4}$ alkyl or $C_{1-4}$ haloalkyl;

W is hydrogen, $C_{3-7}$cycloalkyl, $C_{1-4}$alkyl, phenyl, thienyl, isoxazolyl, pyrazolyl, pyridinyl or pyrimidinyl all of optionally substituted with one or more substituents selected from halogen, $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-4}$alkyl S(O)$_n$C$_{0-4}$alkyl, $C_{1-6}$haloalkyl, $C_{1-4}$haloalkoxy, halo, nitro, cyano, $C_{1-4}$alkylOC$_{1-6}$alkyl, $C_{1-6}$alkylOC$_{1-6}$alkyl OC$_{1-6}$alkyl, $C_{0-6}$alkylC(O)C$_{0-6}$alkyl, $C_{0-4}$alkylC(O) OC$_{0-4}$alkyl, $C_{0-4}$alkylOC(O)C$_{0-4}$alkyl, NR$^5$R$^6$C$_{0-4}$alkyl, NR$^5$R$^6$C(O)C$_{0-4}$alkyl, NR$^5$R$^6$C(O)C$_{0-4}$alkyl, NR$^5$R$^6$C(O) OC$_{0-4}$alkyl, NR$^5$R$^6$OC(O)C$_{0-4}$alkyl, R$^6$C(O)R$^5$NC$_{0-4}$alkyl, $C_{0-4}$alkylOC(O)C$_{0-4}$alkylNH, $C_{0-4}$alkylC(O)OC$_{0-4}$alkylNH, $C_{0-4}$alkylC(O)C$_{0-4}$alkylNH and NR$^5$R$^6$S(O)$_n$C$_{0-4}$alkyl;

X is $CH_2$, O, S, S(O), S(O)$_2$ or NH;

Y is hydrogen, halogen, $C_{1-6}$ alkyl, $C_{1-4}$alkoxy, $C_{1-4}$thioalkyl, $C_{1-4}$haloalkyl, $C_{1-4}$alkoxyhalo, nitro, cyano, hydroxy, R$^5$C(O), R$^5$OC(O), R$^5$C(O)O, S(O)$_n$C$_{1-4}$alkyl, R$^5$R$^6$NS(O)$_n$, benzyloxy, imidazolyl, $C_{1-4}$alkylNHC(O), NR$^5$R$^6$C(O), $C_{1-4}$alkylC(O)NH or NR$^5$R$^6$;

R$^5$ and R$^6$ are independently selected from hydrogen, $C_{1-4}$ alkyl and $C_{3-7}$ cycloalkyl, or R$^5$ and R$^6$ form together a group —(O)C$_{5-10}$arylC(O)—; and n is 1 or 2, or a pharmaceutically acceptable salt thereof.

One embodiment relates to compound of formula (I), wherein:

A is $C_{1-10}$alkyl, $C_{5-10}$aryl, $C_{5-10}$aryl$C_{1-6}$alkyl, $C_{5-10}$heteroaryl, $C_{5-10}$heteroaryl$C_{1-6}$alkyl, $C_{5-10}$aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)OC$_{1-6}$alkyl, $C_{5-10}$aryloxy$C_{1-10}$alkyl or NR$^5$R$^6$C$_{0-6}$alkyl whereby the aryl is optionally substituted with one or more substituents selected from B;

R$^1$ and R$^{1a}$ are independently selected from hydrogen and $C_{1-4}$alkyl;

R$^2$ is hydrogen;

R$^3$ is $C_{5-10}$aryl$C_{0-3}$alkyl, $C_{5-10}$arylOC$_{0-3}$alkyl, $C_{5-10}$heteroaryl$C_{0-3}$alkyl which are optionally substituted by one or more B;

B is $C_{0-3}$hydroxyalkyl, $C_{1-4}$alkyl, $C_{1-4}$alkoxy, $C_{1-6}$haloalkyl, $C_{1-4}$haloalkoxy, halogen or NR$^5$R$^6$C$_{0-4}$alkyl;

R$^4$ is hydrogen;

W is $C_{3-7}$cycloalkyl, $C_{1-4}$alkyl, phenyl or pyridinyl all of optionally substituted with one or more substituents selected from halogen;

X is O, S or S(O)$_2$;

Y is hydrogen or halogen; and

R$^5$ and R$^6$ are independently selected from hydrogen and $C_{1-4}$ alkyl, or R$^5$ and R$^6$ form together a group —(O)C$_{5-10}$arylC(O)—, or a pharmaceutically acceptable salt thereof.

One embodiment relates to compound of formula (I), wherein:

A is $C_{1-10}$alkyl, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O) OC$_{1-6}$alkyl or NR$^5$R$^6$C$_{0-6}$alkyl optionally substituted with one or more substituents selected from B.

R$^1$ and R$^{1a}$ are independently selected from hydrogen and $C_{1-4}$alkyl;

R$^2$ is hydrogen;

R$^3$ is $C_{5-10}$aryl$C_{0-3}$alkyl, $C_{5-10}$arylOC$_{0-3}$alkyl, $C_{5-10}$heteroaryl$C_{0-3}$alkyl which are optionally substituted by one or more B;

B is $C_{0-3}$hydroxyalkyl, $C_{1-4}$alkyl, $C_{1-4}$alkoxy, $C_{1-6}$haloalkyl, $C_{1-4}$haloalkoxy, halogen or NR$^5$R$^6$C$_{0-4}$alkyl;

R$^4$ is hydrogen;

W is $C_{3-7}$cycloalkyl, $C_{1-4}$alkyl, phenyl or pyridinyl all of optionally substituted with one or more substituents selected from halogen;

X is O, S or $S(O)_2$;

Y is hydrogen or halogen; and $R^5$ and $R^6$ are independently selected from hydrogen and $C_{1-4}$ alkyl, or $R^5$ and $R^6$ form together a group —(O)$C_{5-10}$arylC(O)—, or a pharmaceutically acceptable salt thereof.

Another embodiment relates to compound of formula (I), wherein:

A is $C_{5-10}$aryl, $C_{5-10}$aryl$C_{1-6}$alkyl, $C_{5-10}$aryl$C_{1-6}$alkoxy or $C_{5-10}$aryloxy$C_{1-10}$alkyl whereby the aryl is optionally substituted with one or more substituents selected from B;

$R^1$ and $R^{1a}$ are independently selected from hydrogen and $C_{1-4}$alkyl;

$R^2$ is hydrogen;

$R^3$ is $C_{5-10}$aryl$C_{0-3}$alkyl, $C_{5-10}$aryl$OC_{0-3}$alkyl, $C_{5-10}$heteroaryl$C_{0-3}$alkyl which are optionally substituted by one or more B;

B is $C_{0-3}$hydroxyalkyl, $C_{1-4}$alkyl, $C_{1-4}$alkoxy, $C_{1-6}$haloalkyl, $C_{1-4}$haloalkoxy, halogen or $NR^5R^6C_{0-4}$alkyl;

$R^4$ is hydrogen;

W is $C_{3-7}$cycloalkyl, $C_{1-4}$alkyl, phenyl or pyridinyl all of optionally substituted with one or more substituents selected from halogen;

X is O, S or $S(O)_2$;

Y is hydrogen or halogen; and $R^5$ and $R^6$ are independently selected from hydrogen and $C_{1-4}$ alkyl, or $R^5$ and $R^6$ form together a group —(O)$C_{5-10}$arylC(O)—, or a pharmaceutically acceptable salt thereof.

A further embodiment relates to compound of formula (I), wherein:

A is $C_{5-10}$heteroaryl or $C_{5-10}$heteroaryl$C_{1-6}$alkyl optionally substituted with one or more substituents selected from B;

$R^1$ and $R^{1a}$ are independently selected from hydrogen and $C_{1-4}$alkyl;

$R^2$ is hydrogen;

$R^3$ is $C_{5-10}$aryl$C_{0-3}$alkyl, $C_{5-10}$aryl$OC_{0-3}$alkyl, $C_{5-10}$heteroaryl$C_{0-3}$alkyl which are optionally substituted by one or more B;

B is $C_{0-3}$hydroxyalkyl, $C_{1-4}$alkyl, $C_{1-4}$alkoxy, $C_{1-6}$haloalkyl, $C_{1-4}$haloalkoxy, halogen or $NR^5R^6C_{0-4}$alkyl;

$R^4$ is hydrogen;

W is $C_{3-7}$cycloalkyl, $C_{1-4}$alkyl, phenyl or pyridinyl all of optionally substituted with one or more substituents selected from halogen;

X is O, S or $S(O)_2$;

Y is hydrogen or halogen; and $R^5$ and $R^6$ are independently selected from hydrogen and $C_{1-4}$ alkyl, or $R^5$ and $R^6$ form together a group —(O)$C_{5-10}$arylC(O)—, or a pharmaceutically acceptable salt thereof.

One embodiment relates to compound of formula (I), wherein:

A is $C_{1-10}$alkyl, $C_{5-10}$aryl, $C_{5-10}$aryl$C_{1-6}$alkyl, $C_{5-10}$heteroaryl, $C_{5-10}$heteroaryl$C_{1-6}$alkyl, $C_{5-10}$aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)OC$_{1-6}$alkyl, $C_{5-10}$aryloxy$C_{1-10}$alkyl or $NR^5R^6C_{0-6}$alkyl whereby the aryl is optionally substituted with one or more substituents selected from B;

$R^1$ and $R^{1a}$ are independently selected from hydrogen, $C_{1-4}$alkyl, $C_{1-4}$haloalkyl, $C_{1-4}$hydroxyalkyl and $C_{1-4}$alkylOC$_{1-4}$alkyl;

$R^2$ is hydrogen or $C_{1-4}$alkyl;

$R^3$ is $C_{3-7}$ cycloalkyl (optionally substituted by halogen or $C_{1-6}$alkyl), $C_{5-10}$aryl$C_{0-3}$alkyl, $C_{5-10}$aryl$OC_{0-3}$alkyl, $C_{5-10}$heteroaryl$C_{0-3}$alkyl, $C_{1-6}$alkyl, $C_{1-6}$alkenyl or $C_{1-6}$alkynyl which are optionally substituted by one or more B;

B is $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-3}$alkylS(O)$_n$$C_{0-4}$alkyl, $C_{1-6}$haloalkyl, $C_{1-4}$haloalkoxy, halogen, nitro, cyano, $C_{1-4}$alkylOC$_{1-6}$alkyl, $C_{0-6}$alkylOC$_{1-4}$alkyl OC$_{0-4}$alkyl, $C_{0-6}$alkylC(O)$C_{0-6}$alkyl, $C_{0-4}$alkylC(O) OC$_{0-4}$alkyl, $C_{0-4}$alkylOC(O)$C_{0-4}$alkyl, $NR^5R^6C_{0-4}$alkyl, $NR^5R^6C(O)C_{0-4}$alkyl, $NR^5R^6OC(O)C_{0-4}$alkyl, $NR^5R^6C(O)$ OC$_{0-4}$alkyl, $R^6C(O)R^5NC_{0-4}$alkyl, $C_{0-4}$alkylOC(O)$C_{0-4}$alkylNH, $C_{0-4}$alkylC(O)OC$_{0-4}$alkylNH, $C_{0-4}$alkylC(O)$C_{0-4}$alkylNH or $NR^5R^6S(O)_n$$C_{0-4}$alkyl;

$R^4$ is hydrogen, hydroxy, halogen, $C_{1-4}$ alkyl or $C_{1-4}$ haloalkyl;

W is $C_{3-7}$cycloalkyl, $C_{1-4}$alkyl, phenyl, thienyl, isoxazolyl, pyrazolyl, pyridinyl or pyrimidinyl all of optionally substituted with one or more substituents selected from halogen, $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-4}$alkyl $S(O)_n$$C_{0-4}$alkyl, $C_{1-6}$haloalkyl, $C_{1-4}$haloalkoxy, halo, nitro, cyano, $C_{1-4}$alkylOC$_{1-6}$alkyl, $C_{1-6}$alkylOC$_{1-4}$alkyl OC$_{1-6}$alkyl, $C_{0-6}$alkylC(O)$C_{0-6}$alkyl, $C_{0-4}$alkylC(O) OC$_{0-4}$alkyl, $C_{0-4}$alkylOC(O)$C_{0-4}$alkyl, $NR^5R^6C_{0-4}$alkyl, $NR^5R^6C(O)C_{0-4}$alkyl, $NR^5R^6C(O)OC_{0-4}$alkyl, $NR^5R^6OC(O)C_{0-4}$alkyl, $R^6C(O)R^5NC_{0-4}$alkyl, $C_{0-4}$alkylOC(O)$C_{0-4}$alkylNH, $C_{0-4}$alkylC(O)OC$_{0-4}$alkylNH, $C_{0-4}$alkylC(O)$C_{0-4}$alkylNH and $NR^5R^6S(O)_n$$C_{0-4}$alkyl;

X is $CH_2$, O, S, S(O), $S(O)_2$ or NH;

Y is hydrogen, halogen, $C_{1-6}$ alkyl, $C_{1-4}$alkoxy, $C_{1-4}$thioalkyl, $C_{1-4}$haloalkyl, $C_{1-4}$alkoxyhalo, nitro, cyano, hydroxy, $R^5C(O)$, $R^5OC(O)$, $R^5C(O)O$, $S(O)_n$$C_{1-4}$alkyl, $R^5R^6NS(O)_n$, benzyloxy, imidazolyl, $C_{1-4}$alkylNHC(O), $NR^5R^6C(O)$, $C_{1-4}$alkylC(O)NH or $NR^5R^6$;

$R^5$ and $R^6$ are independently selected from hydrogen, $C_{1-4}$ alkyl and $C_{3-7}$ cycloalkyl, or $R^5$ and $R^6$ form together a group —(O)$C_{5-10}$arylC(O)—; and n is 1 or 2, or a pharmaceutically acceptable salt thereof.

One embodiment relates to compounds of formula I wherein A is

A is $C_{1-10}$alkyl, $C_{5-10}$aryl, $C_{5-10}$aryl$C_{1-6}$alkyl, $C_{5-10}$heteroaryl, $C_{5-10}$heteroaryl$C_{1-6}$alkyl, $C_{5-10}$aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)OC$_{1-6}$alkyl, $C_{5-10}$aryloxy$C_{1-10}$alkyl or $NR^5R^6C_{0-6}$alkyl whereby the aryl is optionally substituted with one or more substituents selected from B.

In a further embodiment A is $C_{3-6}$cycloalkyl. In another embodiment A is cyclopropyl or cyclopentyl.

In a further embodiment A is $C_{3-6}$cycloalkyl$C_{1-2}$alkyl. In yet another embodiment A is cyclopentyl-methyl In a further embodiment A is $C_{1-10}$alkyl. In one embodiment A is methyl, ethyl, n-propyl, i-propyl, n-butyl, i-butyl, s-butyl, t-butyl, n-pentyl, i-pentyl, neo-pentyl, n-hexyl or i-hexyl.

In a further embodiment A is methyl. In another embodiment A is n-propyl. In yet another embodiment A is n-pentyl or s-pentyl. In yet a further embodiment A is s-butyl or n-butyl.

In another embodiment A is n-hexyl.

In one embodiment A is $C_{1-6}$haloalkyl, In another embodiment A is fluoromethyl, difluoromethyl, trifluoromethyl, fluoroethyl, difluoroethyl, trifluoroethyl or trifluoropropyl. In another embodiment A is trifluoromethyl. In yet another embodiment A is trifluoromethyl, trifluoroethyl or trifluoropropyl.

In a further embodiment A is $C_{5-10}$heteroaryl$C_{1-6}$alkyl. In one embodiment A is dioxoisoindolyl-ethyl.

In another embodiment A is $C_{5-6}$heteroaryl optionally substituted with B. In a further embodiment A is imidazolyl or isooxazolyl optionally substituted with B. In a further embodiment A is imidazolyl or isooxazolyl substituted with one or two methyl.

In one embodiment A is $C_{5-6}$aryl$C_{1-6}$alkoxy optionally substituted with $C_{1-4}$alkoxy. In yet a further embodiment A is phenyl-ethoxy substituted with methoxy.

In another embodiment A is $C_{1-4}$alkylOC(O)$C_{1-4}$alkyl. In one embodiment A is $C_{1-2}$alkylOC(O)$C_{1-2}$alkyl. In another embodiment propanoate.

In one embodiment A is $C_{5-10}$heteroaryl. In a further embodiment A is pyridinyl.

One embodiment relates to compounds of formula I wherein $R^1$ and $R^{1a}$ are independently selected from hydrogen and $C_{1-4}$alkyl. In another embodiment $R^1$ is hydrogen. In another embodiment $R^1$ is methyl.

In yet a further embodiment $R^{1a}$ is hydrogen.

In yet another embodiment $R^2$ is hydrogen.

One embodiment relates to compounds of formula I wherein $R^3$ is $C_{5-10}$aryl$C_{0-3}$alkyl, $C_{5-10}$arylOC$_{0-3}$alkyl, $C_{5-10}$heteroaryl$C_{0-3}$alkyl which are optionally substituted by one or more B. In a further embodiment $R^3$ is $C_{5-6}$aryl. In another embodiment $R^3$ is phenyl. In a further embodiment $R^3$ is phenyl substituted with B. In yet a further embodiment $R^3$ is phenyl substituted with halogen or $R^5S(O)_2$, wherein $R^5$ is $C_{1-4}$alkyl. In one embodiment B is fluoro. In another embodiment B is methyl-S(O)$_2$.

In yet a further embodiment $R^3$ is $C_{5-6}$heteroaryl. In one embodiment $R^3$ is pyridinyl substituted with B. In yet a further embodiment $R^3$ is pyridinyl substituted with $C_{1-4}$alkoxy.

In one embodiment $R^3$ is pyridinyl substituted with methoxy.

In another embodiment $R^3$ together with B form a dihydrobenzodioxinyl group as in example 43.

One embodiment relates to compounds of formula I wherein $R^1$ is $C_{1-4}$alkyl, $R^{1a}$ is hydrogen, $R^2$ is hydrogen and $R^3$ is $C_{5-10}$aryl, whereby aryl is optionally substituted by one or more B. In another embodiment B is halogen or $R^5S(O)_2$.

One embodiment relates to compounds of formula I wherein W is $C_{3-7}$cycloalkyl, $C_{1-4}$alkyl, phenyl or pyridinyl all of optionally substituted with one or more substituents selected from halogen. In a further embodiment W is $C_{3-6}$cycloalkyl, $C_{1-4}$alkyl, phenyl or pyridinyl optionally substituted with one substituent selected from halogen. In yet another embodiment W is phenyl. In another embodiment W is phenyl substituted with halogen. In a further embodiment W is phenyl substituted with fluoro.

In one embodiment W is cyclopentyl. In another embodiment W is iso-propyl.

In yet another embodiment W is pyridinyl.

One embodiment relates to compounds of formula I wherein X is O.

In another embodiment X is S. In a further embodiment X is S(O)$_2$.

One embodiment relates to compounds of formula I wherein $R^1$ is $C_{1-4}$alkyl, $R^{1a}$ is hydrogen, $R^2$ is hydrogen, X is O and $R^3$ is $C_{5-10}$aryl, whereby aryl is optionally substituted is by one or more B. In another embodiment B is halogen or $R^5S(O)_2$.

One embodiment relates to compounds of formula I wherein Y is hydrogen.

In another embodiment Y is halogen. In a further embodiment Y is chloro.

One embodiment relates to compounds of formula I wherein $R^5$ and $R^6$ are independently selected from hydrogen and $C_{1-4}$ alkyl. In another embodiment $R^5$ and $R^6$ form together a group —(O)$C_{5-10}$arylC(O)—.

Particular examples of compounds of formula (I) are compounds of formula (IA)

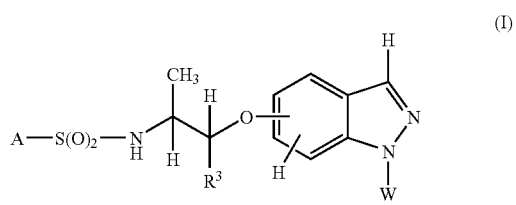

where A, $R^3$ and W are as defined above, or a pharmaceutically acceptable salt thereof.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{0-6}$' means a carbon group having 0, 1, 2, 3, 4, 5 or 6 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, neo-pentyl, n-hexyl or i-hexyl. The term $C_{1-4}$ alkyl having 1 to 4 carbon atoms and may be but are not limited to methyl, ethyl, n-propyl, i-propyl or tert-butyl. The term "$C_0$" refers to a situation where no carbon atom is present.

The term "alkoxy", unless stated otherwise, refers to radicals of the general formula —O—R, wherein R is selected from a hydrocarbon radical. The term "alkoxy" may include, but is not limited to methoxy, ethoxy, propoxy, isopropoxy, butoxy, t-butoxy, isobutoxy, cyclopropylmethoxy, allyloxy or propargyloxy.

In this specification, unless stated otherwise, the term "cycloalkyl" refers to an optionally substituted, partially or completely saturated monocyclic, bicyclic or bridged hydrocarbon ring system. The term "$C_{1-6}$cycloalkyl" may be, but is not limited to cyclopropyl, cyclobutyl, cyclopentyl or cyclohexyl.

In this specification, unless stated otherwise, the terms "halo" and "halogen" may be fluorine, iodine, chlorine or bromine.

In this specification, unless stated otherwise, the term "haloalkyl" means an alkyl group as defined above, which is substituted with halogen as defined above. The term "$C_1$-$C_6$haloalkyl" may include, but is not limited to fluoromethyl, difluoromethyl, trifluoromethyl, fluoroethyl, difluoroethyl or bromopropyl. The term "$C_1$-$C_3$haloalkylO" may include, but is not limited to fluoromethoxy, difluoromethoxy, trifluoromethoxy, fluoroethoxy or difluoroethoxy.

In this specification, unless stated otherwise, the term "$C_{5-10}$aryl" refers to an aromatic group such as for example, phenyl or naphthyl.

In this specification, unless stated otherwise, the term "$C_{5-10}$heteroaryl" refers to a mono- or bicyclic aromatic or partially aromatic ring containing one or more heteroatoms independently selected from nitrogen, oxygen, sulphur.

Example of heteroaryls are oxazolyl, furyl, thienyl, pyrrolyl, pyrazolyl, imidazolyl, pyridinyl, pyrimidinyl, indolyl, indazolyl, benzfuryl or benzthienyl. Heteroaryl may also be dihydrobenzodioxinyl, quinolinyl or isoquinolinyl.

When phenyl is substituted by $OCH_2O$, $OCH_2CH_2O$ or $OCH_2CH_2$ these groups link to adjacent carbons on the phenyl ring.

$C_{5-10}arylC_{1-4}alkyl$ is for example benzyl. $C_{5-10}aryl$ $C_{1-4}alkoxy$ is, for example a methoxy substituted with a phenyl. $C_{1-4}alkoxyC_{5-10}aryl$ is, for example, a phenyl substituted with methoxy.

It will be appreciated that throughout the specification, the number and nature of substituents on rings in the compounds of the invention will be selected so as to avoid sterically undesirable combinations.

Compounds of the present invention have been named with the aid of computer software (ACDLabs 8.0/Name(IUPAC)).

In another embodiment, the compounds of the invention are selected from

N-[(1R,2S)-1-[1-(4-fluorophenyl)indazol-5-yl]oxy-1-phenyl-propan-2-yl]cyclopropanesulfonamide,
N-[(1R,2S)-1-[1-(4-fluorophenyl)indazol-5-yl]oxy-1-phenyl-propan-2-yl]propane-1-sulfonamide,
N-[(1R,2S)-1-[1-(4-fluorophenyl)indazol-4-yl]oxy-1-phenyl-propan-2-yl]cyclopropanesulfonamide,
N-[(1R,2S)-1-[1-(6-fluoropyridin-3-yl)indazol-5-yl]oxy-1-phenyl-propan-2-yl]cyclopropanesulfonamide,
N-[(1R,2S)-1-[1-(4-fluorophenyl)indazol-5-yl]oxy-1-phenyl-propan-2-yl]methanesulfonamide,
N-[(1R,2S)-1-[1-(4-fluorophenyl)indazol-5-yl]oxy-1-phenyl-propan-2-yl]-1-phenyl-methanesulfonamide,
1,1,1-trifluoro-N-[(1R,2S)-1-[1-(4-fluorophenyl)indazol-5-yl]oxy-1-phenyl-propan-2-yl]methanesulfonamide,
5-[(1R,2S)-2-(dimethylsulfamoylamino)-1-phenyl-propoxy]-1-(4-fluorophenyl)indazole,
N-[(1R,2S)-1-[1-(4-fluorophenyl)indazol-5-yl]oxy-1-phenyl-propan-2-yl]propane-2-sulfonamide,
2-(1,3-dioxoisoindol-2-yl)-N-[(1R,2S)-1-[1-(4-fluorophenyl)indazol-5-yl]oxy-1-phenyl-propan-2-yl]ethanesulfonamide,
N-[(1R,2S)-1-[1-(4-fluorophenyl)indazol-5-yl]oxy-1-phenyl-propan-2-yl]-3-(4-methoxyphenoxy)propane-1-sulfonamide,
N-[(1R,2S)-1-[1-(4-fluorophenyl)indazol-5-yl]oxy-1-phenyl-propan-2-yl]ethanesulfonamide,
N-[(1R,2S)-1-[1-(4-fluorophenyl)indazol-5-yl]oxy-1-phenyl-propan-2-yl]pentane-2-sulfonamide,
N-[(1R,2S)-1-[1-(4-fluorophenyl)indazol-5-yl]oxy-1-phenyl-propan-2-yl]butane-2-sulfonamide,
N-[(1R,2S)-1-[1-(4-fluorophenyl)indazol-5-yl]oxy-1-phenyl-propan-2-yl]butane-1-sulfonamide,
N-[(1R,2S)-1-[1-(4-fluorophenyl)indazol-5-yl]oxy-1-phenyl-propan-2-yl]-1-propane-1-sulfonamide,
N-[(1R,2S)-1-[1-(4-fluorophenyl)indazol-5-yl]oxy-1-phenyl-propan-2-yl]pentane-1-sulfonamide,
3,3,3-trifluoro-N-[(1R,2S)-1-[1-(4-fluorophenyl)indazol-5-yl]oxy-1-phenyl-propan-2-yl]propane-1-sulfonamide,
methyl 3-[[(1R,2S)-1-[1-(4-fluorophenyl)indazol-5-yl]oxy-1-phenyl-propan-2-yl]sulfamoyl]propanoate,
1-cyclopentyl-N-[(1R,2S)-1-[1-(4-fluorophenyl)indazol-5-yl]oxy-1-phenyl-propan-2-yl]methanesulfonamide,
N-[(1R,2S)-1-[1-(4-fluorophenyl)indazol-5-yl]oxy-1-phenyl-propan-2-yl]cyclopentanesulfonamide,
2,2,2-trifluoro-N-[(1R,2S)-1-[1-(4-fluorophenyl)indazol-5-yl]oxy-1-phenyl-propan-2-yl]ethanesulfonamide,
1-cyclohexyl-N-[(1R,2S)-1-[1-(4-fluorophenyl)indazol-5-yl]oxy-1-phenyl-propan-2-yl]methanesulfonamide,
N-[(1R,2S)-1-[1-(4-fluorophenyl)indazol-5-yl]oxy-1-phenyl-propan-2-yl]hexane-1-sulfonamide,
N-[(1R,2S)-1-[1-(4-fluorophenyl)indazol-5-yl]oxy-1-phenyl-propan-2-yl]pyridine-3-sulfonamide,
N-[1-[1-(4-fluorophenyl)indazol-5-yl]oxy-2-methyl-1-phenyl-propan-2-yl]cyclopropanesulfonamide,
N-[(1R,2S)-1-[1-(4-fluorophenyl)indazol-5-yl]oxy-1-(4-methylsulfanylphenyl)propan-2-yl]cyclopropanesulfonamide,
N-[(1S,2S)-1-[1-(4-fluorophenyl)indazol-5-yl]oxy-1-(4-methylsulfanylphenyl)propan-2-yl]cyclopropanesulfonamide,
N-[(1R,2S)-1-[1-(4-fluorophenyl)indazol-5-yl]oxy-1-(4-methylsulfanylphenyl)propan-2-yl]cyclopropanesulfonamide,
N-[(1R,2S)-1-phenyl-1-(1-propan-2-ylindazol-5-yl)oxy-propan-2-yl]methanesulfonamide,
N-[(1R,2S)-1-[1-(4-fluorophenyl)indazol-5-yl]oxy-1-(4-methylsulfinylphenyl)propan-2-yl]cyclopropanesulfonamide,
N-[(1R,2S)-1-(1-cyclopentylindazol-5-yl)oxy-1-phenyl-propan-2-yl]cyclopropanesulfonamide,
N-[(1R,2S)-1-phenyl-1-(1-propan-2-ylindazol-5-yl)oxy-propan-2-yl]cyclopropanesulfonamide,
N-[(1R,2S)-1-[1-(4-fluorophenyl)indazol-5-yl]oxy-1-(4-methylsulfonylphenyl)propan-2-yl]cyclopropanesulfonamide,
N-[(1R,2S)-1-[6-chloro-1-(4-fluorophenyl)indazol-5-yl]oxy-1-(4-fluorophenyl)propan-2-yl]cyclopropanesulfonamide,
N-[(1R,2R)-1-[6-chloro-1-(4-fluorophenyl)indazol-5-yl]oxy-1-(4-fluorophenyl)propan-2-yl]cyclopropanesulfonamide,
N-[2-[1-(4-fluorophenyl)indazol-5-yl]sulfanyl-2-phenyl-ethyl]cyclopropanesulfonamide,
N-[(1R,2S)-1-[1-(4-fluorophenyl)indazol-5-yl]sulfanyl-1-phenyl-propan-2-yl]methanesulfonamide,
N-[(1R,2S)-1-[1-(4-fluorophenyl)indazol-5-yl]sulfonyl-1-phenyl-propan-2-yl]methanesulfonamide,
N-[(2R)-2-[1-(4-fluorophenyl)indazol-5-yl]oxy-2-phenyl-ethyl]cyclopropanesulfonamide,
N-[(2S)-2-[1-(4-fluorophenyl)indazol-5-yl]oxy-2-phenyl-ethyl]cyclopropanesulfonamide,
N-[(1R,2S)-1-[1-(4-fluorophenyl)indazol-5-yl]oxy-1-quinolin-3-yl-propan-2-yl]cyclopropanesulfonamide,
N-[(1R,2S)-1-(2,5-dioxabicyclo[4.4.0]deca-7,9,11-trien-8-yl)-1-[1-(4-fluorophenyl)indazol-5-yl]oxy-propan-2-yl]cyclopropanesulfonamide,
Cyclopropanesulfonic acid N-{1-[6-methoxypyridin-3-yl]-1-[(1-pyridin-2-yl-1H-indazol-5-yl)oxy]propan-2-yl}amide,
Cyclopropanesulfonic acid N-{1-[6-methoxypyridin-3-yl]-1-[(1-pyridin-3-yl-1H-indazol-5-yl)oxy]propan-2-yl}amide,
Cyclopropanesulfonic acid N-{1-[2-methoxypyridin-4-yl]-1-[(1-pyridin-2-yl-1H-indazol-5-yl)oxy]propan-2-yl}amide,
Cyclopropanesulfonic acid N-{1-[2-methoxypyridin-4-yl]-1-[(1-pyridin-2-yl-1H-indazol-5-yl)oxy]butan-2-yl}amide,
1-Methyl-1H-imidazole-4-sulfonic acid N-[(1R,2S)-1-[1-(4-fluorophenyl)indazol-5-yl]oxy-1-phenyl-propan-2-yl]amide, and
3,5-Dimethylisooxazole-4-sulfonic acid N-[(1R,2S)-1-[1-(4-fluorophenyl)indazol-5-yl]oxy-1-phenyl-propan-2-yl]amide,
or a pharmaceutically acceptable salt thereof The compounds of formula (I) and pharmaceutically acceptable salts thereof may exist in solvated, for example hydrated, as well as unsolvated forms, and the present invention encompasses all such forms.

Compounds of formula (I) above may be converted to a pharmaceutically acceptable salt thereof, preferably an acid addition salt such as a hydrochloride, hydrobromide, phosphate, sulfphate, acetate, ascorbate, benzoate, fumarate, hemifumarate, furoate, succinate, maleate, tartrate, citrate, oxalate, xinafoate, methanesulphonate, p-toluenesulphonate, benzenesulphonate, ethanesulphonate, 2-naphthalenesulfonate, mesytilenesulfonate, nitric acid, 1,5-naphthalenedisulphonate, p-xylenesulphonate, aspartate or glutamate.

They may also include basic addition salts such as an alkali metal salt for example sodium or potassium salts, an alkaline earth metal salt for example calcium or magnesium salts, a transition metal salt such as a zinc salt, an organic amine salt for example a salt of triethylamine, diethylamine, morpholine, N-methylpiperidine, N-ethylpiperidine, piperazine, procaine, dibenzylamine, N,N-dibenzylethylamine, choline or 2-aminoethanol or amino acids for example lysine or arginine.

Compounds of formula (I) may include an asymmetric centre and be chiral in nature. Where the compound is chiral, it may be in the form of a single stereoisomer, such as a enantiomer, or it may be in the form of mixtures of these stereoisomers in any proportions, including racemic mixtures. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

In another aspect the present invention provides a compound of formula (I) wherein the group:

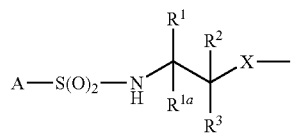

is bonded to the 5-position of the indazolyl ring system.

In another aspect the present invention provides the individual compound:
N-[(1R,2S)-1-[1-(4-fluorophenyl)indazol-5-yl]oxy-1-phenyl-propan-2-yl]cyclopropanesulfonamide
or a pharmaceutically acceptable salt thereof Process The compounds of formula (I) can be prepared using or adapting methods disclosed in the art, or by using or adapting the method disclosed in the Example below. Starting materials for the preparative methods are either commercially available or can be prepared by using or adapting literature methods.

For example a compound of formula (I) can be prepared by coupling a compound of formula (II):

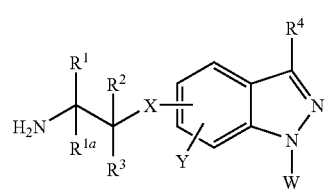

with a compound of formula (III):

wherein $L^1$ is a leaving group (such as halogen (for example chloro) or mesylate or tosylate), in a suitable solvent (such as pyridine, THF or DMF), in the presence of a suitable base (such as a tri($C_{1-6}$ alkyl)amine, for example diisopropylethylamine, or pyridine) and at a suitable temperature (such as −10 to 50° C.).

A compound of formula (II), wherein X is O, S or NH, may be prepared by coupling a compound of formula (IV)

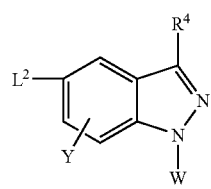

wherein $R^4$, W and Y are defined as in compounds of formula (I) and $L^2$ is a leaving group (such as halogen or triflate) with a compound of formula (V)

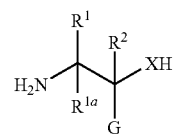

wherein $R^1$, $R^{1a}$ and $R^2$ are defined as in compounds of formula (I) and G corresponds to $R^3$ or a protected precursor to $R^3$.

The reaction can be performed in a suitable solvent (such as an aromatic solvent, for example toluene) or a polar, aprotic solvent, such as DMF or butyronitril, in the presence of a suitable base (such as a alkali metal alkoxide (for example sodium tert-butoxide) or, cesium carbonate, preferable mediated by a suitable metal catalyst such as Copper(I) iodide at a suitable temperature (for example in the range 80° to 120° C.).

Alternatively, a compound of formula (II) may be prepared reaction of a compound of formula (VII)

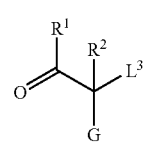

with a compound of formula (VIII)

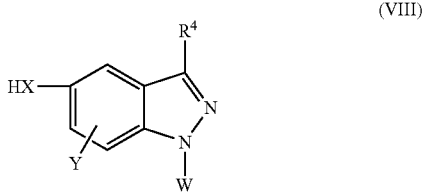

wherein $R^1$, $R^2$, $R^4$, X, W and Y are defined as in compounds of formula (I), G corresponds to $R^3$ or a protected precursor to $R^3$ and $L^3$ is a leaving group (such as halogen, mesylate or tosylate).

The reaction can be performed in a suitable solvent (such as DCM, DMF or acetonitrile), in the presence of a suitable base (such as an alkali metal carbonate, for example cesium carbonate or potassium carbonate) at a suitable temperature (for example in the range −10 to 50° C.), followed by a subsequent reductive amination step using or adopting literature methods.

Alternatively, a compound of formula (II) may be prepared by reaction of a compound of formula (VIII) and a compound of formula (IX)

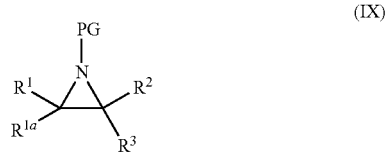

wherein $R^1$, $R^{1a}$, $R^2$ and $R^3$ are defined as in compounds of formula (I) and PG is a suitable protecting group such as BOC, Ms, Ns, Ts or related carbonyl- or sulfonyl residues.

The reaction can be performed in a suitable solvent such as DCM or toluene in the presence of a suitable base such as NaH or KOtBu, followed by a deprotection step using or adopting literature methods.

As a specific case of a compound of formula (V), a compound of formula (X) might be used to prepare a compound of formula (II)

wherein $R^1$, $R^2$ and G are defined as in compounds of formula (V).

Compounds of formula (X) may be prepared by reacting a nucleophile G-M with a carbonyl compound of formula (XI) followed reduction and subsequent deprotection of the intermediate of formula (XII)

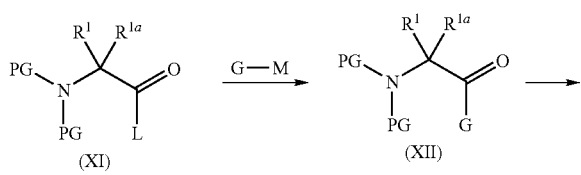

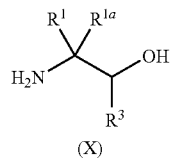

wherein $R^1$, $R^{1a}$ are defined as in compounds of formula (I) and G corresponds to $R^3$ or a protected precursor to $R^3$ and L is a leaving group (such as alkoxy, methoxy(methyl)amino). M is a metal such as Li or Mg-halide.

The addition of the nucleophile may be performed in a suitable aprotic solvent such as THF at moderate temperature between −10 and 50° C. The following reduction and deprotection steps might be carried out by using or adopting literature methods.

Alternatively, compounds of formula (X) may be prepared by a reaction of a nuceophile G-M with an aldehyde of formula (XIII) and a subsequent deprotection.

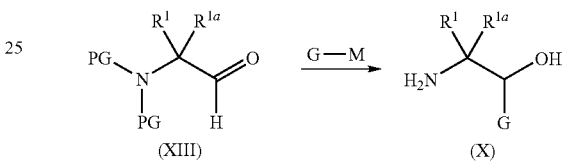

wherein $R^1$, $R^{1a}$ are defined as in compounds of formula (I) and are defined as in compounds of formula (I), G corresponds to $R^3$ or a protected precursor to $R^3$ and PG is a protecting group or hydrogen. M is a metal such as an alkali metal (e.g. Li) or Mg-halide. The reaction may be performed by following disclosed protocols for addition of carbanions to aldehydes.

Another way to prepare a compound of formula (X) is the reaction of nitroalkyles of formula (XIV) with aldehydes of formula (XV), followed by reduction of the nitro function

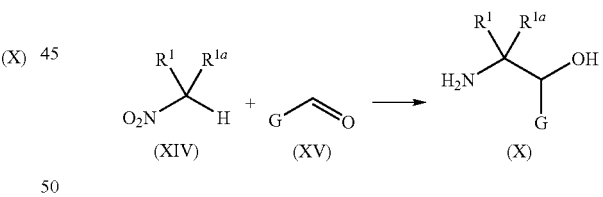

wherein $R^1$ and $R^{1a}$ are defined as in compounds of formula (I), G corresponds to $R^3$ or a protected precursor to $R^3$ and PG is a protecting group or hydrogen.

Both steps may be carried out by following or adopting literature methods.

The invention further provides processes for the preparation of these compounds of formula (I).

Medical Use

Because of their ability to bind to the glucocorticoid receptor the compounds of formula (I) are useful as anti-inflammatory agents, and can also display antiallergic, immunosuppressive and anti-proliferative actions. Thus, a compound of formula (I), or a pharmaceutically acceptable salt thereof can be used as a medicament for the treatment or prophylaxis of one or more of the following pathologic conditions (disease states) in a mammal (such as a human):

(i) Lung diseases, which coincide with inflammatory, allergic and/or proliferative processes:
   chronically obstructive lung diseases of any origin, mainly bronchial asthma
   bronchitis of different origins
   all forms of restructive lung diseases, mainly allergic alveolitis
   all forms of pulmonary edema, mainly toxic pulmonary edema
   sarcoidoses and granulomatoses, such as Boeck's disease
(ii) Rheumatic diseases/auto-immune diseases/degenerative joint diseases, which coincide with inflammatory, allergic and/or proliferative processes:
   all forms of rheumatic diseases, especially rheumatoid arthritis, acute rheumatic fever, polymyalgia rheumatica, collagenoses
   reactive arthritis
   inflammatory soft-tissue diseases of other origins
   arthritic symptoms in degenerative joint diseases (arthroses)
   traumatic arthritides
   collagen diseases of other origins, for example systemic lupus erythematodes, sclerodermia, polymyositis, dermatomyositis, polyarteritis nodosa, temporal arteritis
   Sjögren's syndrome, Still syndrome, Felty's syndrome
(iii) Allergies, which coincide with inflammatory, allergic and/or proliferative processes:
   All forms of allergic reactions, for example Quincke's edema, hay fever, insect bites, allergic reactions to pharmaceutical agents, blood derivatives, contrast media, etc., anaphylactic shock, urticaria, contact dermatitis
(iv) Dermatological diseases, which coincide with inflammatory, allergic and/or proliferative processes:
   atopic dermatitis (mainly in children)
   psoriasis
   erythematous diseases, triggered by different noxae, for example radiation, chemicals, burns, etc.
   acid burns
   bullous dermatoses
   diseases of the lichenoid group
   itching (for example of allergic origins)
   all forms of eczema, such as, for example, atopic eczema or seborrheal eczema
   rosacea
   pemphigus vulgaris
   erythema exudativum multiforme
   erythema nodosum
   balanitis
   vulvitis
   inflammatory hair loss, such as alopecia areata
   cutaneous T-cell lymphoma
(v) Nephropathies, which coincide with inflammatory, allergic and/or proliferative processes:
   nephrotic syndrome
   all nephritides
(vi) Liver diseases, which coincide with inflammatory, allergic and/or proliferative processes:
   acute liver cell decomposition
   acute hepatitis of different origins, for example virally-, toxically- or pharmaceutical agent-induced
   chronically aggressive and/or chronically intermittent hepatitis
(vii) Gastrointestinal diseases, which coincide with inflammatory, allergic and/or proliferative processes:
   regional enteritis (Crohn's disease)
   ulcerative colitis
   gastroenteritis of other origins, for example native sprue
(viii) Proctological diseases, which coincide with inflammatory, allergic and/or proliferative processes:
   anal eczema
   fissures
   hemorrhoids
   idiopathic proctitis
(ix) Eye diseases, which coincide with inflammatory, allergic and/or proliferative processes:
   allergic keratitis, uvenitis iritis
   conjunctivitis
   blepharitis
   optic neuritis
   choroiditis
   sympathetic ophthalmia
(x) Diseases of the ear-nose-throat area, which coincide with inflammatory, allergic and/or proliferative processes:
   allergic rhinitis, hay fever
   otitis extema, for example caused by contact dermatitis, infection, etc.
   otitis media
(xi) Neurological diseases, which coincide with inflammatory, allergic and/or proliferative processes:
   cerebral edema, mainly tumor-induced cerebral edema
   multiple sclerosis
   acute encephalomyelitis
   different forms of convulsions, for example infantile nodding spasms
(xii) Blood diseases, which coincide with inflammatory, allergic and/or proliferative processes:
   acquired haemolytic anemia
   idiopathic thrombocytopenia
(xiii) Tumor diseases, which coincide with inflammatory, allergic and/or proliferative processes:
   acute lymphatic leukaemia
   malignant lymphoma
   lymphogranulomatoses
   lymphosarcoma
   extensive metastases, mainly in breast and prostate cancers
(xiv) Endocrine diseases, which coincide with inflammatory, allergic and/or proliferative processes:
   endocrine orbitopathy
   thyrotoxic crisis
   de Quervain's thyroiditis
   Hashimoto's thyroiditis
   hyperthyroidism
(xv) Transplants, which coincide with inflammatory, allergic and/or proliferative processes;
(xvi) Severe shock conditions, which coincide with inflammatory, allergic and/or proliferative processes, for example anaphylactic shock
(xvii) Substitution therapy, which coincides with inflammatory, allergic and/or proliferative processes, with:
   innate primary suprarenal insufficiency, for example congenital adrenogenital syndrome
   acquired primary suprarenal insufficiency, for example Addison's disease, autoimmune adrenalitis, meta-infective, tumors, metastases, etc
   innate secondary suprarenal insufficiency, for example congenital hypopituitarism acquired secondary suprarenal insufficiency, for example meta-infective, tumors, etc.

(xviii) Emesis, which coincides with inflammatory, allergic and/or proliferative processes:
for example in combination with a 5-HT$_3$-antagonist in cytostatic-agent-induced vomiting.

Without prejudice to the foregoing, the compounds of formula (I) can also be used to treat disorders such as: Conies Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, oesophageal varicies, Addison's Disease, muscle weakness, increased melanin pigmentation of the skin, weight loss, hypotension, hypoglycemia, Cushing's Syndrome, obesity, hypertension, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, and Little's syndrome, systemic inflammation, inflammatory bowel disease, systemic lupus erythematosus, discoid lupus erythematosus, polyartitis nodosa, Wegener's granulomatosis, giant cell arthritis, rheumatoid arthritis, osteoarthritis, hay fever, allergic rhinitis, contact dermatitis, atopic dermatitis, exfoliative dermatitis, urticaria, angioneurotic edema, chronic obstructive pulmonary disease, asthma, tendonitis, bursitis, Crohn's disease, ulcerative colitis, autoimmune chronic active hepatitis, hepatitis, cinhosis, inflammatory scalp alopecia, panniculitis, psoriasis, inflamed cysts, pyoderma gangrenosum, pemphigus vulgaris, bullous pemphigoid, dermatomyositis, eosinophilic fasciitis, relapsing polychondritis, inflammatory vasculitis, sarcoidosis Sweet's disease, type 1 reactive leprosy, capillary hemangiomas, lichen planus, erythema nodosum acne, hirsutism, toxic epidermal necrolysis, erythema multiform, cutaneous T-cell lymphoma, psychoses, cognitive disorders (such as memory disturbances) mood disorders (such as depression and bipolar disorder), anxiety disorders and personality disorders.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As will be appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear.

In another aspect the present invention provides the use of a compound or formula (I), or a pharmaceutically acceptable salt thereof, for use in therapy (such as a therapy described above).

In yet another aspect the present invention provides the use of a compound or formula (I), or a pharmaceutically acceptable salt thereof, in the manufacture of a medicament for use in the treatment of a glucocorticoid receptor mediated disease state (such as a disease state described above).

In a further aspect the invention provides the use of a compound of formula (I), or a pharmaceutically acceptable salt thereof, in the manufacture of a medicament for use in the treatment of an inflammatory (such as an arthritic) condition.

In a still further aspect the invention provides the use of a compound of formula (I), or a pharmaceutically acceptable salt thereof, in the manufacture of a medicament for use in the treatment of an asthmatic condition.

In another aspect the invention provides the use of a compound of formula (I), or a pharmaceutically acceptable salt thereof, in the manufacture of a medicament for use in the treatment of COPD.

The present invention further provides a method of treating a glucocorticoid receptor mediated disease state, an inflammatory condition, an asthmatic condition and/or COPD, in a mammal (such as man), which comprises administering to a mammal in need of such treatment an effective amount of a compound of formula (I), or a pharmaceutically acceptable salt thereof.

In the context of the present specification, the term "therapy" also includes "prophylaxis" unless there are specific indications to the contrary. The terms "therapeutic" and "therapeutically" should be construed accordingly.

In this specification, unless stated otherwise, the terms "inhibitor" and "antagonist" mean a compound that by any means, partly or completely, blocks the transduction pathway leading to the production of a response by the agonist.

The term "disorder", unless stated otherwise, means any condition and disease associated with glucocorticoid receptor activity.

Pharmaceutical Composition

In order to use a compound of formula (I), or a pharmaceutically acceptable salt thereof, for the therapeutic treatment of a mammal, said active ingredient is normally formulated in accordance with standard pharmaceutical practice as a pharmaceutical composition.

Therefore in another aspect the present invention provides a pharmaceutical composition comprising a compound of formula (I), or a pharmaceutically acceptable salt thereof, (active ingredient) and a pharmaceutically acceptable adjuvant, diluent or carrier. In a further aspect the present invention provides a process for the preparation of said composition comprising mixing the active ingredient with a pharmaceutically acceptable adjuvant, diluent or carrier.

Depending on the mode of administration, the pharmaceutical composition can comprise from 0.05 to 99% w (per cent by weight), for example from 0.05 to 80% w, such as from 0.10 to 70% w (for example from 0.10 to 50% w), of active ingredient, all percentages by weight being based on total composition.

A pharmaceutical composition of the present invention can be administered in a standard manner for the disease condition that it is desired to treat, for example by topical (such as to the lung and/or airways or to the skin), oral, rectal or parenteral administration. Thus, a the compound of formula (I), or a pharmaceutically acceptable salt thereof, may be formulated into the form of, for example, an aerosol, a powder (for example dry or dispersible), a tablet, a capsule, a syrup, a granule, an aqueous or oily solution or suspension, an (lipid) emulsion, a suppository, an ointment, a cream, drops, or a sterile injectable aqueous or oily solution or suspension.

A suitable pharmaceutical composition of this invention is one suitable for oral administration in unit dosage form, for example a tablet or capsule containing between 0.1 mg and 1 g of active ingredient.

In another aspect a pharmaceutical composition of the invention is one suitable for intravenous, subcutaneous, intraarticular or intramuscular injection.

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. Tablets may be enteric coated by conventional means, for example to provide a coating of cellulose acetate phthalate.

The invention further relates to combination therapies or compositions wherein a GR agonist of formula (I), or a pharmaceutically acceptable salt thereof, or a pharmaceutical composition comprising a GR agonist of formula (I), or a pharmaceutically acceptable salt thereof, is administered concurrently (possibly in the same composition) or sequentially with one or more agents for the treatment of any of the above disease states.

For example, for the treatment of rheumatoid arthritis, osteoarthritis, COPD, asthma or allergic rhinitis a GR agonist of the invention can be combined with one or more agents for the treatment of such a condition. Where such a combination is to be administered by inhalation, then the one or more agents is selected from the list comprising:
- a PDE4 inhibitor including an inhibitor of the isoform PDE4D;
- a selective β.sub2. adrenoceptor agonist such as metaproterenol, isoproterenol, isoprenaline, albuterol, salbutamol, formoterol, salmeterol, terbutaline, orciprenaline, bitolterol mesylate, pirbuterol or indacaterol;
- a muscarinic receptor antagonist (for example a M1, M2 or M3 antagonist, such as a selective M3 antagonist) such as ipratropium bromide, tiotropium bromide, oxitropium bromide, pirenzepine or telenzepine;
- a steroid (such as budesonide);
- a modulator of chemokine receptor function (such as a CCR1 receptor antagonist); or,
- an inhibitor of p38 kinase function.

In another aspect of the invention where such a combination is for the treatment of COPD, asthma or allergic rhinitis the GR agonist of formula (I), or a pharmaceutically acceptable salt thereof, can be administered by inhalation or by the oral route and this is in combination with a xanthine (such as aminophylline or theophylline) which can be administered by inhalation or by the oral route.

EXAMPLES

The following Examples illustrate the invention. The following abbreviations are used in the Examples:

| | |
|---|---|
| TFA | Trifluoroacetic acid; |
| THF | Tetrahydrofuran |
| DCM | Dichloromethane |
| HPLC | High Performance Liquid Chromatography; |
| LC/MS | Liquid Column Chromatography/Mass Spectroscopy; |
| GC | Gas Chromatography |
| DMSO | Dimethylsulfoxide; |
| APCI-MS | Atmospheric Pressure Chemical Ionisation Mass Spectroscopy; |
| r.t. | Room temperature, which is a temperature in the range from of 16° C. to 25° C. |

General Methods

NMR spectra were recorded on a Varian Mercury-VX 300 MHz instrument or a Varian Inova 400 MHz instrument. The central peaks of chloroform-d (H 7.27 ppm), acetone (H 2.05 ppm), dichloromethane-d2 (H 5.32 ppm) or DMSO-$d_6$ (H 2.50 ppm) were used as internal references.

The following method was used for LC/MS analysis:

Instrument Agilent 1100; Column Waters Symmetry 2.1× 30 mm; Mass APCI; Flow rate 0.7 mL/min; Wavelength 254 nm; Solvent A: water+0.1% TFA; Solvent B: acetonitrile+ 0.1% TFA; Gradient 15-95%/B 2.7 min, 95% B 0.3 min.

The following method was used for GC-MS analysis:

Low resolution mass spectra and accurate mass determination were recorded on a Hewlett-Packard GC. MS system equipped with EI ionisation chamber, 70 eV.

The following method was used for LC analysis:

Method A. Instrument Agilent 1100; Column: Kromasil C18 100×3 mm, 5μ particle size, Solvent A: 0.1% TFA/water, Solvent B: 0.08% TFA/acetonitrile Flow: 1 mL/min, Gradient 10-100%/B 20 min, 100% B 1 min. Absorption was measured at 220, 254 and 280 nm.

A Kromasil KR-100-5-C18 column (250×20 mm, Akzo Nobel) and mixtures of acetonitrile/water (0.1% TFA) at a flow rate of 10 mL/min was used for preparative HPLC. Unless stated otherwise, starting materials were commercially available. All solvents and commercial reagents were of laboratory grade and were used as received.

Example 1

N-[(1R,2S)-1-[1-(4-fluorophenyl)indazol-5-yl]oxy-1-phenyl-propan-2-yl]cyclopropanesulfonamide

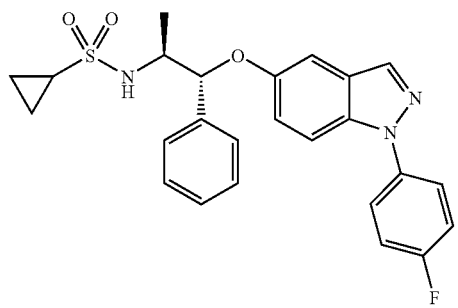

(1R,2S)-1-[1-(4-Fluorophenyl)indazol-5-yl]oxy-1-phenyl-propan-2-amine (1a, 16 mg, 0.044 mmole) was dissolved in dry pyridine (2 mL) and cooled to 0° C. Cyclopropanesulfonyl chloride (16 μl, 0.056 mmole) was added and the mixture was stirred at room temperature for 45 mm. The progression of the reaction was followed by HPLC (R.P C-18, 20-90% gradient of $CH_3CN$ in water, 0.1% TFA). After 45 and 75 mm additional portions of cyclopropanesulfonyl chloride (5 and 6 μl respectively) were added. As the reaction proceeded very slowly, triethylamine (27 μl, 0.2 mmol) was added after a total of 2.5 h of stirring. The stirring was continued at ambient temperature for additional 18.5h and the reaction mixture was then partitioned between ethyl acetate and aqueous hydrochloric acid (1.7M). The organic phase was washed twice with aqueous hydrochloric acid (1.7M), then with water and finally with brine. Evaporation and flash chromatography ($SiO_2$, gradient of 0-50% EtOAc in heptane) and finally lyophilization from dioxane gave the title compound (7 mg, 33%) containing 15 mol % of dioxane.

$^1$H-NMR (300 MHz, DMSO-$d_6$) δ 8.16 (1H, s), 7.76-7.73 (2H, m), 7.70 (1H, d), 7.44-7.34 (7H, m), 7.28 (1H, t, further coupled), 7.11 (1H, d) 7.24 (1H, dd), 5.33 (1H, d), 3.73 (1H, m), 2.39-2.33 (1H, m), 1.24 (3H, d), 0.89-0.79 (4H, m).

$^{19}$F-NMR (DMSO-$d_6$): –115.8 (tt, unresolved)

APCI-MS m/z: 466.0 [MH$^+$].

(1R,2S)-1-[1-(4-Fluorophenyl)indazol-5-yl]oxy-1-phenyl-propan-2-amine (1a)

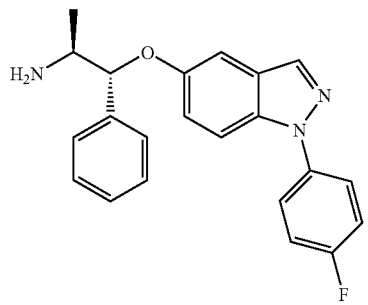

The sub-title compound was prepared essentially by a method described by Job & Buchwald: Org. Lett. 2002, 4 (21), 3703-3706.

1 (Fluorophenyl) 5 iodoindazole 1-(4-Fluorophenyl)-5-iodoindazole (43 mg, 0.12 mmole), (1R,2S)-norephedrine (16 mg, 0.1 mmol), copper (I) iodide (2.2 mg, 5 mol %) and cesium carbonate (84 mg, 0.26 mmole) were suspended in butyronitrile (1 ml). The reaction vessel was capped and the mixture was stirred at 125° C. The progress of the reaction was followed by HPLC (R.P C-18, 20-90% gradient of $CH_3CN$ in water, 0.1% TFA). After 7.5h additional (1R,2S)-norephedrine (70 mg), copper (I) iodide (16 mg) and cesium carbonate (136 mg) were added and the stirring was continued at 125° C. After 2h all 1-(4-fluorophenyl)-5-iodoindazole had been consumed and the mixture was cooled, filtered and evaporated. Flash chromatography ($SiO_2$, gradient of 0-30% MeOH in EtOAc) gave the sub-title compound (19 mg, 41%).

$^1$H-NMR (300 MHz, DMSO-$d_6$+$D_2O$, TFA added) δ 8.16 (1H, d), 7.76-7.68 (3H, m), 7.43-7.28 (8H, m), 7.12 (1H, d), 5.64 (1H, d), 3.70 (1H, qd), 1.16 (3H, d).

$^{19}$F-NMR (DMSO-$d_6$): δ-115.97 (tt, unresolved).

APCI-MS m/z: 362.2 [MH$^+$].

Example 2

N-[(1R,2S)-1-[1-(4-fluorophenyl)indazol-5-yl]oxy-1-phenyl-propan-2-yl]propane-1-sulfonamide

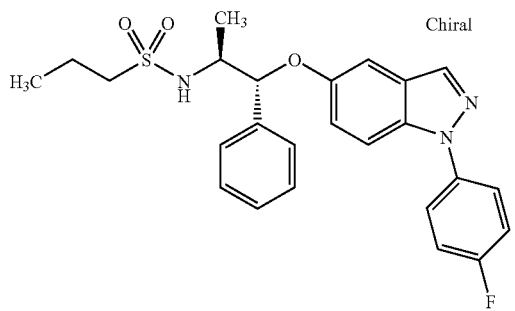

To a stirred solution of (1R,2S)-1-[1-(4-fluorophenyl)indazol-5-yl]oxy-1-phenyl-propan-2-amine (1a, 18 mg, 50 μmol) in acetonitrile (1 ml) was added triethylamine (100 μl), followed by propane-1-sulfonyl chloride (21 mg, 150 μmol). Stirring was continued overnight. The mixture was then diluted with water (300 μl), and the title compound isolated by preparative HPLC to afford 23 mg (83%) as white solid.

$^1$H NMR (400 MHz, $d_6$-acetone) δ 8.04 (d, J=0.7 Hz, 1H), 7.77 (m, 2H), 7.71 (d, J=9.2 Hz, 1H), 7.49 (d, J=7.3 Hz, 2H), 7.41-7.29 (m, 5H), 7.27 (dd, J=9.1, 2.4 Hz, 1H), 7.16 (d, J=2.3 Hz, 1H), 6.25 (d, J=9.0 Hz, 1H), 5.47 (d, J=4.2 Hz, 1H), 3.89 (m, 1h), 2.86 (m, 2H), 1.67 (m, 2H), 1.33 (d, J=6.7 Hz, 3H), 0.92 (t, J=7.

APCI-MS m/z: 468 [MH$^+$]

Example 3

N-[(1R,2S)-1-[1-(4-fluorophenyl)indazol-4-yl]oxy-1-phenyl-propan-2-yl]cyclopropanesulfonamide

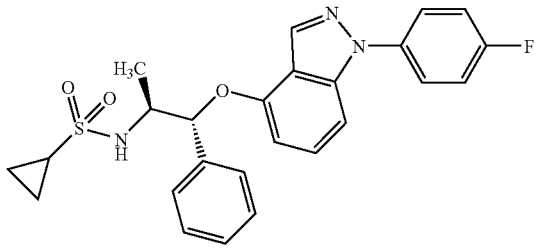

Prepared according the protocol described for Example 1 using (1R,2S)-1-[1-(4-fluorophenyl)indazol-4-yl]oxy-1-phenyl-propan-2-amine (3a, 30 mg, 0.08 mmol) and cyclopropylsulphonyl chloride (22 μl, 0.21 mmol). Yield: 20 mg (53%).

$^1$H NMR (400 MHz, DMSO-$d_6$) δ 8.51 (s, 1H), 7.77 (td, J=8.7, 3.8 Hz, 2H), 7.49 (d, J=8.5 Hz, 1H), 7.44-7.35 (m, 6H), 7.31-7.20 (m, 3H), 6.40 (d, J=6.9 Hz, 1H), 5.50 (d, J=4.4 Hz, 1H), 3.85-3.77 (m, 1H), 2.43-2.35 (m, 1H), 1.31 (d, J=6.7 Hz, 3H), 0.90-0.79 (m, 4H).

APCI-MS: 466 m/z [MH$^+$]

(1R,2S)-1-[1-(4-Fluorophenyl)indazol-4-yl]oxy-1-phenyl-propan-2-amine (3a)

Prepared according to the protocol described for 1a starting from 4-iodo-1-(4-fluorophenyl)indazole (3b, 332 mg, 0.98 mmol) and (1R,2S)-norephedrine (742 mg, 4.9 mmol). Yield: 150 mg (42%).

APCI-MS: 362 m/z [MH+]

4-Iodo-1-(4-fluorophenyl)indazole (3b)

4-Bromo-1-(4-fluorophenyl)indazole (291 mg, 1 mmol), copper(I)iodide (9.5 mg, 0.05 mmol), sodium iodide (300 mg, 2 mmol) and (1R,2R)—(N,N'-dimethylcyclohexane-1,2-diamine (14.2 mg, 0.1 mmol) in dioxane (1 ml) were mixed and stirred in argon at 110° C. All starting material was consumed after 24 h. The mixture was cooled and ammonia (5 ml, 28% in water) and water (20 ml) were added followed by extraction with DCM (2×15 ml). The organic phase was concentrated and the crude product was purified by flash chromatography (EtOAc/Heptane) to give the title compound (322 mg, 98%).

APCI-MS m/z: 339 [MH+].

Example 4

N-[(1R,2S)-1-[1-(6-fluoropyridin-3-yl)indazol-5-yl]oxy-1-phenyl-propan-2-yl]cyclopropanesulfonamide

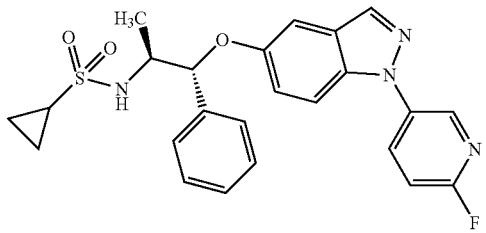

Prepared according the protocol described for Example 1 using 1-[1-(6-fluoro-1-pyridin-3-yl)indazol-5-yl]oxy-1-phenyl-propan-2-amine (20 mg, 0.06 mmol) and cyclopropylsulphone chloride (18 µl, 0.17 mmol). Yield: 5 mg (71%).

$^1$H NMR (400 MHz, DMSO-$d_6$) δ 8.63 (s, 1H), 8.36 (ddd, J=9.1, 6.8, 2.6 Hz, 1H), 8.24 (s, 1H), 7.78 (d, J=9.2 Hz, 1H), 7.45-7.34 (m, 6H), 7.30-7.25 (m, 2H), 7.14 (d, J=2.3 Hz, 1H), 5.34 (d, J=4.4 Hz, 1H), 3.76-3.70 (m, 1H), 2.40-2.31 (m, 1H), 1.24 (d, J=6.9 Hz, 3H), 0.88-0.80 (m, 4H)

APCI-MS: 466 m/z [MH+]

1-[1-(6-fluoro-1-pyridin-3-yl)indazol-5-yl]oxy-1-phenyl-propan-2-amine (4b)

4-Iodo-1-(6-fluoro-1-pyridin-3-yl)indazole (4c, 191 mg, 0.56 mmol), (1R,2S)-norephedrine (426 mg, 2.8 mmol), copper(I)iodide (139 mg, 0.73 mmol) and cesium carbonate (1.8 g, 5.6 mmol) in butyronitrile (3 ml) were mixed and stirred in argon at 125° C. for 2 h. The starting material was consumed according to LC-MS. The crude mixture was purified by flash chromatography (EtOAc/heptane/methanol) followed by preparative HPLC (MeCN/water/1% TFA) to obtain the title compound (20 mg, 10%).

APCI-MS m/z: 363 [MH+].

4-Iodo-1-(6-fluoro-1-pyridin-3-yl)indazole (4c)

4-Bromo-1-(6-fluoro-1-pyridin-3-yl)indazole (184 mg, 0.63 mmol), sodium iodide (189 mg, 1.26 mmol), copper(I) iodide (6 mg, 0.03 mmol) and (1R,2R)—(N,N'-dimethylcyclohexane-1,2-diamine (8.5 mg, 0.06 mmol) in dioxane (1 ml) were mixed and stirred at 110° C. in argon. Ammonia (5 ml, 28% in water) and water (20 ml) were added and the mixture was extracted with 2×15 ml DCM. The organic phase was concentrated and the crude product was purified by flash chromatography (EtOAc/heptane) to give the title compound (191 mg, 89%).

APCI-MS m/z: 340 [MH+].

Example 5

N-[(1R,2S)-1-[1-(4-fluorophenyl)indazol-5-yl]oxy-1-phenyl-propan-2-yl]methanesulfonamide

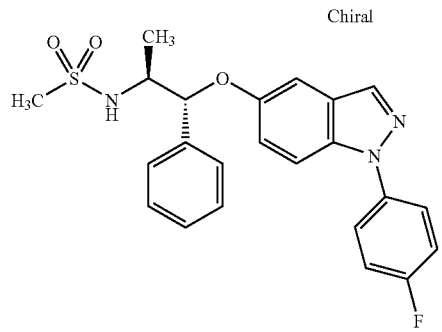

Prepared and purified using the procedure described in Example 2. Yield 11 mg.

APCI-MS m/z: 440 [MH+]

Example 6

N-[(1R,2S)-1-[1-(4-fluorophenyl)indazol-5-yl]oxy-1-phenyl-propan-2-yl]-1-phenyl-methanesulfonamide

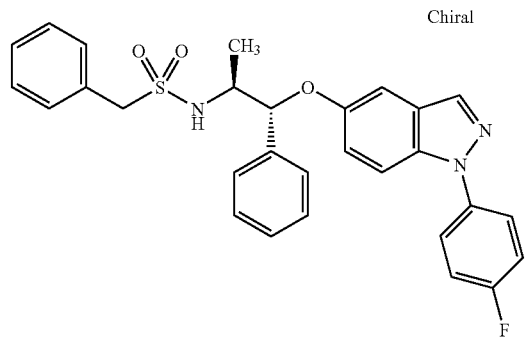

Prepared and purified using the procedure described in Example 2. Yield 5.7 mg.

APCI-MS m/z: 516 [MH+]

Example 7

1,1,1-trifluoro-N-[(1R,2S)-1-[1-(4-fluorophenyl)indazol-5-yl]oxy-1-phenyl-propan-2-yl]methanesulfonamide

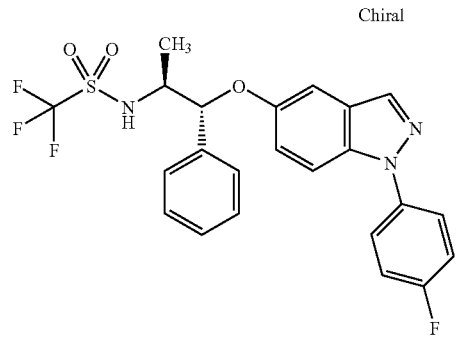

Prepared and purified using the procedure described in Example 2. Yield 9.5 mg.
APCI-MS m/z: 494 [MH+]

Example 8

5-[(1R,2S)-2-(dimethylsulfamoylamino)-1-phenylpropoxy]-1-(4-fluorophenyl)indazole

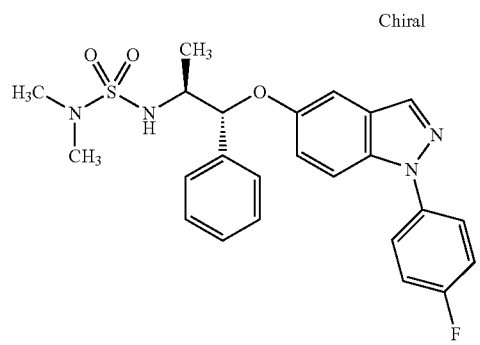

Prepared and purified using the procedure described in Example 2. Yield 12.3 mg.
APCI-MS m/z: 469 [MH+]

Example 9

N-[(1R,2S)-1-[1-(4-fluorophenyl)indazol-5-yl]oxy-1-phenyl-propan-2-yl]propane-2-sulfonamide

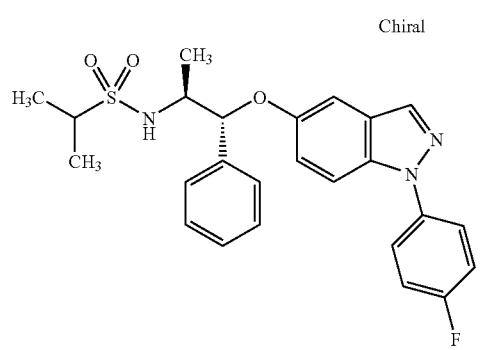

Prepared and purified using the procedure described in Example 2. Yield 1.2 mg.
APCI-MS m/z: 468 [MH+]

Example 10

2-(1,3-Dioxoisoindol-2-yl)-N-[(1R,2S)-1-[1-(4-fluorophenyl)indazol-5-yl]oxy-1-phenyl-propan-2-yl]ethanesulfonamide

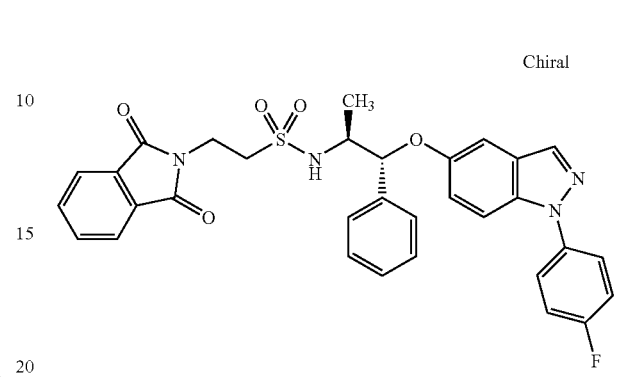

Prepared and purified using the procedure described in Example 2. Yield 2.8 mg.
APCI-MS m/z: 599 [MH+]

Example 11

N-[(1R,2S)-1-[1-(4-fluorophenyl)indazol-5-yl]oxy-1-phenyl-propan-2-yl]-3-(4-methoxyphenoxy)propane-1-sulfonamide

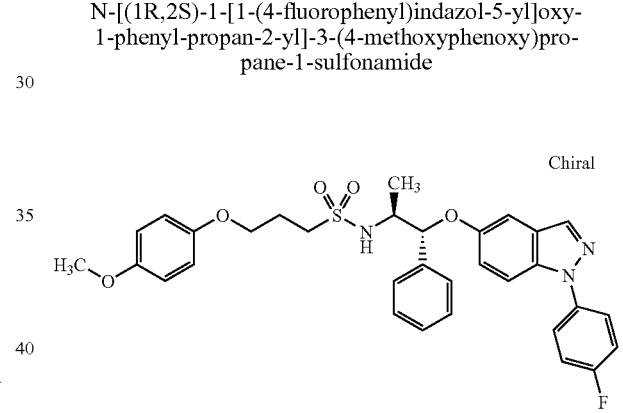

Prepared and purified using the procedure described in Example 2. Yield 11.3 mg.
APCI-MS m/z: 590 [MH+]

Example 12

N-[(1R,2S)-1-[1-(4-fluorophenyl)indazol-5-yl]oxy-1-phenyl-propan-2-yl]ethanesulfonamide

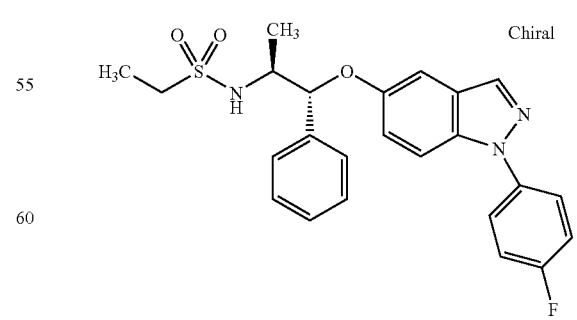

Prepared and purified using the procedure described in Example 2. Yield 10.6 mg.
APCI-MS m/z: 454 [MH+]

Example 13

N-[(1R,2S)-1-[1-(4-fluorophenyl)indazol-5-yl]oxy-J-phenyl-propan-2-yl]pentane-2-sulfonamide

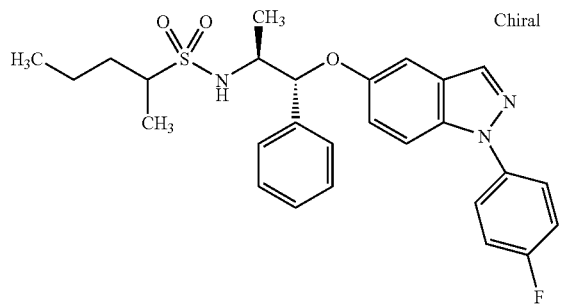

Prepared and purified using the procedure described in Example 2. Yield 0.4 mg.
APCI-MS m/z: 496 [MH+]

Example 14

N-[(1R,2S)-1-[1-(4-fluorophenyl)indazol-5-yl]oxy-1-phenyl-propan-2-yl]butane-2-sulfonamide

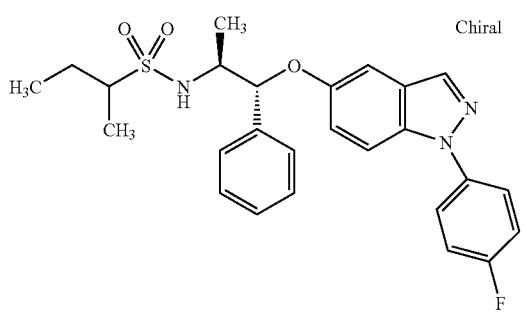

Prepared and purified using the procedure described in Example 2. Yield 0.9 mg.
APCI-MS m/z: 482 [MH+]

Example 15

N-[(1R,2S)-1-[1-(4-fluorophenyl)indazol-5-yl]oxy-1-phenyl-propan-2-yl]butane-1-sulfonamide

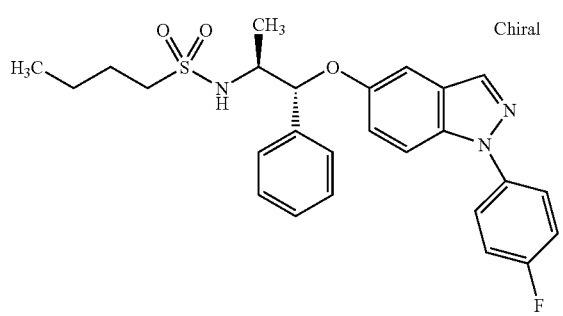

Prepared and purified using the procedure described in Example 2. Yield 1.2 mg.
APCI-MS m/z: 482 [MH+]

Example 16

N-[(1R,2S)-1-[1-(4-fluorophenyl)indazol-5-yl]oxy-1-phenyl-propan-2-yl]-2-methyl-propane-1-sulfonamide

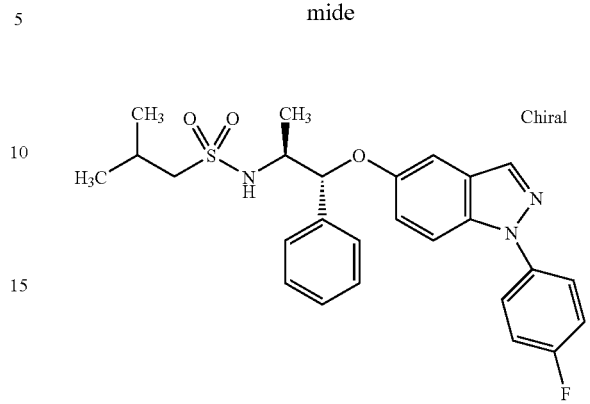

Prepared and purified using the procedure described in Example 2. Yield 7.2 mg.
APCI-MS m/z: 482 [MH+]

Example 17

N-[(1R,2S)-1-[1-(4-fluorophenyl)indazol-5-yl]oxy-1-phenyl-propan-2-yl]pentane-1-sulfonamide

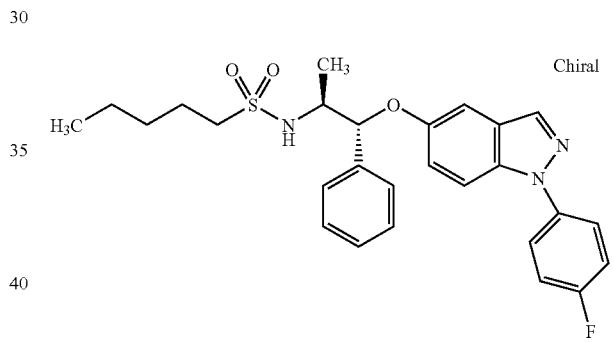

Prepared and purified using the procedure described in Example 2. Yield 8.8 mg.
APCI-MS m/z: 496 [MH+]

Example 18

3,3,3-trifluoro-N-[(1R,2S)-1-[1-(4-fluorophenyl)indazol-5-yl]oxy-1-phenyl-propan-2-yl]propane-1-sulfonamide

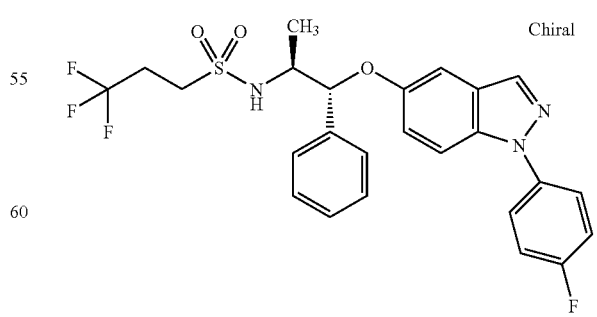

Prepared and purified using the procedure described in Example 2. Yield 16.4 mg.
APCI-MS m/z: 522 [MH+]

Example 19

Methyl 3-[[(1R,2S)-1-[1-(4-fluorophenyl)indazol-5-yl]oxy-1-phenyl-propan-2-yl]sulfamoyl]propanoate

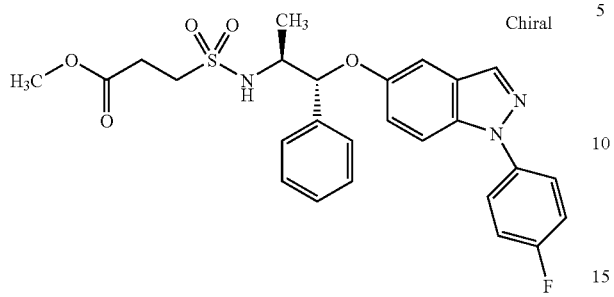

Prepared and purified using the procedure described in Example 2. Yield 8 mg.
APCI-MS m/z: 512 [MH$^+$]

Example 20

1-Cyclopentyl-N-[(1R,2S)-1-[1-(4-fluorophenyl)indazol-5-yl]oxy-1-phenyl-propan-2-yl]methanesulfonamide

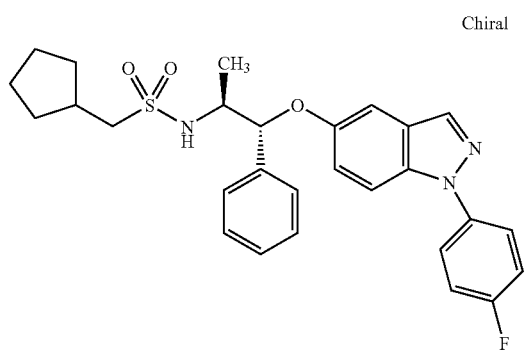

Prepared and purified using the procedure described in Example 2. Yield 9.1 mg.
APCI-MS m/z: 508 [MH$^+$]

Example 21

N-[(1R,2S)-1-[1-(4-fluorophenyl)indazol-5-yl]oxy-1-phenyl-propan-2-yl]cyclopentanesulfonamide

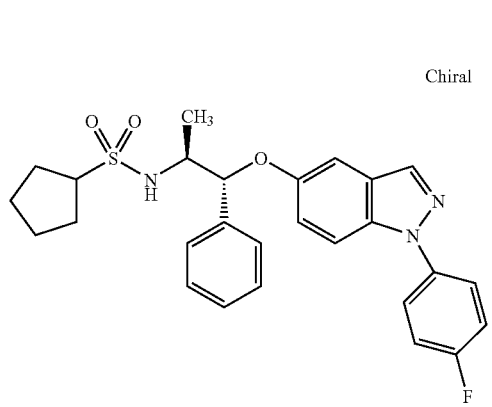

Prepared and purified using the procedure described in Example 2. Yield 0.7 mg.
APCI-MS m/z: 494 [MH$^+$]

Example 22

2,2,2-trifluoro-N-[(1R,2S)-1-[1-(4-fluorophenyl)indazol-5-yl]oxy-1-phenyl-propan-2-yl]ethanesulfonamide

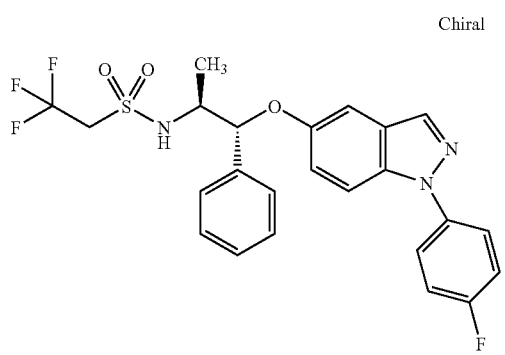

Prepared and purified using the procedure described in Example 2. Yield 6.7 mg.
APCI-MS m/z: 508 [MH$^+$]

Example 23

1-Cyclohexyl-N-[(1R,2S)-1-[1-(4-fluorophenyl)indazol-5-yl]oxy-1-phenyl-propan-2-yl]methanesulfonamide

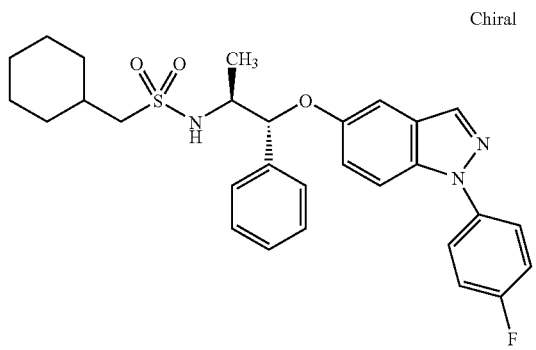

Prepared and purified using the procedure described in Example 2. Yield 5.6 mg.
APCI-MS m/z: 522 [MH$^+$]

Example 24

N-[(1R,2S)-1-[1-(4-fluorophenyl)indazol-5-yl]oxy-1-phenyl-propan-2-yl]hexane-1-sulfonamide

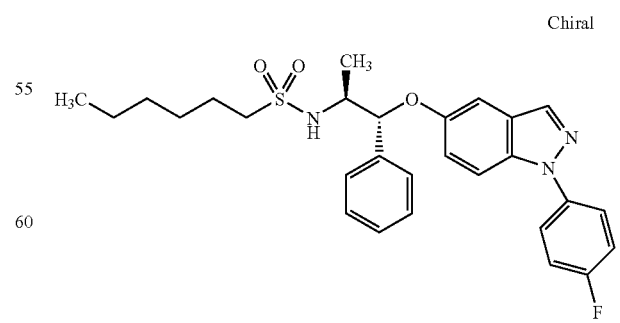

Prepared and purified using the procedure described in Example 2. Yield 5.3 mg.
APCI-MS m/z: 510 [MH$^+$]

Example 25

N-[(1R,2S)-1-[1-(4-fluorophenyl)indazol-5-yl]oxy-1-phenyl-propan-2-yl]pyridine-3-sulfonamide

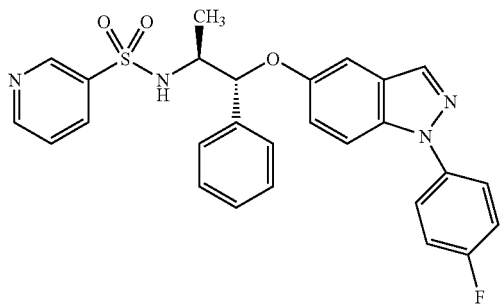

Prepared and purified using the procedure described in Example 2. Yield 18.6 mg.
APCI-MS m/z: 503 [MH$^+$]

Example 26

(R)—N-(2-methyl-1-phenyl-1-(1-(4-fluorophenyl)-1H-indazol-5-yloxy)propan-2-yl)cyclopropane-sulfonamide

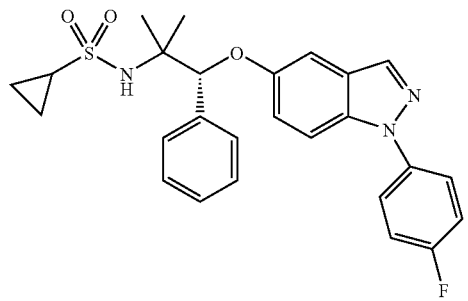

The racemic mixture of N-(1-(1-(4-Fluorophenyl)-1H-indazol-5-yloxy)-2-methyl-1-phenylpropan-2-yl)cyclopropanesulfonamide (26-rac, 10 mg) was separated on Thales SFC, Chiralpak IA column(70% CO$_2$, 20% MeOH) collecting the first eluating peak.
Yield: 4 mg (40%)
APCI-MS: m/z 468 [MH$^+$]
Chiral analysis was made using a CHIRALPAK® IB, 150×0.46 mm column, 10% MeOH/90% CO$_2$, 3.5 mL/min, UV=254 nm: >98% ee, Rt=9.0 min.

(RS)—N-(2-methyl-1-phenyl-1-(1-(4-fluorophenyl)-1H-indazol-5-yloxy)propan-2-yl)cyclopropane-sulfonamide (26-rac)

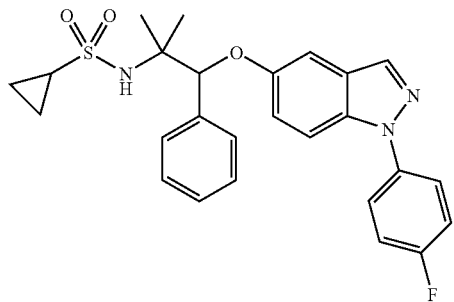

Cyclopropanesulfonyl chloride (155 µl, 1.52 mmol) was added to 1-(1-(4-fluorophenyl)-1H-indazol-5-yloxy)-2-methyl-1-phenylpropan-2-amine (26a, 0.070 g, 0.19 mmol) triethylamine (80 µl, 0.57 mmol) in MeCN (3 ml) at room temperature. The reaction mixture was stirred over night, concentrated, diluted with 10% NaHSO$_4$ (aq) and extracted with EtOAc. The organic phase was washed with 10% NaHSO$_4$ (aq). The crude product was further purified by HPLC. Yield 25 mg (30%).
$^1$H NMR (400 MHz, DMSO-d6) δ 8.15 (s, 1H), 7.73 (dd, J=9.0, 4.8 Hz, 2H), 7.67 (d, J=9.2 Hz, 1H), 7.48 (d, J=7.3 Hz, 2H), 7.37 (m, 4H), 7.25 (m, 2H), 7.05 (d, J=2.3 Hz, 1H), 7.00 (s, 1H), 5.46 (s, 1H), 2.56 (m, 1H), 1.46 (s, 3H), 1.27 (s, 3H), 0.89 (m, 4H),
APCI-MS: m/z 480.2 [MH$^+$]

1-(1-(4-Fluorophenyl)-1H-indazol-5-yloxy)-2-methyl-1-phenylpropan-2-amine (26a)

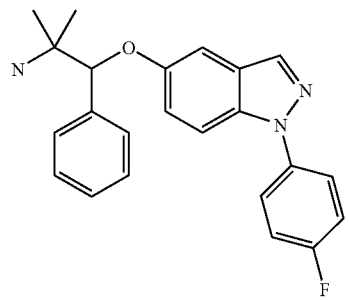

The subtitle compound was prepared essentially by the method described by Job & Buchwald: Org. Lett. 2002, 4 (21), 3703-3706.
A mixture of 2-amino-2-methyl-1-phenylpropan-1-ol (26b, 231 mg, 1.39 mmol), 1-(4-Fluorophenyl)-5-iodo-1H-indazole (47 mg, 1.39 mmol), copper(I) iodide (38.1 mg, 0.20 mmol) and Cs$_2$CO$_3$ (1.3 g, 4.20 mmol) in butyronitrile (20 mL) was heated for 5 hours at 100° C. in a sealed vial flushed with Argon. The reaction mixture was cooled down, partitioned between EtOAc (20 mL) and water (5 mL), the organic phase was washed with brine. The crude product was purified on HPLC Yield 70 mg (14%).
APCI-MS: m/z 376.2 [MH$^+$]

2-Amino-2-methyl-1-phenylpropan-1-ol (26b)

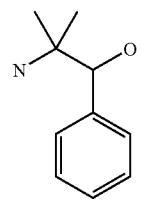

37% Hydrochloric acid (1 mL) was added to a stirred solution of 2-methyl-2-nitro-1-phenylpropan-1-ol (26c, 0.12 g, 0.6 mmol in EtOH (10 mL) and water (5 mL). Zinc powder (0.241 g, 3.6 mmol) was slowly added in small portions, the mixture was stirred for 4 hours at +70° C. The mixture was filtered to remove solid zinc residues and concentrated to ⅓ volume by evaporation, diluted with water (50 mL) and washed with ether (125 mL). The acidic waterphase was made basic using KOH (aq) solution, the formed slurry was extracted with ether (3×150 mL). The organic phase was dried (MgSO₄) filtered and evaporated. The crude product was further purified by HPLC. Yield 60 mg (60%).

¹H NMR (400 MHz, DMSO-d6) δ 7.27 (m, 5H), 6.14 (s, 1H), 5.47 (d, J=4.8 Hz, 1H), 4.90 (s, 1H), 1.26 (s, 3H), 1.00 (s, 3H).

APCI-MS: m/z 164 [MH⁺]

2-Methyl-2-nitro-1-phenylpropan-1-ol (26c)

To a round bottom flask was added anhyrous magnesium sulphate (3.5 g, 29 mmol) And 2-nitropropane (16 ml). The flask was evacuated and filled with argon. The reaction mixture was stirred vigorously to get a homogeneous suspension before benzaldehyde (1.3 ml, 13.1 mmol) was added. After stirring in 5 min 2,5,8,9-tetraaza-1-phosphabicyclo[3.3.3]undecane,2,8,9-tris(1-methylethyl) (395 mg, 1.3 mmol) was added. The reaction mixture was stirred overnight at room temperature before it was purified by flash chromatography (SiO₂, heptane-ethylacetate). Yield 0.8 g (30%).

¹H NMR (300 MHz, DMSO-d6) δ 7.35 (m, 5H), 6.07 (d, J=4.5 Hz, 1H), 5.08 (d, J=4.4 Hz, 1H), 1.39 (s, 3H), 1.33 (s, 3H).

APCI-MS: m/z 376.2 [MH⁺]

Example 27

N-[(1RS,2SR)-1-[1-(4-fluorophenyl)indazol-5-yl]oxy-1-(4-methylsulfanylphenyl)propan-2-yl]cyclopropanesulfonamide

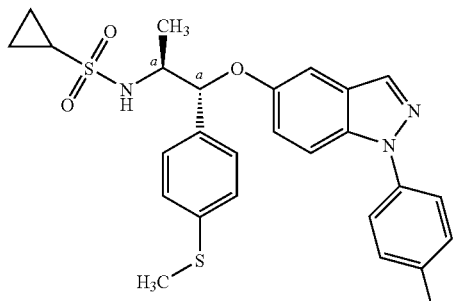

a = relative mixture

The racemic mixture of (1RS,2SR)-1-{[1-(4-fluorophenyl)-1H-indazol-5-yl]oxy}-1-[4-(methylthio)phenyl]propan-2-amine (27a, 11 mg, 0.02 mmol) was dissolved in THF (1.5 mL). Excess N-ethyldiisopropylamine (0.185 mL, 1.1 mmol) and cyclopropanesulfonyl chloride (0.063 mL, 0.62 mmol) was added in portions over a period of 3 hours. The reaction mixture was stirred over night at room temperature, quenched by addition of water and purified by HPLC. Fractions with product was freeze dried to give the title compound as a colourless solid. Chiral HPLC was made using an Chiralpak IB™, 150×0.46 mm column, 15% EtOH in iso-Hexane, 0.5 mL/min, UV=254 nm. two peaks was seen in 1:1 ratio.

Yield 6 mg (58%)

Chiral HPLC:two peaks, 1:1 ratio, Rt=30.64+32.92 min.

¹H-NMR (300 MHz, DMSO-d₆): δ 8.16 (d, 1H), 7.78-7.66 (m, 3H), 7.44-7.30 (m, 5H), 7.28-7.19 (m, 3H), 7.11 (d, 1H), 5.28 (d, J=4.38 Hz, 1H), 3.71 (m, 1H), 2.44 (s, 3H), 2.42 (m, 1H), 1.24 (d, J=6.76 Hz, 3H), 0.90-0.80 (m, 4H)

APCI-MS m/z: 512.1 [MH⁺].

(1RS,2SR)-1-{[1-(4-fluorophenyl)-1H-indazol-5-yl]oxy}-1-[4-(methylthio)phenyl]propan-2-amine (27a)

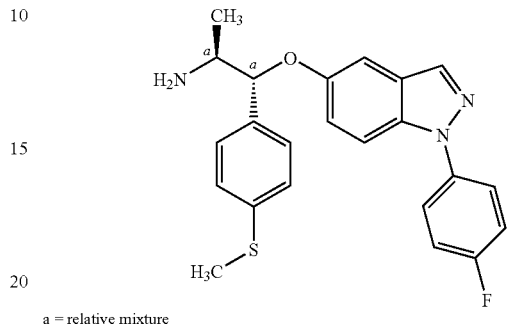

a = relative mixture

The racemic subtitle compound was prepared as described in Example 1a

Starting from racemic (1RS,2SR)-2-amino-1-[4-(methylthio)phenyl]propan-1-ol (49 mg 0.25 mmol), 1-(4-Fluorophenyl)-5-iodoindazole (27b-erythro, 100 mg, 0.3 mmol), CuI (5 mg, 0.03 mmol), Cs₂CO₃ (163 mg, 0.5 mmol) in butyronitrile (0.5 mL) at +125° C. over night. After work up and purification by HPLC the subtitle compound was isolated as the trifluoroacetic acid salt, no NMR was run on this material, LC/MS was used for identification and all obtained material was used directly in next step. Yield 11 mg (8%)

APCI-MS m/z: 408.1 [MH⁺-TFA]

(1RS,2SR)-2-amino-1-[4-(methylthio)phenyl]propan-1-ol & (1R*,2R*)-2-amino-1-[4-(methylthio)phenyl]propan-1-ol (27b-erythro)

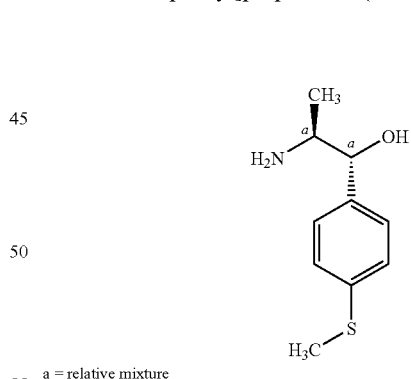

a = relative mixture

37% Hydrochloric acid (13 mL, 166 mmol) was added to a stirred solution of 1-[4-(methylthio)phenyl]-2-nitropropane-1-ol (2.14 g, 9.41 mmol) in EtOH (60 mL) and water (30 mL). Zinc powder (3.7 g, 56.6 mmol) was slowly added in small portions, the mixture was stirred for 4 hours at +70° C. The mixture was filtered to remove solid zinc residues and concentrated to ⅓ volume by evaporation, diluted with water (50 mL) and washed with ether (125 mL). The acidic waterphase was made basic using KOH (aq) solution, the formed slurry was extracted with ether (3×150 mL). The organic phase was dried (MgSO₄) filtered and evaporated. The crude product was further purified and separated into its two racemic diastereomeric pairs by HPLC.

A small sample of each pair was dissolved in DCM/THF and treated with 1 mol eq 1-1'-carbonyldiimidazole and cyclizised to the corresponding oxazolidinone that was isolated and analysed by NMR. By comparing shifts and coupling constants with literature values of oxazolidinones prepared from norephedrines with known stereochemistry (*Tetrahedron assym*, 1993, vol 4. no 12, pp 2513-2516 & *Org. lett*, 2005, 7, 13, 2755-2758), the relative stereochemistry of the obtained racemates was determined.

Purity analysis of the subtitle compound was made using an Xterra® C18, 5 um, 3.0×100 mm column, 20 min gradient of 10% MeCN in 15 mM NH₃/water to 100% MeCN, 1 mL/min, UV=254 nm.

Obtained racemic subtitle compound 27b-erythro:

Yield 243 mg (13%)

HPLC : Rt=3.9 min. 99.3% d.e.

APCI-MS m/z: 198.2 [MH⁺].

¹H-NMR (300 MHz, DMSO-d6): δ 7.22 (m, 4H), 5.14 (vbrs, 1H, —OH), 4.28 (d, J=4.78 Hz, 1H), 3.26 (vbrs, 3.3H —NH₂+water), 2.86 (brm, 1H), 2.45 (s, 3H), 0.84 (d, J=6.37 Hz, 1H)

The above material cyclizised to corresponding racemic oxazolidinone: (4R*,5S*)-4-methyl-5-[4-(methylthio)phenyl]-1,3-oxazolidin-2-one.

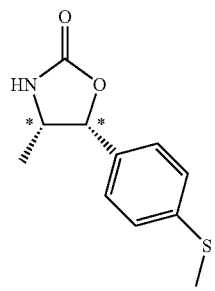

HPLC:Rt=6.27 min. 100% d.e.

APCI-MS m/z: 223.9 [MH⁺].

¹H-NMR (300 MHz, CDCl₃): δ 7.25 (m, 4H), 5.68 (d, J=7.83 Hz, 1H), 5.45 (brs, 1H), 4.19 (m, 1H), 2.51 (s, 3H), 0.83 (d, J=6.63 Hz, 3H).

(1RS,2RS)-2-amino-1-[4-(methylthio)phenyl]propan-1-ol (27b-threo)

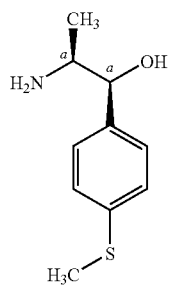

a = relative mixture

Isolated as the secondly eluated isomer by the separation of the diastereomers of 2-amino-1-[4-(methylthio)phenyl]propan-1-ol as described for 27b-erythro. Yield 418 mg (22%)

HPLC:Rt=4.5 min. 96.4% d.e.

APCI-MS m/z: 198.2 [MH⁺].

¹H-NMR (300 MHz, DMSO-d6): δ 7.21 (m, 4H), 5.22 (vbrs, 1H, —OH), 4.07 (brd, 1H), 2.75 (brm, 1H), 2.45 (s, 3H), 1.51 (vbrs, 2H, —NH2), 0.76 (brd, 3H)

The above material cyclizised to corresponding racemic oxazolidinone: (4R*,5R*)-4-methyl-5-[4-(methylthio)phenyl]-1,3-oxazolidin-2-one.

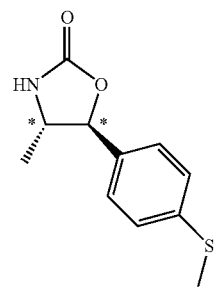

HPLC:Rt=6.41 min. 100% d.e.

APCI-MS m/z: 224.0 [MH⁺].

¹H-NMR (300 MHz, CDCl₃): δ 7.29 (m, 4H), 5.59 (brs, 1H), 5.01 (d, J=7.43 Hz, 1H), 3.82 (m, 1H), 2.50 (s, 3H), 1.38 (d, J=6.11 Hz, 3H)

1-[4-(methylthio)phenyl]-2-nitropropane-1-ol (27c)

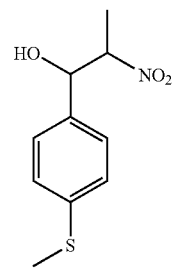

2,8,9-Triisopropyl-2,5,8,9-tetraaza-1-phosphabicyclo-[3.3.3]undecane (395 mg, 1.3 mmol) in Nitroethane (8 mL) was added to a stirred suspension of waterfree MgSO₄ (3.5 g) and 4-(methylthio)bensaldehyde (2 g, 13.1 mmol) in Nitroethane (8 mL) at room temperature. The yellow slurry was stirred over night, diluted with ether and filtered through a short silica plug that was washed with ether. Solvents was removed by evaporation and the crude product was purified by flash chromatography using a gradient of 0% EtOAc to 30% EtOAc in Heptane. The product was obtained as an oil that crystallised upon standing. LC/MS and GC/MS failed to give any m/z corresponding to desired mass. NMR supported structure and showed a diastereomeric mixture of 10:19. Yield 2.4 g (81%)

¹H-NMR (300 MHz, CDCl₃): δ 7.29 (m, 4H), 5.36 (d, J=3.74 Hz, 0.35H), 5.00 (d, J=9 Hz, 0.65H), 4.81-4.63 (m, 1H), 2.51+2.50 (s+s, total 3H), 2.39 (vbrs, 1H), 1.52 (d, J=6.84 Hz, 1.02H), 1.33 (d, J=6.84 Hz, 1.98H)

Example 28

N-[(1RS,2RS)-1-[1-(4-fluorophenyl)indazol-5-yl]oxy-1-(4-methylsufanylphenyl)propan-2-yl]cyclopropanesulfonamide

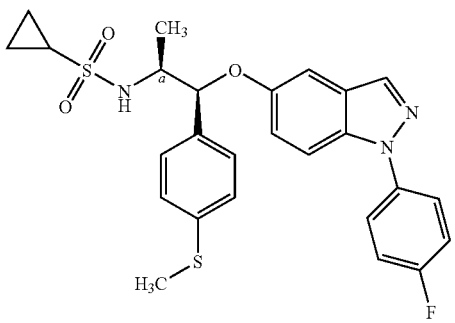

a = relative mixture

The racemic mixture of (1RS,2RS)-1-{[1-(4-fluorophenyl)-1H-indazol-5-yl]oxy}-1-[4-(methylthio)phenyl]propan-2-amine (28a, 32 mg, 0.06 mmol) was dissolved in THF (2 mL). Excess N-ethyldiisopropylamine (0.285 mL, 1.7 mmol) and cyclopropanesulfonyl chloride (0.069 mL, 0.68 mmol) was added in portions over a period of 3 hours. The reaction mixture was stirred over night at room temperature, quenched by addition of water and purified by HPLC. Fractions with product was freeze dried to give the title compound as a colourless solid. Chiral HPLC was made using an Chiralpak IB™, 150×0.46 mm column, 15% EtOH in iso-Hexane, 0.5 mL/min, UV=254nm. two peaks was seen in 1:1 ratio. Yield 9 mg (29%)

Chiral HPLC:two peaks, 1:1 ratio, Rt=30.07+35.59 min.

$^1$H-NMR (300 MHz, DMSO-$d_6$): δ 8.16 (d, 1H), 7.78-7.64 (m, 3H), 7.44-7.34 (m, 4H), 7.30-7.13 (m, 5H), 5.25 (d, J=5.57 Hz, 1H), 3.80 (m, 1H), 2.48 (m, 1H), 2.43 (s, 3H), 1.14 (d, J=6.77 Hz, 3H), 0.90-0.81 (m, 4H).

APCI-MS m/z: 512.1 [MH$^+$].

(1RS,2RS)-1-{[1-(4-fluorophenyl)-1H-indazol-5-yl]oxy}-1-[4-(methylthio)phenyl]propan-2-amine (28a)

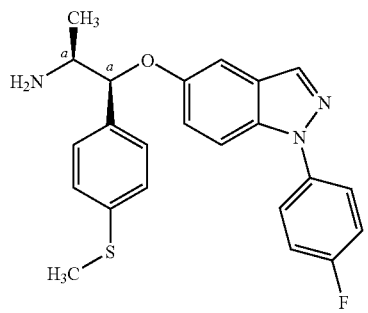

a = relative mixture

The racemic subtitle compound was prepared as described in Example 1.

Starting from racemic (1RS,2RS)-2-amino-1-[4-(methylthio)phenyl]propan-1-ol (27b-threo, 46 mg 0.23 mmol), 1-(4-Fluorophenyl)-5-iodoindazole (95 mg, 0.28 mmol), CuI (5 mg, 0.03 mmol), Cs$_2$CO$_3$ (163 mg, 0.5 mmol) in butyronitrile (0.5 mL) at +125° C. over night. After work up and purification by HPLC the subtitle compound was isolated as the Trifluoroacetic acid salt, no NMR was run on this material, LC/MS was used for identification and all obtained material was used directly in next step. Yield 32 mg (26%)

APCI-MS m/z: 408.2 [MH$^+$-TFA]

Example 29

N-[(1R,2S)-1-[1-(4-fluorophenyl)indazol-5-yl]oxy-1-(4-methylsulfanylphenyl)propan-2-yl]cyclopropanesulfonamide

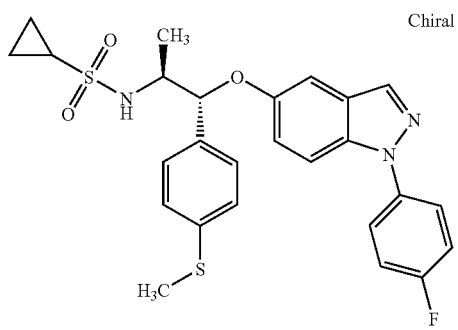

(1R,2S)-1-{[1-(4-fluorophenyl)-1H-indazol-5-yl]oxy}-1-[4-(methylthio)phenyl]propan-2-amine (29a, 100 mg, 0.24 mmol) was dissolved in MeCN (3 mL), triethylamine (0.104 mL, 0.75 mmol) was added followed by addition of cyclopropane sulfonylchloride (0.025 mL, 0.25 mmol). The reaction was followed by LC/MS. After 1 hour approximately 50% conversion was detected, more reagents cyclopropane sulfonylchloride (0.025 mL, 0.25 mmol) and triethylamine (0.07 mL, 0.50 mmol) were added in an attempt to increase conversion without any success. The reaction was quenched by addition of saturated NH$_4$Cl (aq) and concentrated. The residual material was purified by HPLC, collected fractions was freeze dried to give the title compound as a colourless solid. Chiral HPLC was made using an Chiralpak IB™, 150× 0.46 mm column, 15% EtOH in iso-Hexane, 0.5 mL/min, UV=254 nm, one major peak at 32.39 min (99.7%) and one minor peak at 30.69 min (0.3%).

Yield 48 mg (39%).

Chiral HPLC:Rt=32.39 min, 99.4% e.e.

$^1$H-NMR (300 MHz, DMSO-$d_6$): δ 8.16 (d, 1H), 7.79-7.66 (m, 3H), 7.45-7.30 (m, 5H), 7.28-7.18 (m, 3H), 7.11 (d, 1H), 5.28 (d, J=4.34 Hz, 1H), 3.71 (m, 1H), 2.44 (s, 3H), 2.41 (m, 1H), 1.24 (d, 3H), 0.89-0.81 (m, 4H)

APCI-MS m/z: 512.2 [MH$^+$].

(1R,2S)-1-{[1-(4-fluorophenyl)-1H-indazol-5-yl]oxy}-1-[4-(methylthio)phenyl]propan-2-amine hydrochloride (29a)

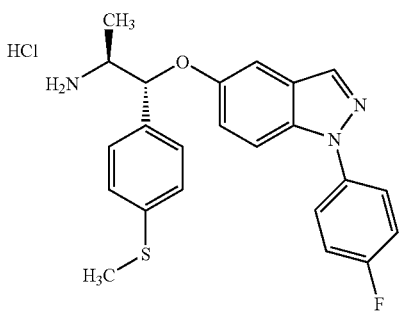

The subtitle compound was prepared as described in Example 1.

(1R,2S)-2-amino-1-[4-(methylthio)phenyl]propan-1-ol (595 mg, 3 mmol), 1-(4-Fluorophenyl)-5-iodoindazole (913 mg, 2.7 mmol), CuI (28 mg, 0.15 mmol), Cs$_2$CO$_3$ (1.95 g, 6 mmol) in butyronitrile (5 mL) and Toluene (2 mL) at +125° C. for 6 hours. After work up and purification by HPLC the subtitle compound was isolated as the hydrochloride salt by addition of 6-7 N HCl/2-Propanol solution and repeated evaporations from MeCN to get the subtitle compound as a beige solid. Yield 300 mg (25%).

$^1$H-NMR (300 MHz, DMSO-d6): δ 8.40 (brs, 3H), 8.20 (d, 1H), 7.79-7.71 (m, 3H), 7.45-7.24 (m, 7H), 7.14 (d, 1H), 5.69 (d, J=2.92 Hz, 1H), 3.65 (m, 1H), 2.45 (s, 3H), 1.19 (d, 3H).

APCI-MS m/z: 408.0 [MH$^+$-HCl]

(1R,2S)-2-amino-1-[4-(methylthio)phenyl]propan-1-ol hydrochloride (29b)

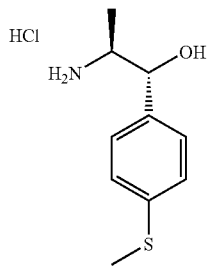

The subtitle compound was prepared following the procedure described by Jingjun Yin et. al. *J. Org. Chem.* 2006, 71, 840-843.

A mixture of (S)-tert-butyl 1-(4-(methylthio)phenyl)-1-oxopropan-2-ylcarbamate (29c, 2.7 g, 9.14 mmol), Aluminium isopropoxide (0.373 g, 1.83 mmol) and 2-propanol (7.75 mL, 100.54 mmol) in toluene (11.5 mL) was heated at +50° C. under argon for 16 hours. The reaction mixture was allowed to cool, EtOAc (100 mL) and 0.5N HCl (60 mL) was added, the organic layer was washed with water and brine, dried over Na$_2$SO$_4$, filtered and evaporated to give 2.65 crude product as a colourless solid.

The crude product was further purified by flash chromatography on silica, a gradient of 10% EtOAc to 30% EtOAc in Heptane followed by isocratic final concentration until all product had been eluted. Obtained 2.18 g of the intermediate BOC-protected subtitle compound as a colourless solid. APCI-MS m/z: 180.1, 198.1, 224.1 [MH$^+$-BOC-water, MH$^+$-BOC, MH$^+$-tBu-water]. The obtained material was dissolved in EtOAc (50 mL) and treated with 1.5 M HCl in EtOAc (40 ml, 60.00 mmol) at +70° C. for 90 minutes. Solvents was removed by evaporation and the solid residue was suspended in EtOAc (30 mL) and Et$_2$O (100 mL), the salt was collected by filtration and washed with ether (50 mL). Yield 1.68 g (78% yield)

APCI-MS m/z: 198.1 [MH$^+$]

$^1$H-NMR (400 Mhz, DMSO-d6): δ 8.05 (brs, 3H), 7.30 (d, 2H), 7.26 (d, 2H), 6.02 (d, J=4.24 Hz, 1H), 4.89 (t, 1H), 3.35 (m, 1H), 2.47 (s, 3H), 0.94 (d, 3H)

A sample of the above material was cyclizised to the corresponding oxazolidinone with 1 mol eq of 1-1'-carbonyldiimidazole and triethylamine in DCM.

By NMR-analysis and comparing shifts and coupling constants with literature values of oxazolidinones prepared from norephedrines with known stereochemistry (*Tetrahedron assym*, 1993, vol 4. no 12, pp 2513-2516 & *Org. lett*, 2005, 7, 13, 2755-2758), the relative stereochemistry, and consequently the absolute stereochemistry of the subtitle compound was determined.

(4S,5R)-4-methyl-5-[4-(methylthio)phenyl]-1,3-oxazolidin-2-one

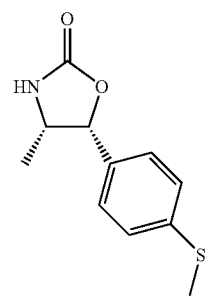

APCI-MS m/z: 224.0 [MH$^+$]

$^1$H-NMR (500 MHz, CDCl$_3$): δ 7.27 (d, 2H, Ar—H), 7.22 (d, 2H), 5.77 (brs, 1H, —NH), 5.68 (d, J=7.96 Hz, 1H, PhCH—), 4.19 (m, 1H, —CH(Me)—), 2.50 (s, 3H, Ar—SCH$_3$), 0.83 (d, J=6.5 Hz, 3H, —CH$_3$) ppm.

(S)-tert-butyl 1-(4-(methylthio)phenyl)-1-oxopropan-2-ylcarbamate (29c)

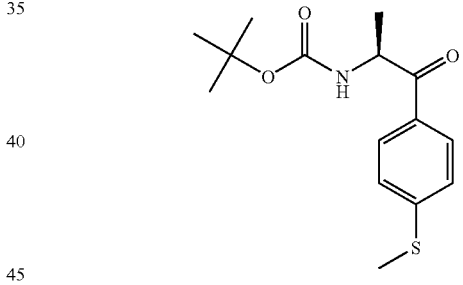

(S)-tert-butyl 1-(methoxy(methyl)amino)-1-oxopropan-2-ylcarbamate (2.32 g, 9.99 mmol) was suspended in dry THF (20 mL) and inerted with Argon. The slurry was cooled using an ice/acetone bath to −15 to −10° C. and slowly charged with isopropylmagnesium chloride 2.0M solution in THF (4.74 mL, 9.49 mmol). After addition a clear solution was obtained, to this solution was slowly added 4-thioanisolemagnesium bromide 0.5M in THF (24 mL, 12.00 mmol), after addition the reaction mixture was stirred at room temperature for 4 hours. The reaction was quenched by pouring it into 1 N HCl (100 mL), EtOAc (250 mL) was added to the mixture. The phases was separated, the organic phase was washed with brine, and the waterphases were back extracted once with EtOAc. The combined EtOAc phases were dried (Na2SO4), filtered and evaporated. The crude product was purified by flash chromatography on silica. A solvent gradient was used. 100% Heptane to 50% Heptane/DCM+5% MeOH, and then kept at final solvent ratio until product was eluted. Fractions with product was combined and solvent evaporated to give the subtitle compound as a colourless solid. Yield 2.7 g (92%)

LC/MS (APCI): (M+1)=295.9

¹H-NMR (300 MHz, DMSO-d₆): δ 7.89 (d, 2H), 7.36 (d, 2H), 7.28 (d, 1H), 5.00 (m, 1H), 2.54 (s, 3H), 1.35 (s, 9H), 1.21 (d, 3H)

APCI-MS m/z: 295.9, 195.9 [MH⁺, MH⁺-BOC]

Example 30

N-[(1R,2S)-1-phenyl-1-(1-propan-2-ylindazol-5-yl)oxy-propan-2-yl]methanesulfonamide

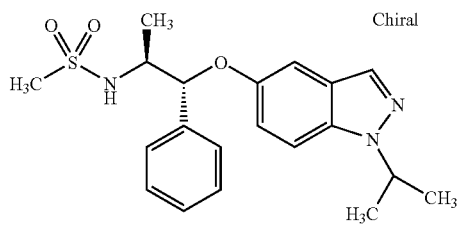

The title compound was prepared from (1R,2S)-1-[(1-isopropyl-1H-indazol-5-yl)oxy]-1-phenylpropan-2-amine (30b, 31 mg, 100 μmol) and methanesulfonyl chloride (34 mg, 300 μmol) as described in Example 2b. Yield 28 mg (72%).

APCI-MS: m/z 388 [MH⁺]

¹H NMR (400 MHz, d₆-acetone) δ 7.75 (s, 1H), 7.50 (m, 3H), 7.38 (t, J=7.5 Hz, 2H), 7.29 (m, 1H), 7.15 (dd, J=9.0, 2.3 Hz, 1H), 7.03 (d, J=2.3 Hz, 1H), 6.26 (d, J=8.8 Hz, 1H), 5.41 (d, J=4.4 Hz, 1H), 4.88 (septet, J=6.7 Hz, 1H), 3.90 (m, 1H), 2.77 (s, 3H), 1.47 (dd, J=6.7, 3.5 Hz, 6H), 1.32 (d, J=6.7 Hz, 3H).

(1R,2S)-1-[(1-isopropyl-1H-indazol-5-yl)oxy]-1-phenylpropan-2-amine (30b)

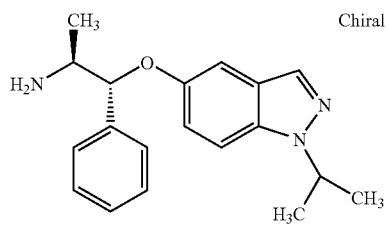

A mixture of 5-iodo-1-isopropyl-1H-indazole (30c, 461 mg, 1.26 mmol), (1R,2S)-2-amino-1-phenylpropan-1-ol (286 mg, 1.89 mmol), copper (I) iodide (25 mg, 130 μmol), and cesium carbonate (1.45 g, 3.8 mmol) in butyronitrile (5 ml) was stirred at 125° C. for 2 h. Then the mixture was cooled to room temp., the inorganic material was removed by filtration and washed with ethyl acetate. The combined organic solutions were concentrated i. vac., and the product purified by flash chromatography on silica gel (ethyl acetate/methanol). Yield 200 mg (51%) of a brown oil.

APCI-MS: m/z 310 [MH⁺]

¹H NMR (400 MHz, DMSO-d₆/D₂O/TFA) δ 7.80 (s, 1H), 7.53 (d, J=9.0 Hz, 1H), 7.40 (d, J=7.1 Hz, 2H), 7.33 (t, J=7.5 Hz, 2H), 7.24 (m, 1H), 7.08 (dd, J=9.0, 2.3 Hz, 1H), 6.98 (d, J=2.1 Hz, 1H), 5.75 (s, 1H), 5.03 (d, J=5.3 Hz, 1H), 4.86 (septet, J=6.7 Hz, 1H), 3.15 (quintet, J=6.0 Hz, 1H), 1.41 (dd, J=6.4, 5.5 Hz, 6H), 1.06 (d, J=6.5 Hz, 3H).

5-Iodo-1-isopropyl-1H-indazole (30c)

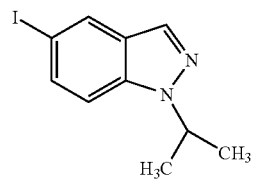

A mixture of 5-iodo-1H-indazole (488 mg, 2 mmol), isopropyl bromide (244 mg, 2 mmol), and KOtBu (336 mg, 3 mmol) in dry DMF (4 ml) was stirred at room temp. overnight. Then it was diluted with ethyl acetate (50 ml), washed with water (2×50 ml), and dried with Na₂SO₄. Evaporation of solvent and purification by flash chromatography on silica gel (n-heptane/ethyl acetate) afforded the subtitle compound (298 mg, 52%) along with 5-iodo-2-isopropyl-2H-indazole (227 mg, 40%).

¹H NMR (400 MHz, CDCl₃) δ 8.11 (d, J=0.9 Hz, 1H), 7.94 (s, 1H), 7.60 (dd, J=8.8, 1.5 Hz, 1H), 7.26 (d, J=8.8 Hz, 1H), 4.83 (septet, J=6.8 Hz, 1H), 1.61 (d, J=6.7 Hz, 6H).

APCI-MS: m/z 287 [MH⁺]

Example 31

N-[(1R,2S)-1-[1-(4-fluorophenyl)indazol-5-yl]oxy-1-(4-methylsulfinylphenyl)propan-2-yl]cyclopropanesulfonamide

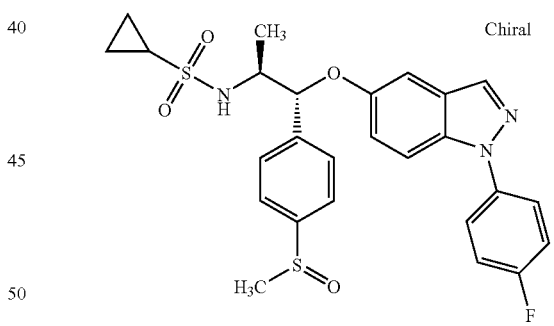

N-[(1R,2S)-1-[1-(4-fluorophenyl)indazol-5-yl]oxy-1-(4-methylsulfanylphenyl)propan-2-yl]cyclopropanesulfonamide (29, 20.5 mg, 0.04 mmol) was dissolved in DCM (2 mL) and cooled in an ice bath. 3-Chloroperbenzoic acid (70-75%) (10 mg, 0.04 mmol) dissolved in DCM (0.1 mL) was added. The reaction was stirred for 30 min, quenched by addition of 10% Na₂SO₃ solution (0.5 mL). Purification by HPLC and freeze drying of fractions with product gave the title compound as a colourless solid. Yield 17 mg (80%).

¹H-NMR (300 MHz, DMSO-d₆): δ 8.17 (d, 1H), 7.78-7.58 (m, 7H), 7.48-7.35 (m, 3H), 7.25 (dd, 1H), 7.16 (d, 1H), 5.40 (d, J=4.51 Hz, 1H), 3.77 (m, 1H), 2.72 (s, 3H), 2.42 (m, 1H), 1.25 (d, 3H), 0.90-0.80 (m, 4H).

APCI-MS: m/z: 528.1 [MH⁺]

Example 32

N-[(1R,2S)-1-(1-cyclopentylindazol-5-yl)oxy-1-phenyl-propan-2-yl]cyclopropanesulfonamide

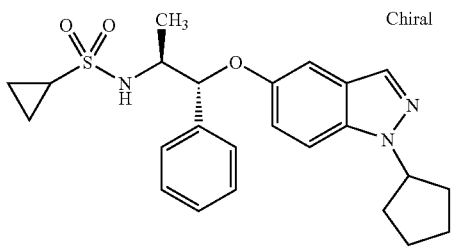

The title compound was prepared from (1R,2S)-1-[(1-cyclopentyl-1H-indazol-5-yl)oxy]-1-phenylpropan-2-amine (32b, 17 mg, 51 µmol) and cyclopropanesulfonyl chloride (34 mg, 153 µmol) as described in Example 2b. Yield 10 mg (45%).

$^1$H NMR (400 MHz, d$_6$-acetone) δ 7.73 (s, 1H), 7.49 (m, 3H), 7.37 (t, J=7.5 Hz, 2H), 7.28 (m, 1H), 7.16 (dd, J=9.0, 2.3 Hz, 1H), 7.02 (d, J=2.3 Hz, 1H), 6.30 (d, J=9.0 Hz, 1H), 5.47 (d, J=3.9 Hz, 1H), 5.06 (quintet, J=7.1 Hz, 1H), 3.90 (m, 1H), 2.42 (m 1H), 1.88 (m, 2H), 1.70 (m, 2H), 1.33 (d, J=6.7 Hz, 3H), 1.01-0.83 (m, 4H).

APCI-MS: m/z 440 [MH$^+$]

(1R,2S)-1-[(1-cyclopentyl-1H-indazol-5-yl)oxy]-1-phenylpropan-2-amine (32b)

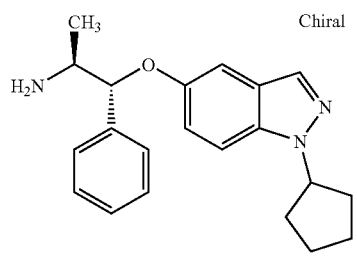

Prepared from 1-cyclopentyl-5-iodo-1H-indazole (37c, 158 mg, 500 µmol) as described for 30b. Yield 34 mg (20%).
APCI-MS: m/z 336 [MH$^+$]

1-Cyclopentyl-5-iodo-1H-indazole (32c)

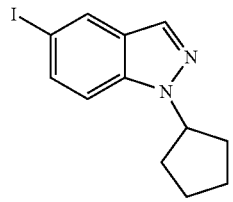

A mixture of 2-fluoro-5-iodobenzaldehyde (500 mg, 2 mmol), cyclopentylhydrazine (273 mg, 2 mmol), and cesium carbonate (1.91 g, 5 mmol) in NMP (5ml) was stirred at 100° C. overnight. Then KOtBu (560 mg, 5 mmol) and DMF (10 ml) were added, and the mixture was stirred at 150° C. for 5 h. After cooling to room temp., the mixture was diluted with ethyl acetate (100 ml), and washed with water (3×50 ml), and dried. Evaporation of solvent afforded batch residue, which was dissolved in acetonitrile (50 ml), and the insoluble material was removed vy filtration. Flash chromatography on silica gel (n-heptane/ethyl acetate) afforded yellow oil, 158 mg (25%).

$^1$H NMR (400 MHz, CDCl$_3$) δ 8.08 (d, J=0.9 Hz, 1H), 7.91 (s, 1H), 7.59 (dd, J=8.8, 1.5 Hz, 1H), 7.26 (d, J=9.4 Hz, 1H, partially covered with the signal of solvent), 4.95 (quintet, J=7.4 Hz, 1H), 2.17 (m, 4H), 1.98 (m, 2H), 1.75 (m, 2H).

APCI-MS: m/z 313 [MH$^+$]

Example 33

N-[(1R,2S)-1-phenyl-1-(1-propan-2-ylindazol-5-yl)oxy-propan-2-yl]cyclopropanesulfonamide

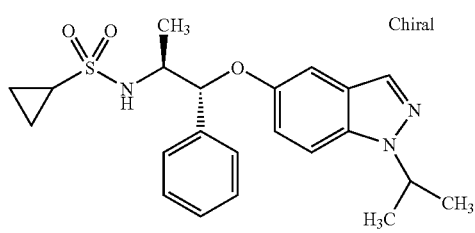

The title compound was prepared from (1R,2S)-1-[(1-isopropyl-1H-indazol-5-yl)oxy]-1-phenylpropan-2-amine (30b, 31 mg, 100 µmol) and cyclopropanelsulfonyl chloride (42 mg, 300 µmol) as described in Example 2b. Yield 33 mg (80%).

$^1$H NMR (400 MHz, d$_6$-acetone) δ 7.74 (s, 1H), 7.49 (m, 3H), 7.38 (t, J=7.5 Hz, 2H), 7.28 (m, 1H), 7.16 (dd, J=9.2, 2.3 Hz, 1H), 7.03 (d, J=2.3 Hz, 1H), 6.30 (d, J=8.8 Hz, 1H), 5.47 (d, J=4.1 Hz, 1H), 4.88 (septet, J=6.7 Hz, 1H), 3.90 (m, 1H), 2.42 (m, 1H), 1.48 (dd, J=6.6, 3.8 Hz, 6H), 1.33 (d, J=6.9 Hz, 3H), 1.01-0.83 (m, 4H).

APCI-MS: m/z 414 [MH$^+$]

Example 34

N-[(1R,2S)-1-[1-(4-fluorophenyl)indazol-5-yl]oxy-1-(4-methylsulfonylphenyl)propan-2-yl]cyclopropanesulfonamide

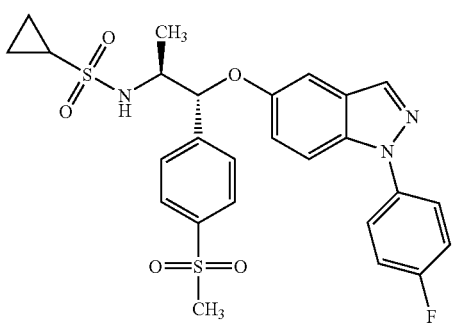

N-[(1R,2S)-1-[1-(4-fluorophenyl)indazol-5-yl]oxy-1-(4-methylsulfanylphenyl)propan-2-yl]cyclopropanesulfonamide (29, 19 mg, 0.037 mmol) was dissolved in acetic acid (1.5 mL), 35% H$_2$O$_2$ (1 mL) was added and the mixture was stirred at +60° C. for 45 minutes. After cooling to room temperature the reaction mixture was diluted with water and purified by HPLC. The collected fractions containing the desired product was freeze dried. Obtained the title compound as a colourless solid. Yield 16 mg (57%).

¹H-NMR (300 MHz, DMSO-d₆): δ 8.17 (d, 1H), 7.94 (d, 2H), 7.78-7.65 (m, 5H), 7.49-7.35 (m, 3H), 7.26 (dd, 1H), 7.16 (d, 1H), 5.45 (d, J=4.51 Hz, 1H), 3.80 (m, 1H), 3.20 (s, 3H), 2.45 (m, 1H), 1.25 (d, 3H), 0.90-0.80 (m, 4H)

APCI-MS m/z: 544.1 [MH⁺]

Example 35

N-[(1RS,2SR)-1-[6-chloro-1-(4-fluorophenyl)indazol-5-yl]oxy-1-(4-fluorophenyl)propan-2-yl]cyclopropanesulfonamide

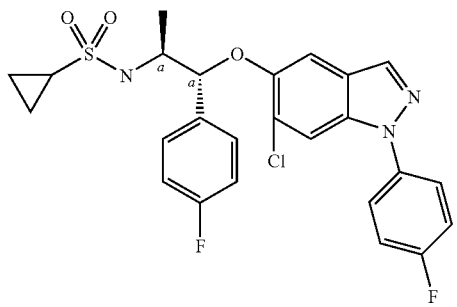

a = relative mixture

Prepared according to the procedure described for Example 1 starting with (1RS,2SR)-1-[6-chloro-1-(4-fluorophenyl)indazol-5-yl]oxy-1-(4-fluorophenyl)propan-2-amine (35a-rac-2, 55 mg, 0.13 mmol) and cyclopropylsulphonyl chloride (42 μl, 0.4 mmol). Yield: 2 mg (3%).

¹H NMR (400 MHz, CD₃OD) δ 8.02 (d, J=0.7 Hz, 1H), 7.78 (s, 1H), 7.67 (td, J=8.7, 3.8 Hz, 2H), 7.48 (dd, J=8.7, 5.3 Hz, 2H), 7.31 (ddd, J=12.4, 8.5, 3.7 Hz, 2H), 7.19 (s, 1H), 7.11 (t, J=8.8 Hz, 2H), 5.48 (d, J=4.6 Hz, 1H), 3.90 (dt, J=11.5, 6.8 Hz, 1H), 2.39 (tt, J=8.0, 4.8 Hz, 1H), 1.41 (d, J=6.9 Hz, 3H), 1.03-0.99 (m, 2H), 0.92-0.87 (m, 2H).

APCI-MS: 518 m/z [MH⁺]

1-[6-chloro-1-(4-fluorophenyl)indazol-5-yl]oxy-1-(4-fluorophenyl)propan-2-amine (35a)

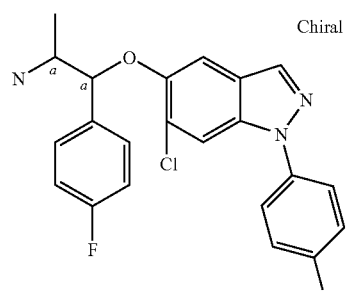

a = relative mixture

1-{[6-Chloro-1-(4-fluorophenyl)-1H-indazol-5-yl]oxy}-1-(4-fluorophenyl)acetone (500 mg, 1.21 mmol), ammonium acetate (35b, 934 mg, 12.11) and cyanoborohydride on polymer support (1.82 g, 3.63 mmol) were mixed in methanol (3 ml) and heated in micro at 140° C. for 10 min. The mixture was concentrated and treated with NaHCO₃ and DCM. The organic phase was concentrated and the crude product was purified by flash chromatography (EtOAc/heptane followed by EtOAc/methanol). The diastereomers were separated on preparative HPLC (Kromasil column, water buffered with 2 g NH₄OAc/l, pH set to 5.5 with HOAc, and MeCN, 25%-75%) to give the syn-isomer (1RS,2RS)-1-[6-chloro-1-(4-fluorophenyl)indazol-5-yl]oxy-1-(4-fluorophenyl)propan-2-amine (35a-rac-1) as first eluated isomer (assignment by 1H-NMR).

¹H NMR (400 MHz, CD₃OD) δ 8.05 (d, J=0.9 Hz, 1H), 7.75 (s, 1H), 7.65 (tt, J=4.6, 2.3 Hz, 2H), 7.53 (dd, J=12.0, 1.9 Hz, 2H), 7.34-7.26 (m, 3H), 7.13 (t, J=8.8 Hz, 2H), 5.28 (d, J=8.3 Hz, 1H), 3.69 (dd, J=8.2, 6.8 Hz, 1H), 1.17 (d, J=6.7 Hz, 3H).

APCI-MS: 414 m/z [MH⁺].

The anti-isomer (1RS,2SR)-1-[6-chloro-1-(4-fluorophenyl)indazol-5-yl]oxy-1-(4-fluorophenyl)propan-2-amine (35a-rac-2) was eluated secondly.

¹H NMR (400 MHz, CD₃OD) δ 8.02 (s, 1H), 7.79 (s, 1H), 7.69-7.64 (m, 2H), 7.48-7.43 (m, 2H), 7.31 (dd, J=20.8, 3.4 Hz, 2H), 7.18-7.10 (m, 3H), 5.41 (d, J=4.6 Hz, 1H), 3.46 (dt, J=11.1, 6.6 Hz, 1H), 1.27 (d, J=6.5 Hz, 3H).

APCI-MS: 414 m/z [MH⁺].

1-{[6-chloro-1-(4-fluorophenyl)-1H-indazol-5-yl]oxy}-1-(4-fluorophenyl)acetone (35b)

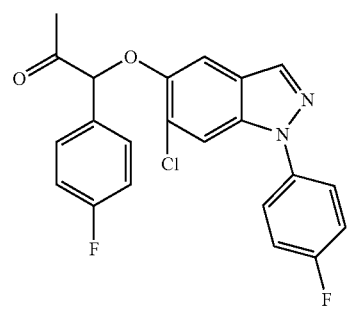

4-Fluorophenylacetone (388 μl, 2.9 mmol) in DCM (12 ml) was cooled to 0° C. and bromine (672 mg, 2.9 mmol) was slowly added. The mixture was stirred for 30 min and then concentrated in vacuo. The crude intermediate was added to a mixture of 6-chloro-1-(4-fluorophenyl)-1H-indazol-5-ol, preparation described in case 102561, example 4, (762 mg, 2.9 mmol) and potassium carbonate (804 mg, 5.8 mmol) in THF (12 ml). The mixture was stirred for 4 h, filtrated and concentrated. The crude product was purified by flash chromatography (EtOAc/heptane, product eluted at 40% EtOAc) to give the title compound (1.06 g, 88%).

APCI-MS: 413 m/z [MH⁺].

Example 36

N-[(1RS,2RS)-1-[6-chloro-1-(4-fluorophenyl)indazol-5-yl]oxy-1-(4-fluorophenyl)propan-2-yl]cyclopropanesulfonamide

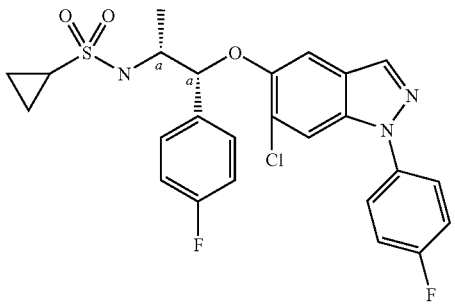

a = relative mixture

Prepared according to the procedure described for Example 1 starting with (1RS,2SR)-1-[6-chloro-1-(4-fluorophenyl)indazol-5-yl]oxy-1-(4-fluorophenyl)propan-2-amine (35a-rac-1, 35 mg, 0.08 mmol) and cyclopropylsulphonyl chloride (27 μl, 0.25 mmol). Yield: 2 mg (5%).

$^1$H NMR (400 MHz, CD3OD) δ 8.04 (d, J=0.7 Hz, 1H), 7.77 (s, 1H), 7.67 (td, J=8.7, 4.1 Hz, 2H), 7.53 (dd, J=8.8, 5.4 Hz, 2H), 7.31 (ddd, J=15.6, 5.3, 3.3 Hz, 2H), 7.26 (s, 1H), 7.10 (t, J=8.8 Hz, 2H), 5.49 (d, J=5.1 Hz, 1H), 4.04 (dt, J=12.0, 6.8 Hz, 1H), 2.52 (tt, J=8.0, 4.9 Hz, 1H), 1.29 (d, J=6.9 Hz, 3H), 1.05-0.90 (m, 4H).

APCI-MS: 518 m/z [MH$^+$]

Example 37

(R)—N-[2-[1-(4-fluorophenyl)indazol-5-yl]sulfanyl-2-phenyl-ethyl]cyclopropanesulfonamide

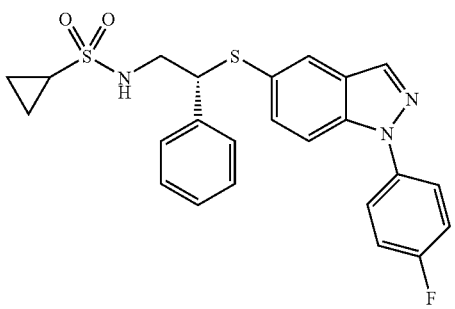

The racemic mixture of N-[2-[1-(4-fluorophenyl)indazol-5-yl]sulfanyl-2-phenyl-ethyl]cyclopropanesulfonamide (37-rac, 10 mg) were separated on Thales SFC, Chiralpak IA column(74% CO$_2$, 26% MeOH) collecting the first eluating peak. Yield: 4 mg (40%).

APCI-MS: m/z 376.2 [MH$^+$]

Chiral analysis was made using a CHIRALPAK® IB, 150× 0.46 mm column, 26% MeOH/74% CO$_2$, 3.5 mL/min, UV=254 nm: >98% ee, Rt=6.78 min N-[2-[1-(4-fluorophenyl)indazol-5-yl]sulfanyl-2-phenyl-ethyl]cyclopropanesulfonamide (37a)

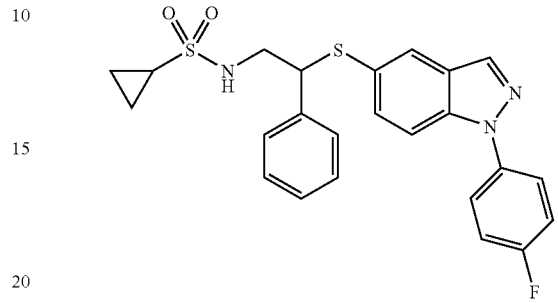

Cyclopropanesulfonyl chloride (7 μl, 0.068 mmol was added to 2-phenyl-2-(1-(4-fluorophenyl)-1H-indazol-5-yloxy)-ethylamine (37b, 0.01 g, 0.027 mmol), triethylamine (15 μl, 0.11 mmol) in MeCN (1 ml) at room temperature. The reaction mixture was stirred for 2 hours, concentrated, diluted with 10% NaHSO$_4$ (aq) and extracted with EtOAc. The organic phase was washed with 10% NaHSO$_4$ (aq). The crude product was further purified by HPLC. Yield 12 mg (95%).

$^1$H NMR (400 MHz, DMSO-d6) δ 8.33 (s, 1H), 7.92 (s, 1H), 7.78 (dd, J=8.9, 4.8 Hz, 1H), 7.73 (d, J=9.2 Hz, 2H), 7.43 (s, 3H), 7.31 (d, J=4.2 Hz, 6H), 4.43 (t, J=22.1 Hz, 1H), 3.49 (s, 2H), 2.41 (m, 1H), 0.78 (s, 4H).

APCI-MS: m/z 468 [MH$^+$]

2-(1-(4-Fluorophenyl)-1H-indazol-5-ylthio)-2-phenyl-ethylamine (37b)

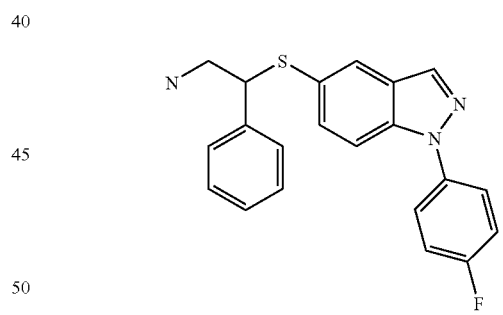

1-(4-Fluorophenyl)-1H-indazole-5-thiol (37c, 0.068 g, 0.28 mmol), (E)-(2-nitrovinyl)benzene (0.055 g, 0.37 mmol) and DMAP (cat. amount) in THF (5 ml) were stirred at 70° C. for 2 hours. The solvent was evaporated and the mixture was partitioned between water/EtOAc. The organic phase was dried and evaporate under reduced pressure. To this mixture EtOH (5 ml), water (3 ml), conc HCl (1 ml) and Zn (0.26 g) were added and the mixture was stirred at 70° C. for 2 hours. After cooling to room temperature water (15 ml) was added and the EtOH was evaporated. The pH of the mixture was adjusted to pH10 with NaOH (5N, aq) and extracted with EtOAc (3*25 ml). The organic phases were combined and dried, the solvent was evaporated under reduced pressure. Purification was done by HPLC. Yield 0.010 g (10%)

APCI-MS: m/z 364 [MH$^+$]

1-(4-Fluorophenyl)-1H-indazole-5-thiol (37c)

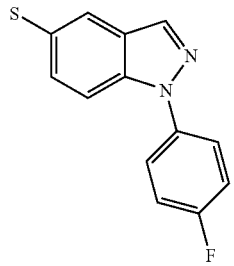

To S-1-(4-Fluorophenyl)-1H-indazol-5-yl benzothioate (37d, 0.046 g, 0.13 mmol) in methanol (3 mL), potassium carbonate (0.011 mL, 0.20 mmol) was added and the mixture was stirred at rt for 2 hrs. water was than added, 1N HCl (2 ml) and extracted with EtOAc (2*20 ml), dried, evaporated and then purified on HPLC. The relevant fractions were collected freeze dried and analysed by LC/MS.

APCI-MS: m/z 245 [MH$^+$]

S-1-(4-fluorophenyl)-1H-indazol-5-yl benzothioate (37d)

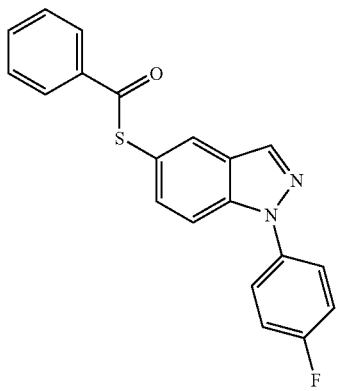

To a solution of 1-(4-fluorophenyl)-5-iodo-1H-indazole (0.224 g, 0.66 mmol), thiobenzoic acid (0.093 ml, 0.79 mmol), 3,4,7,8-tetramethyl-1,10-phenantroline (0.031 g, 0.13 mmol) and N,N-diisopropylamine (0.220 ml, 1.32 mmol) in toluene (2.5 ml) was added copper(I) iodine (2.245 µl, 0.07 mmol). The resulting mixture was stirred at 110C O/N. The reaction mixture was cooled to rt diluted with EtOAc and washed with water. The organic phase was the dried the solvent evaporated and then purified on HPLC. The relevant fractions were collected freeze dried to give 45 mg (20%) of product which was analysed by LC/MS.

APCI-MS: m/z 349 [MH$^+$]

Example 38

N-((1R,2S)-1-(1-(4-fluorophenyl)-1H-indazol-5-ylthio)-1-phenylpropan-2-yl)methanesulfonamide

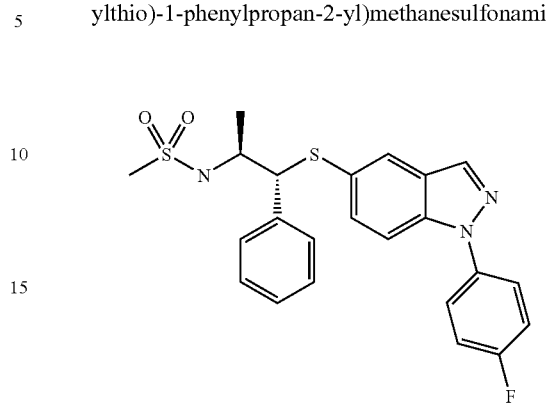

To (2R,3R)-2-methyl-1-(methylsulfonyl)-3-phenylaziridine (38a, 0.03 g, 0.14 mmol) in THF (4 ml) was added 1-(4-Fluorophenyl)-1H-indazole-5-thiol (37c, 0.038 g, 0.16 mmol) and sodium hydride (5.11 mg, 0.21 mmol) on an ice bath with stirring. The ice bath was removed and the mixture was stirren at room temperature over night. The solvent was removed and the mixture was purified on HPLC. Yield 0.007 g (11%).

$^1$H NMR (500 MHz, DMSO-d6) δ 8.27 (d, J=0.7 Hz, 1H), 7.79 (d, J=1.0 Hz, 1H), 7.74 (m, 2H), 7.66 (d, J=8.9 Hz, 2H), 7.40 (m, 5H), 7.29 (t, J=7.6 Hz, 2H), 7.19 (m, 2H), 4.42 (d, J=6.3 Hz, 1H), 4.14 (t, J=5.2 Hz, 1H), 2.62 (s, 3H), 1.35 (s, 3H).

APCI-MS: m/z 456 [MH$^+$]

(2R,3R)-2-Methyl-1-(methylsulfonyl)-3-phenylaziridine (38a)

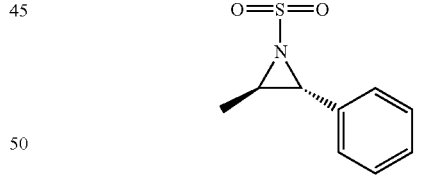

To (2R,3R)-2-Methyl-3-phenylaziridine (38b, 0.08 g, 0.60 mmol) in CH$_2$Cl$_2$ (3 ml) was is added N,N-Diisopropylmethyamine (0.219 ml, 1.32 mmol) and the reaction mixture was cooled to −10° C. before methansulfonyl chloride (0.051 ml, 0.66 mmol) was added The mixture was stirred for 30 min at −10° C. than at room temperature for 1 h. The crude sample was added to a Chromasil C18 column and was eluted with MeCN/H2O 35-70%, 20 min.

Yield 0.055 g (43%).

$^1$H NMR (300 MHz, DMSO-d6) δ 7.36 (m, 5H), 3.72 (d, J=4.4 Hz, 1H), 3.13 (s, 3H), 3.03 (m, 1H), 1.64 (d, J=6.0 Hz, 3H).

APCI-MS: m/z 253.1 [MH$^+$]

(2R,3R)-2-Methyl-3-phenylaziridine (38b)

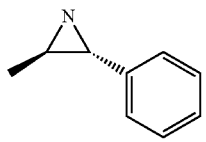

To (1R,2S)-(–)-norephedrine (1 g, 6.61 mmol) in THF (20 mL), triphenylphosphine (1.98 ml, 7.94 mmol), diisopropyl azodicarboxylate (1.401 ml, 7.27 mmol) and triethylamine (2.6 ml, 18.8 mmol) was added anr the rm was stirred at room temperature over night. The solvent was evaporated and the crude material was purified on silica eluting with Heptane/EtPAc 1+4 to EtOAc 100% and EtOAc/MeOH 95+5% the fractions containing product were collected giving 2.5 g of with solid containing lot of P(Ph)$_3$O according to LC/MS. This solid was stirred in hexane (50 ml) O/N and than filtered through a pad of Celite 545 giving 0.6 g of an oil.

$^1$H NMR (400 MHz, CDCl$_3$) δ 7.32 (m, 5H), 2.75 (d, J=2.7 Hz, 1H), 2.22 (m, 1H), 1.45 (d, J=5.5 Hz, 3H)

APCI-MS m/z 134.1 [MH$^+$]

Example 39

N-[(1R,2S)-1-[1-(4-fluorophenyl)indazol-5-yl]sulfonyl-1-phenyl-propan-2-yl]methanesulfonamide

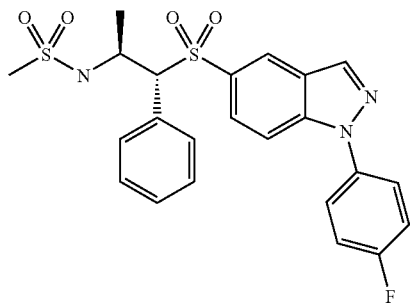

N-((1R,2S)-1-(1-(4-Fluorophenyl)-1H-indazol-5-ylthio)-1-phenylpropan-2-yl)methanesulfonamide (Example 38, 3.00 mg, 6.59 μmol) was dissolved in H$_2$O$_2$ (0.5 ml, 16.32 mmol) and acetic acid (0.5 ml) and stirred at 50° C. for 120 min. After removing of the solvents the mixture was purified on HPLC. Yield 0.0015 g (46%)

$^1$H NMR (500 MHz, DMSO-d6) δ 8.51 (s, 1H), 8.19 (d, J=1.1 Hz, 1H), 7.75 (q, J=4.6 Hz, 3H), 7.56 (m 1H), 7.46 (d, J=8.8 Hz, 2H), 7.26 (m, 2H), 7.20 (m, 3H), 7.08 (m, 1H), 4.58 (m, 1H), 4.40 (m, 1H), 2.61 (s, 3H), 1.46 (d, J=6.6 Hz, 3H).

APCI-MS: m/z 505 [MH$^+$+18]

Example 40

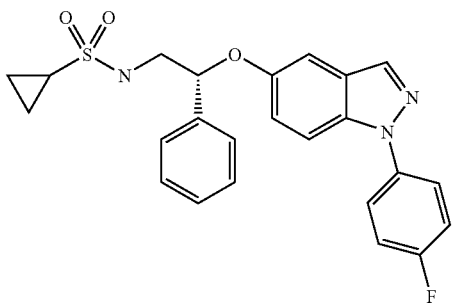

N-[(2R)-2-[1-(4-fluorophenyl)indazol-5-yl]oxy-2-phenyl-ethyl]cyclopropanesulfonamide Prepared according to the procedure described for Example 1 from (1R)-1-[1-(4-fluorophenyl)indazol-5-yl]oxy-1-phenyl-ethan-2-amine (40a, 31 mg, 0.09 mmol) cyclopropylsulphone chloride (28 μl, 0.27 mmol). Yield: 10 mg (25%).

$^1$H NMR (400 MHz, CD$_3$OD) δ 8.01 (s, 1H), 7.68-7.63 (m, 2H), 7.58 (d, J=9.2 Hz, 1H), 7.47 (d, J=7.3 Hz, 2H), 7.37 (t, J=7.4 Hz, 2H), 7.32-7.24 (m, 4H), 7.14 (d, J=2.3 Hz, 1H), 5.41 (dd, J=8.1, 4.1 Hz, 1H), 3.61-3.47 (m, 2H), 2.51 (tt, J=8.0, 4.8 Hz, 1H), 1.06-0.90 (m, 4H).

APCI-MS: 452 m/z [MH$^+$]

[(1R)-2-[1-(4-fluorophenyl)indazol-5-yl]oxy-1-phenyl-ethan-2-amine (40a)

Prepared from (1R)-1-phenyl-1-hydroxy-ethan-2-amine (294 mg, 2.15 mmol) and 1-(4-fluorophenyl)-5-iodoindazole (484 mg, 1.43 mmol) according to the protocol for 1a. Yield: 125 mg (17%).

APCI-MS: 348 m/z [MH$^+$]

Example 41

N-[(2S)-2-[1-(4-fluorophenyl)indazol-5-yl]oxy-2-phenyl-ethyl]cyclopropanesulfonamide

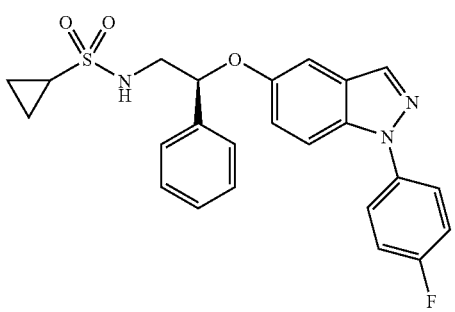

Prepared according to the procedure described for Example 1 from [(1S)-1-[1-(4-fluorophenyl)indazol-5-yl]oxy-1-phenyl-ethan-2-amine (41a, 31 mg, 0.09 mmol) cyclopropylsulphone chloride (28 μl, 0.27 mmol). Yield: 22 mg (54%).

[(1S)-1-[1-(4-fluorophenyl)indazol-5-yl]oxy-1-phenyl-ethan-2-amine (41a)

Prepared from (1S)-1-phenyl-1-hydroxy-ethan-2-amine (294 mg, 2.15 mmol) and 1-(4-fluorophenyl)-5-iodoindazole (484 mg, 1.43 mmol) according to the protocol for 1a. Yield: 175 mg (23%).
APCI-MS: 348 m/z [MH+]

Example 42

N-((1R,2S)-1-(1-(4-fluorophenyl)-1H-indazol-5-yloxy)-1-(quinolin-3-yl)propan-2-yl)cyclopropanesulfonamide

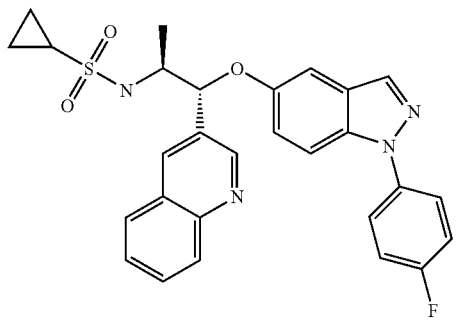

(1R,2S)-1-(1-(4-fluorophenyl)-1H-indazol-5-yloxy)-1-(quinolin-3-yl)propan-2-amine bis(2,2,2-trifluoroacetate) (42a, 65 mg, 0.10 mmol) was dissolved in THF (1.5 mL), triethylamine (75 μl, 0.54 mmol) was added followed by cyclopropanesulfonyl chloride (15 μl, 0.15 mmol). The reaction mixture was stirred at room temperature, after 1.5 hours another portion of triethylamine (75 μl, 0.54 mmol) and excess of cyclopropanesulfonyl chloride (50 μl, 0.49 mmol) was added. The reaction mixture was left over night at room temperature. Solvent was removed by evaporation and the residual material was purified by HPLC. Yield 18 mg (34%).
$^1$H-NMR (300 MHz, DMSO-$d_6$): δ 8.99 (d, 1H), 8.37 (d, 1H), 8.14 (d, 1H), 8.00 (m, 2H), 7.80-7.66 (m, 4H), 7.60 (m, 1H), 7.48-7.22 (m, 5H), 5.53 (d, J=5.3 Hz, 1H), 3.94 (m, 1H), 2.45 (m, 1H), 1.35 (d, 3H), 0.89-0.74 (m, 4H).
APCI-MS m/z: 517 [MH+]

(1R,2S)-1-(1-(4-fluorophenyl)-1H-indazol-5-yloxy)-1-(quinolin-3-yl)propan-2-amine bis(2,2,2-trifluoroacetate) (42a)

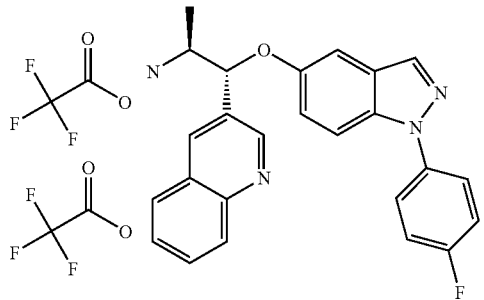

Following the procedure described in Example 1. Starting from (1R,2S)-2-amino-1-(quinolin-3-yl)propan-1-ol dihydrochloride (42b, 250 mg, 0.80 mmol), 1-(4-fluorophenyl)-5-iodo-1H-indazole (340 mg, 1.01 mmol), Cs$_2$CO$_3$ (1070 mg, 3.28 mmol) and CuI (36 mg, 0.19 mmol) in butyronitrile (4 mL), the reaction vessel was sealed and flushed with argon, the resulting slurry was stirred at +125° C. for 5 hours, the temperature was then lowered to 100° C. and the mixture was stirred over night 16 hours. Workup and purification by HPLC afforded the subtitle compound as a hygroscopic yellow powder. Yield 200 mg (39%)
$^1$H-NMR (300 MHz, DMSO-d6): δ 9.01 (d, 1H), 8.41 (d, 1H), 8.26 (brs, 3H), 8.17 (d, 1H), 8.02 (t, 2H), 7.84-7.68 (m, 4H), 7.64 (m, 1H), 7.44-7.34 (m, 3H), 7.28 (d, 1H), 5.89 (d, J=3.32 Hz, 1H), 3.95 (m, 1H), 1.26 (d, 3H)
APCI-MS m/z: 413.1 [MH+-2TFA]

(1R,2S)-2-amino-1-(quinolin-3-yl)propan-1-ol dihydrochloride (42b)

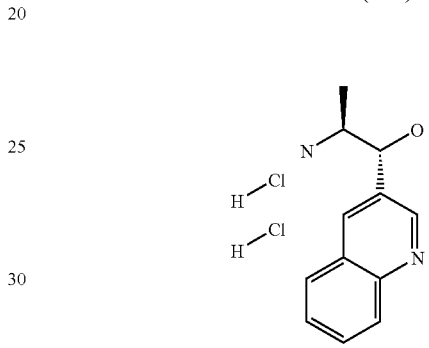

Following the procedure described for preparation of 29b. Starting from (S)-tert-butyl 1-oxo-1-(quinolin-3-yl)propan-2-ylcarbamate (42c, 1.6 g, 5.33 mmol), Aluminium isopropoxide (0.68 g, 3.33 mmol) and 2-propanol (4.5 mL, 59.16 mmol) in toluene (7 mL) stirred at +50° C. in sealed reaction tube flushed with argon for 16 hours. Work up and deprotection of the intermediate BOC-protected amine afforded the subtitle compound as a colourless solid. Yield 1.29 g (88%).
$^1$H-NMR (400 Mhz, DMSO-d6): δ 9.23 (d, 1H), 8.97 (s, 1H), 8.42-8.24 (m, 5H), 8.06 (t, 1H), 7.89 (t, 1H), 6.68 (vbrs, 1H), 5.28 (d, J=3.72 Hz, 1H), 3.68 (m, 1H), 1.10 (d, 3H).
APCI-MS m/z: 203 [MH+-2HCl]

(S)-tert-butyl 1-oxo-1-(quinolin-3-yl)propan-2-ylcarbamate (42c)

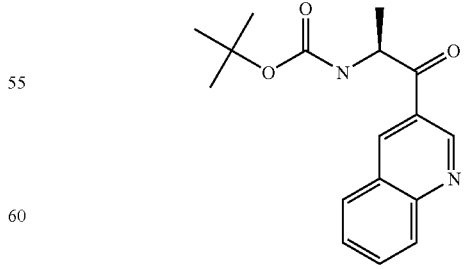

(S)-tert-butyl 1-(methoxy(methyl)amino)-1-oxopropan-2-ylcarbamate (2.5 g, 10.76 mmol) was suspended in THF (5 mL) and stirred at −10° C., isopropylmagnesium chloride 2.0M solution in THF (5.4 ml, 10.80 mmol) was added and a solution was formed. To this solution was added a solution of Lithium tri(3-quinolinyl)magnesiate in THF/Hexane, prepared from 3-bromoquinoline (1.471 ml, 10.81 mmol) according to the procedure described by Sylvain Dumouchel et-al. in *Tetrahedron* 59 (2003) 8629-8640. The mixture was stirred at −10° C. for 30 minutes and was the allowed to reach room temperature and stirred over night, 15 h. The reaction mixture, a clear red solution, was slowly poured into ice-cooled 1M HCl (aq) (100 mL). EtOAc (150 mL) was added and the mixture was stirred for a few minutes, the water phase was extracted once with EtOAc, the combined EtOAc solutions was further washed with saturated NaHCO$_3$ (aq) and brine. The crude material was purified by flash-chromatography on silica using a gradient of 0% to 40% EtOAc in Heptane. The obtained material was the further purified by HPLC to afford the subtitle compound as a yellow sticky oil. Yield 1.6 g (49%)

$^1$H-NMR (400 Mhz, CDCl3): δ 9.44 (d, 1H), 8.81 (s, 1H), 8.20 (d, 1H), 7.98 (d, 1H), 7.89 (t, 1H), 7.67 (t, 1H), 5.53 (brd, 1H), 5.42 (m, 1H), 1.48 (d, 3H), 1.47 (s, 9H).

APCI-MS m/z: 301.1 [MH$^+$]

Example 43

N-((1R,2S)-1-(2,3-dihydrobenzo[b][1,4]dioxin-6-yl)-1-(1-(4-fluorophenyl)-1H-indazol-5-yloxy)propan-2-yl)cyclopropanesulfonamide

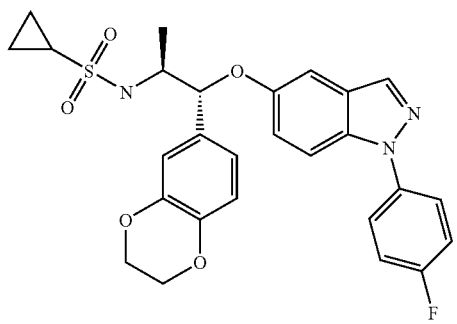

(1R,2S)-1-(2,3-dihydrobenzo[b][1,4]dioxin-6-yl)-1-(1-(4-fluorophenyl)-1H-indazol-5-yloxy)propan-2-amine (43a, 102 mg, 0.24 mmol) and DIPEA (170 µL, 0.97 mmol) was dissolved in NMP (2 mL). cyclopropanesulfonyl chloride (40 µL, 0.39 mmol) was added and the reaction mixture was stirred at room temperature for 1 hour. The reaction mixture was diluted with water (10 mL) and extracted with EtOAc (2×10 mL), the organic phase was washed with brine, dried (Na$_2$SO$_4$), filtered and evaporated to give an oily residue (NMP residues). The crude material was further purified by HPLC. Yield 80 mg (62%)

$^1$H-NMR (300 MHz, DMSO-d6): δ 8.18 (d, 1H), 7.79-7.67 (m, 3H), 7.46-7.32 (m, 3H), 7.21 (dd, 1H), 7.12 (d, 1H), 6.89-6.81 (m, 3H), 5.21 (d, 1H), 4.20 (s, 4H), 3.67 (m, 1H), 2.39 (m, 1H), 1.22 (d, 3H), 0.90-0.81 (m, 4H).

APCI-MS m/z: 524.1 [MH$^+$]

(1R,2S)-1-(2,3-dihydrobenzo[b][1,4]dioxin-6-yl)-1-(1-(4-fluorophenyl)-1H-indazol-5-yloxy)propan-2-amine trifluoroacetate (43a)

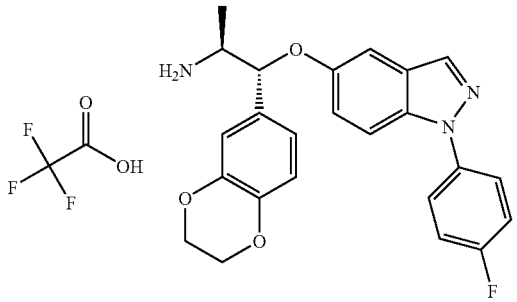

The subtitle compound was prepared following the procedure described in Example 1. Starting from (1R,2S)-2-amino-1-(2,3-dihydrobenzo[b][1,4]dioxin-6-yl)propan-1-ol hydrochloride (43b, 1.46 g, 5.94 mmol), 1-(4-fluorophenyl)-5-iodo-1H-indazole (2.4 g, 7.10 mmol), cesium carbonate (5.8 g, 17.80 mmol) and CuI (0.23 g, 1.21 mmol) in butyronitrile (18 mL). The reaction tube was capped and flushed with argon, the reaction mixture was stirred at +100° C. for 16 hours. Final purification was made by HPLC. Yield 1.16 g (36%)

$^1$H-NMR (300 MHz, DMSO-d6): δ 8.22 (d, 1H), 8.13 (brs, 3H), 7.79-7.69 (m, 3H), 7.41 (m, 2H), 7.27 (dd, 1H), 7.15 (d, 1H), 6.94-6.82 (m, 3H), 5.51 (d, J=3.32 Hz, 1H), 4.21 (s, 4H), 3.68 (m, 1H), 1.17 (d, 3H)

APCI-MS m/z: 420.1 [MH$^+$-TFA]

(1R,2S)-2-amino-1-(2,3-dihydrobenzo[b][1,4]dioxin-6-yl)propan-1-ol hydrochloride (43b)

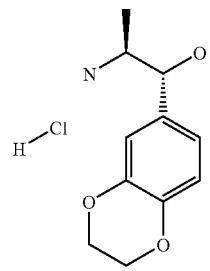

Following the procedure described for preparation of 29b. Starting from tert-butyl [(1S,2R)-2-(2,3-dihydro-1,4-benzodioxin-6-yl)-2-hydroxy-1-methylethyl]carbamate (43c, 3.76 g, 12.23 mmol), 2-propanol (12 mL, 157.75 mmol) and aluminium isopropoxide (0.5 g, 2.45 mmol) in toluene (22 mL) stirred at +50° C. under argon for 16 hours. Work up and purification by flash-chromatography. EtOAc:Hexane (1:2) as eluent afforded 3.19 g (84%) of the intermediate BOC-protected subtitle compound. APCI-MS m/z: 236, 210, 192, compound not stable in LC/MS system.

Deprotection of the BOC group afforded the subtitle compound as a hygroscopic salt.

Yield 2.10 g (70%)

¹H-NMR (300 MHz, DMSO-d6): δ 8.01 (brs, 3H), 6.87-6.75 (m, 3H), 5.93 (brd, 1H), 4.79 (brt, 1H), 4.22 (s, 4H), 3.32 (m, 1H), 0.95 (d, 3H).
APCI-MS m/z: 210 [MH⁺-HCl]

tert-butyl [(1S,2R)-2-(2,3-dihydro-1,4-benzodioxin-6-yl)-2-hydroxy-1-methylethyl]-carbamate (43c)

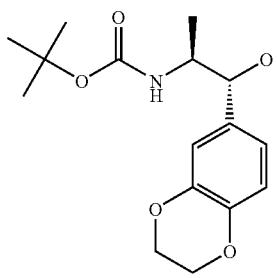

Isopropylmagnesium chloride, 2M in THF (6.5 mL, 13.00 mmol) was added to a suspension of (S)-tert-butyl 1-(methoxy(methyl)amino)-1-oxopropan-2-ylcarbamate (3 g, 12.92 mmol) in THF (30 mL) keeping the temperature below −10° C. (2,3-dihydrobenzo[b][1,4]dioxin-6-yl)magnesium bromide, 0.7M in THF (20 mL, 14.00 mmol) was added. The reaction mixture was stirred at room temperature for 17 hours. 1N HCl (300 mL) was cooled on ice bath to +10° C., the reaction mixture was poured into the acidic water solution and extracted with TBME=tert-butyl methyl ether. The ether phases were washed with water, brine and dried (Na₂SO₄). Filtration and evaporation of solvents afforded a crude product as a slightly yellow oil that was purified by flash chromatography using TBME:Heptane=1:2 as eluent.
Yield 3.76 g (95%) as a slightly yellow sticky oil/gum.
1H-NMR (300 MHz, DMSO-d6): δ 7.50 (dd, 1H), 7.46 (d, 1H), 7.23 (d, 1H), 6.97 (d, 1H), 4.97 (m, 1H), 4.30 (m, 4H), 1.36 (s, 9H), 1.19 (d, 3H).
APCI-MS m/z: 208 [MH⁺-BOC]

Example 44

Cyclopropanesulfonic acid N-{1-[6-methoxypyridin-3-yl]-1-[(1-pyridin-2-yl-1H-indazol-5-yl)oxy]propan-2-yl}amide

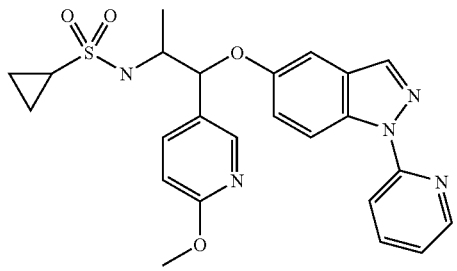

To a stirred solution of 1-[6-methoxypyridin-3-yl]-1-[1-(pyridin-2-yl)indazol-5-yl]oxypropan-2-amine (50 mg, 130 μmol) in dichloromethane (5 mL) was added triethylamine (44 μl), followed by cyclopropane sulfonic acid chloride (28 mg, 200 μmol) and DMAP (1.6 mg, 13 μmol). The stirring was continued for 20 min at room temp The reaction mixture was poured into sat. NH₄Cl solution and extracted with dichloromethane then the solvent was removed i.vac., and the product purified by chromatography on silica gel. Yield 24 mg as a racemic mixture of two diastereomeres (37%).
ESI+MS: m/z 480 [MH⁺]
¹H-NMR (CDCl₃); δ=8.74 (d, 1H), 8.49 (d, 1H), 8.24 (d, 0.5H), 8.20 (d, 0.5H), 8.01 (s, 1H), 8.00 (d, 1H), 7.80 (ddd, 1H), 7.66 (dd, 0.5H), 7.59 (dd, 0.5H), 7.21 (dd, 0.5H), 7.18 (dd, 0.5H), 7.13 (m, 1H), 7.0 (d, 0.5H), 6.98 (d, 0.5H), 6.75 (d, 1H), 5.42 (d, 0.5H), 5.22 (d, 0.5H), 4.66 (d, 0.5H), 4.58 (d, 0.5H), 3.94 (m, 1H), 3.92 (s, 3H), 2.43 (dddd, 0.5H), 2.18 (dddd, 0.5H), 1.45 (d, 1.5H), 1.33 (d, 1.5H), 1.20-0.78 (m, 4H).

1-[6-Methoxypyridin-3-yl]-1-[1-(pyridin-2-yl)indazol-5-yl]oxypropan-2-amine

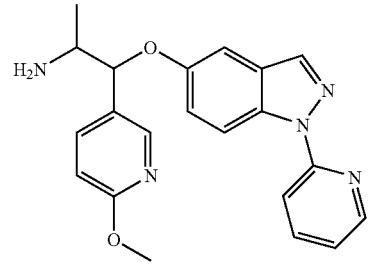

The title compound was prepared essentially by the method described by Job & Buchwald: Org. Lett. 2002, 4 (21), 3703-3706.
5-Iodo-1-(2-pyridinyl)indazole (2.82 g, 8.8 mmole), 2-Amino-1-[6-methoxypyridin-3-yl]propan-1-ol (1.6 g, 8.8 mmol, mixture of diastereomers), copper(I)iodide (167 mg, 0.88 mmol) and caesium carbonate (5.72 g, 17.6 mmole) was suspended in butyronitrile (6 mL) and toluene (12 mL). The reaction vessel was capped and the mixture was stirred at 130° C. for three days. The reaction mixture was diluted with dichloromethane and filtered through a path of cellites. Then the solvent was removed i.vac., and the product purified by chromatography on silica gel. Yield 1.2 g (36%) as a racemic mixture of two diastereomeres.
ESI+MS: m/z 376 [MH⁺]
¹H-NMR (CDCl₃); δ=8.70 (d, 0.5H), 8.68 (d, 0.5H), 8.47 (d, 1H), 8.20 (d, 0.5H), 8.17 (d, 0.5H), 7.99 (s, 1H), 7.98 (d, 1H), 7.79 (ddd, 1H), 7.62 (dd, 0.5H), 7.59 (dd, 0.5H), 7.20 (dd, 1H), 7.12 (m, 1H), 7.03 (d, 0.5H), 6.98 (d, 0.5H), 6.75 (d, 1H), 5.08 (br., 0.5H), 4.91 (br., 0.5H), 3.91 (s, 3H), 3.50 (br., 3H), 1.24 (br., 1.5H), 1.11 (br., 1.5H).

2-Amino-1-[6-methoxypyridin-3-yl]propan-1-ol

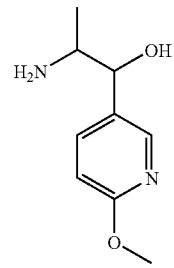

1-(6-methoxypyridin-3-yl)-2-nitro-propan-1-ol (2.20 g, 10.37 mmol) was dissolved in methanol (410 mL) and hydrogenated using a H-Cube™ hydrogenation reactor (THALES nanotechnology) equipped with a cartridge of 10% Pd/C. The flow rate was set to 0.8 mL/min, temperature 80° C. and full the hydrogen production at full mode. After evaporation of the solution diastereomers can be separated on preparative HPLC (XTerrra $C_{18}$, 19×50 mm) using a gradient of 5-30% acetonitrile in water (+1% $NH_3$) gave the pure subtitle compound (448 mg, 24%).

$^1$H-NMR (400 MHz, DMSO-$d_6$): δ=8.05 (1H, d); 7.63 (1H, dd); 6.76 (1H, d); 4.29 (1H, d); 3.82 (3H, s); 2.90 (1H, quintet); 0.87 (3H, d).

APCI-MS: m/z 183.0 [MH$^+$].

1-(6-methoxypyridin-3-yl)-2-nitro-propan-1-ol

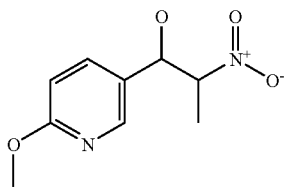

To a round bottom flask was added anhyrous magnesium sulphate (4.77 g, 40 mmol) and nitroethane (15 ml) The flask was evacuated and filled with argon. The reaction mixture was stirred vigorously to get a homogeneous suspension before 6-methoxynicotinaldehyde (2.37 g, 18 mmol in 5 mL nitroethane) was added. After stirring in 5 min 2,5,8,9-tetraaza-1-phosphabicyclo[3.3.3]undecane,2,8,9-tris(1-methylethyl) (1082 mg, 3.6 mmol) was added. The reaction mixture was stirred overnight at room temperature before it was purified by flash chromatography (SiO$_2$, heptane-ethylacetate). Yield 2.22 g, 58%.

APCI-MS: m/z 213.1 [MH$^+$].

5-Iodo-1-(2-pyridinyl)indazole

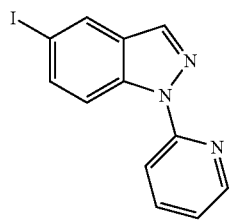

Cesiumcarbonate (29.86 g, 91.6 mmol) is added to a suspension of 2-fluoro-5-iodobenzaldehyde (11.45 g, 45.8 mmol) and 2-pyridylhydrazine (5 g, 45.8 mmol) in 230 mL N-methylpyrrolidon. The reaction mixture is stirred two hours at room temperature. After checking that the hydrazone has been formed ($^1$H-NMR) the reaction mixture is heated for three hours at 150° C. The reaction mixture is allowed to cool down and the dark brown suspension is poured into ice water. After vigorously stirring at room temperature for 15 minutes the mixture is extracted with ethyl acetate. The organic phase is washed with brine, dried over Na$_2$SO$_4$, the solvent is removed i.vac., and the product purified by chromatography on silica gel. Yield 4.8 g (33%).

ES+MS: 322 (MH+)

$^1$H-NMR (CDCl$_3$); δ=7.18 (ddd, 1H), 7.75 (dd, 1H), 7.84 (ddd, 1H), 8.05 (d, 1H), 8.11 (s, 1H), 8.14 (d, 1H), 8.53 (m, 1H), 8.66 (1H).

Example 45

Cyclopropanesulfonic acid N-{1-[6-methoxypyridin-3-yl]-1-[(1-pyridin-3-yl-1H-indazol-5-yl)oxy]propan-2-yl}amide

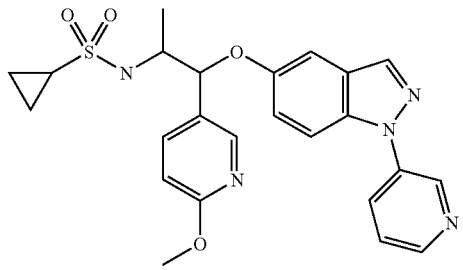

To a stirred solution of 1-[6-methoxypyridin-3-yl]-1-[1-(pyridin-3-yl)indazol-5-yl]oxypropan-2-amine (45 mg, 120 μmol) in dichloromethane (4.5 mL) was added triethylamine (40 μl), followed by cyclopropane sulfonic acid chloride (25 mg, 180 μmol) and DMAP (1.5 mg, 12 μmol). The stirring was continued for 20 hours at room temp. The reaction mixture was poured into sat. NH$_4$Cl solution and extracted with dichloromethane, then the solvent was removed i.vac., and the product purified by chromatography on silica gel. Yield 4 mg as a racemic mixture of two diastereomeres (7%).

ES+MS: m/z 480 [MH$^+$]

$^1$H-NMR (CDCl$_3$); δ=9.03 (br., 1H), 8.60 (br., 1H), 8.24 (d, 0.5H), 8.20 (d, 0.5H), 8.07 (s, 0.5H), 8.06 (s, 0.5H), 8.03 (d, 1H), 7.66 (dd, 0.5H), 7.64 (d, 1H), 7.59 (dd, 0.5H), 7.48 (ddd, 1H), 7.19 (dd, 0.5H), 7.16 (dd, 0.5H), 7.05 (d, 0.5H), 7.02 (d, 0.5H), 6.76 (d, 1H), 5.42 (d, 0.5H), 5.22 (d, 0.5H), 4.71 (d, 0.5H), 4.60 (d, 0.5H), 3.93 (s, 3H), 3.92 (m, 1H), 2.44 (dddd, 0.5H), 2.19 (dddd, 0.5H), 1.43 (d, 1.5H), 1.33 (d, 1.5H), 1.24-0.78 (m, 4H).

1-[6-Methoxypyridin-3-yl]-1-[1-(pyridin-3-yl)indazol-5-yl]oxypropan-2-amine

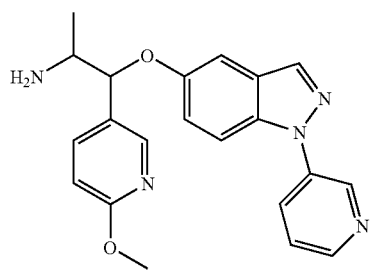

5-Iodo-1-(3-pyridinyl)indazole (750 mg, 2.3 mmole), 2-Amino-1-[6-methoxypyridin-3-yl]propan-1-ol (410 mg, 2.2 mmol), copper(I)iodide (42 mg, 0.22 mmol) and caesium carbonate (1.45 g, 4.5 mmole) were suspended in butyronitrile (2.4 mL) and toluene (4.8 mL). The reaction vessel was capped and the mixture was stirred at 130° C. for 20 hours.

Then the solvent was removed i.vac., and the product purified by chromatography on silica gel. Yield 254 mg (3 0%) as a racemic mixture of two diastereomeres.

ESI+MS: m/z 376 [MH+]

¹H-NMR (CDCl₃); δ=9.01 (br., 1H), 8.57 (d, 1H), 8.19 (d, 0.5H), 8.17 (d, 0.5H), 8.04 (s, 1H), 8.01 (m, 1H), 7.59 (m, 2H), 7.46 (ddd, 1H), 7.18 (d, 0.5H), 7.14 (d, 0.5H), 7.05 (d, 0.5H), 7.02 (d, 0.5H), 6.75 (d, 1H), 5.16 (d, 0.5H), 5.15 (d, 0.5H), 3.93 (s, 3H), 3.13 (dq, 0.5H), 3.11 (dq, 0.5H), 1.20 (d., 1.5H), 1.10 (d, 1.5H).

5-Iodo-1-pyridin-3-yl1H-indazole

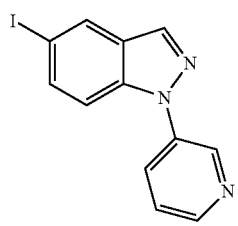

Cesiumcarbonate (26.84 g, 82.38 mmol) is added to a suspension of 2-fluoro-5-iodobenzaldehyde (6.87 g, 27.46 mmol) and 3-pyridylhydrazine dihydrochloride (5 g, 27.46 mmol) in 136 mL N-methylpyrrolidon. The reaction mixture is stirred overnight at room temperature. After checking that the hydrazone has been formed (¹H-NMR) the reaction mixture is heated for four hours at 160° C. The reaction mixture is allowed to cool down and the dark brown suspension is poured on 1000 mL ice water. After vigorously stirring at room temperature for 45 minutes, the precipitated product is sucked off via a glass microfibre filter, washed with water and dried at the evaporator at 45° C. 8.28 g (93.9%) of the title compound are obtained.

MS (CI+): m/z 322 (M+)

¹H-NMR (400 MHz, DMSO [d6]): δ=7.62 (1H), 7.72 (2H), 8.20 (1H), 8.32 (1H), 8.49 (1H), 8.61 (1H), 9.01 (1H).

Example 46

Cyclopropanesulfonic acid N-{1-[2-methoxypyridin-4-yl]-1-[(1-pyridin-3-yl-1H-indazol-5-yl)oxy]propan-2-yl}amide

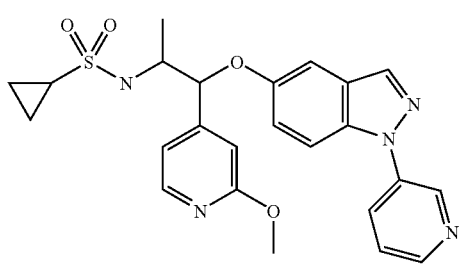

To a stirred solution of 1-[2-methoxypyridin-4-yl]-1-[1-(pyridin-3-yl)indazol-5-yl]oxypropan-2-amine (41 mg, 110 μmol) in dichloromethane (4 ml) was added triethylamine (36 μl), followed by cyclopropanesulfonic acid chloride (23 mg, i 60 μmol) and DMAP (1.3 mg, 11 μmol).The stirring was continued for 20 h at room temp. The reaction mixture was poured into sat. NH₄Cl solution and extracted with dichloromethane then the solvent was removed i.vac., and the product purified by chromatography on silica gel. Yield 4 mg (7.6%) as a racemic mixture of one diastereomer.

ES+MS: m/z 480 [MH+]

¹H-NMR (CDCl₃); δ=9.04 (d, 1H), 8.61 (d, 1H), 8.18 (d, 1H), 8.06 (s, 1H), 7.66 (d, 1H), 7.49 (dd, 1H), 7.19 (dd, 1H), 6.97 (d, 1H), 6.90 (dd, 1H), 6.76 (s, 1H), 5.42 (d, 1H), 4.74 (d, 1H), 3.95 (m, 1H), 3.92 (s, 3H), 2.44 (dddd, 1H), 1.29 (d., 3H), 1.21 (m, 1H), 1.01 (m, 3H).

1-[2-Methoxypyridin-4-yl]-1-[1-(pyridin-3-yl)indazol-5-yl]oxypropan-2-amine

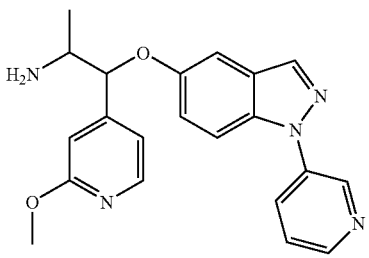

The title compound was prepared essentially by the method described by Job & Buchwald: Org. Lett. 2002, 4 (21), 3703-3706.

5-Iodo-1-(3-pyridinyl)indazole (750 mg, 2.3 mmole), 2-Amino-1-[6-methoxypyridin-4-yl]propan-1-ol (410 mg, 2.2 mmol), copper(I)iodide (42 mg, 0.22 mmol) and caesium carbonate (1.45 g, 4.5 mmole) were suspended in butyronitrile (2.4 mL) and toluene (4.8 mL). The reaction vessel was capped and the mixture was stirred at 130° C. for 20 hours. Then the solvent was removed i.vac., and the product purified by chromatography on silica gel. Yield 243 mg (30%) as a racemic mixture of one diastereomere.

¹H-NMR (CDCl₃); δ=9.01 (d, 1H), 8.58 (dd, 1H), 8.12 (d, 1H), 8.04 (s, 1H), 8.02 (m, 1H), 7.63 (d, 2H), 7.46 (dd, 1H), 7.18 (dd, 1H), 6.96 (d, 1H), 6.85 (dd, 1H), 6.72 (s, 1H), 4.14 (d, 1H), 3.93 (s, 3H), 3.12 (dq, 1H), 1.27 (d, 3H).

2-Amino-1-[2-methoxypyridin-4-yl]propan-1-ol

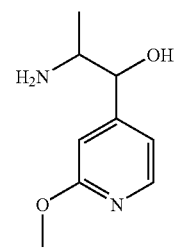

Ammonium formate (1.13 g, 18 mmol) and palladium on charcoal (10%, 175 mg) is added to a solution of 1-(2-methoxypyridin-4-yl)-2-nitro-propan-1-ol (760 mg, 3.6 mmol) in 17.5 ml THF and 17.5 ml methanol. The reaction mixture is stirred overnight at room temperature, filtered through a path of cellites and concentrated. Yield 620 mg of a racemic mixture of two diastereomers, 95%.

¹H-NMR (CDCl₃); δ=8.11 (d, 1H), 6.85 (d, 0.5H), 6.83 (d, 0.5H), 6.74 (s, 0.5H), 6.73 (s, 0.5H), 4.53 (d, 0.5H), 4.22 (d, 0.5H), 3.93 (s, 3H), 3.24 (dq, 0.5H), 3.03 (d, 0.5H), 1.63 (br. 2H), 1.11 (d, 1.5H), 0.90 (d, 1.5H).

1-(2-Methoxypyridin-4-yl)-2-nitropropan-1-ol

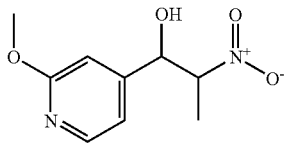

To a round bottom flask was added anhyrous magnesium sulfate (0.97 g, 8 mmol) and nitroethane (1.34 ml, 18.7 mmol) The flask was evacuated and filled with argon. The reaction mixture was stirred vigorously to get a homogeneous suspension before 2-methoxypyridine-4-carboxaldehyde (500 mg, 3.65 mmol) was added. After stirring in 5 min 2,5,8,9-tetraaza-1-phosphabicyclo[3.3.3]undecane,2,8,9-tris(1-methylethyl) (109 mg, 0.36 mmol) was added. The reaction mixture was stirred overnight at room temperature before it was purified by flash chromatography (SiO₂, diethyl ether). Yield 770 mg of a racemic mixture of two diastereomers, 99%.

¹H-NMR (CDCl₃); δ=8.17 (d, 0.5H), 8.15 (d, 0.5H), 6.87 (d, 0.5H), 6.85 (d, 0.5H), 6.80 (s, 0.5H), 6.75 (s, 0.5H), 5.42 (d, 0.5H), 4.98 (d, 0.5H), 4.73 (dq, 0.5H), 4.67 (d, 0.5H), 3.94 (s, 3H), 1.47 (d, 1.5H), 1.40 (d, 1.5H).

Example 47

Cyclopropanesulfonic acid N-{1-[2-methoxypyridin-4-yl]-1-[(1-pyridin-2-yl-1H-indazol-5-yl)oxy]butan-2-yl}amide

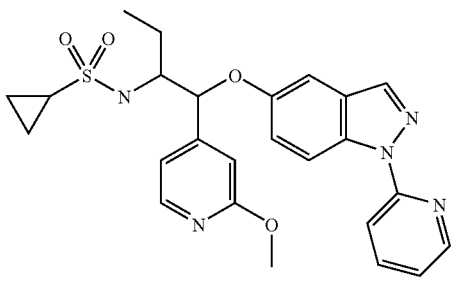

To a stirred solution of 1-[2-methoxypyridin-4-yl]-1-[(1-pyridin-2-yl-1H-indazol-5-yl)oxy]butan-2-amine (122 mg, 310 µmol) in dichloromethane (11 ml) was added triethylamine (100 µl), followed by cyclopropanesulphonic acid chloride (66 mg, 470 µmol) and DMAP (3.8 mg, 31 µmol). The stirring was continued for 48 h at room temp. The reaction mixture was poured into sat. NH₄Cl solution and extracted with dichloromethane then the solvent was removed i.vac., and the product purified by chromatography on silica gel. Yield 10 mg (6.5%) as a racemic mixture of two diastereomeres.

ESI+MS: m/z 494 [MH⁺]

¹H-NMR (CDCl₃); δ=8.76 (d, 1H), 8.49 (d, 1H), 8.21 (d, 0.5H), 8.16 (d, 0.5H), 8.02 (s, 1H), 8.00 (d, 1H), 7.81 (ddd, 1H), 7.19 (dd, 1H), 7.13 (m, 1H), 6.94 (m, 2H), 6.83 (br, 0.5H), 6.77 (br. 0.5H), 5.47 (d, 0.5H), 5.29 (d, 0.5H), 4.62 (d, 0.5H), 4.56 (d, 0.5H), 3.94 (m, 1H), 3.91 (s, 3H), 2.47 (dddd, 0.5H), 2.28 (dddd, 0.5H), 1.94 (m, 1H), 1.64 (m, 1H), 1.22 (t, 1.5H), 1.09 (t, 1.5H), 0.98 (m, 2.5H), 0.78 (m, 0.5H).

1-[2-Methoxypyridin-4-yl]-1-[1-(pyridin-2-yl)indazol-5-yl]oxybutan-2-amine

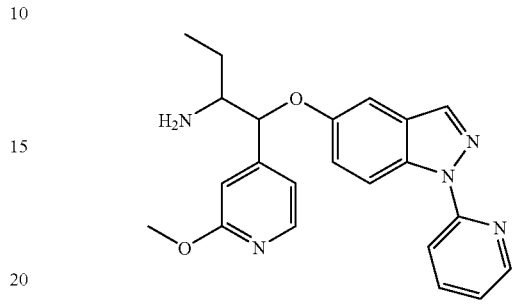

The title compound was prepared essentially by the method described by Job & Buchwald: Org. Lett. 2002, 4 (21), 3703-3706.

5-Iodo-1-(2-pyridinyl)indazole (830 mg, 2.6 mmol), 2-amino-1-[2-methoxypyridin-4-yl]butan-1-ol (510 mg, 2.6 mmol), copper(I)iodide (49 mg, 0.26 mmol) and caesium carbonate (1.68 g, 5.2 mmol) were suspended in butyronitrile (1.7 mL) and toluene (3.5 mL). The reaction vessel was capped and the mixture was stirred at 130° C. for 60 hours. Then the solvent was removed i.vac., and the product purified by chromatography on silica gel. Yield 680 mg (67%) as a racemic mixture of two diastereomeres.

¹H-NMR (CDCl₃); δ=8.71 (d, 1H), 8.48 (d, 1H), 8.15 (d, 0.5H), 8.11 (d, 0.5H), 8.00 (s, 1H), 7.99 (d, 1H), 7.80 (dd, 1H), 7.22 (dd, 1H), 7.13 (dd, 1H), 6.94 (m, 2H), 6.77 (s, 0.5H), 6.72 (s, 0.5H), 5.22 (d, 0.5H), 5.05 (d, 0.5H), 3.93 (s, 3H), 3.12 (m, 0.5H), 2.98 (m, 0.5H), 2.36 (br., 2H) 1.60 (m, 2H), 1.02 (t, 1.5H), 0.98 (t, 1.5H).

2-Amino-1-[2-methoxypyridin-4-yl]butan 1-ol

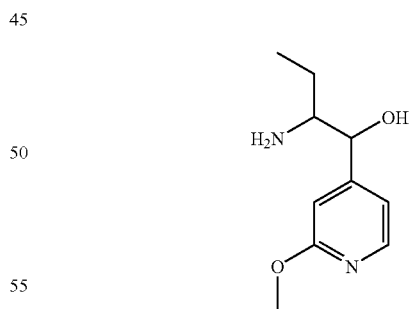

Ammonium formate (2.5 g, 40 mmol) and palladium on charcoal (10%, 390 mg) is added to a solution of 1-(2-methoxypyridin-4-yl)-2-nitrobutan-1-ol (1.7 g, 7.5 mmol) in 38 ml THF and 38 ml methanol. The reaction mixture is stirred overnight at room temperature, filtered through a path of cellites and concentrated. Yield 620 mg of a racemic mixture of two diastereomers, 42%.

¹H-NMR (CDCl₃); δ=8.11 (d, 0.5H), 8.10 (d, 0.5H), 6.84 (d, 0.5H), 6.83 (d, 0.5H), 6.74 (s, 0.5H), 6.72 (s, 0.5H), 4.61 (d, 0.5H), 4.31 (d, 0.5H), 3.92 (s, 3H), 2.95 (ddd, 0.5H), 2.77

(ddd, 0.5H), 2.33 (br. 2H), 1.55 (m, 0.5H), 1.38 (m, 0.5H), 1.30 (m, 0.5H), 1.12 (m, 0.5H), 0.96 (t, 1.5H), 0.90 (t, 1.5H).

1-(2-Methoxypyridin-4-yl)-2-nitrobutan-1-ol

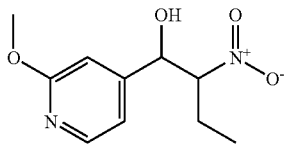

To a round bottom flask was added anhyrous magnesium sulphate (3.09 g, 25.7 mmol) and nitro propane (5.35 ml, 60 mmol) The flask was evacuated and filled with argon. The reaction mixture was stirred vigorously to get a homogeneous suspension before 2-methoxypyridine-4-carboxaldehyde (500 mg, 3.65 mmol) in 5 ml was added. After stirring in 5 min 2,8,9-tris(1-methylethyl)-2,5,8,9-tetraaza-1-phosphabicyclo[3.3.3]undecane (350 mg, 1.2 mmol) was added in 5 ml nitro propan. The reaction mixture was stirred overnight at room temperature before it was purified by flash chromatography (SiO$_2$, diethyl ether). Yield 1.7 g of a racemic mixture of two diastereomers, 64%.

$^1$H-NMR (CDCl$_3$); δ=8.17 (d, 0.5H), 8.15 (d, 0.5H), 6.87 (d, 1H), 6.79 (s, 0.5H), 6.74 (s, 0.5H), 5.19 (d, 0.5H), 4.98 (d, 0.5H), 4.58 (ddd, 0.5H), 4.55 (ddd, 0.5H), 3.94 (s, 3H), 2.16 (m, 0.5H), 1.90 (m, 0.5H), 1.78 (m, 0.5H), 1.55 (m, 0.5H), 0.93 (t, 1.5H), 0.92 (t, 1.5H).

Example 48

1-Methylimidazole-4-sulfonic acid N-[(1R,2S)-1-[1-(4-fluorophenyl)indazol-5-yl]oxy-1-phenyl-propan-2-yl]amide

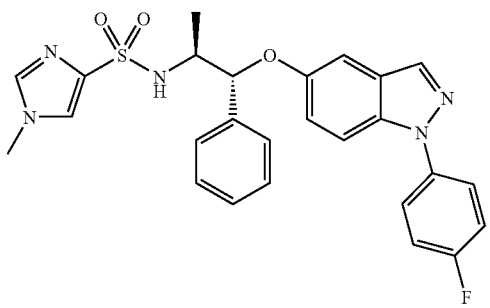

To (1R,2S)-1-[1-(4-fluorophenyl)indazol-5-yl]oxy-1-phenylpropan-2-amine (1a, 60 mg, 0.14 mmol) 130 μmol) in dichloromethane (6 mL) was added triethylamine (55 μl), followed by 1-methylimidazole-4-sulfonyl chloride (36 mg, 200 μmol) and DMAP (2 mg, 17 μmol). The stirring was continued for 18 hours at room temperature and the reaction mixture was poured into water and extracted with dichloromethane. The combined organic phases were washed with brine, died over sodium sulphate, the solvent was removed i.vac., and the product purified by chromatography on silica gel.

Yield 39 mg (46%). MS (CI+): m/z 506 (MH+).

$^1$H-NMR (300 MHz, CDCl$_3$) δ=7.93 (s, 1H), 7.62 (dd, 2H), 7.53 (d, 1H), 7.40 (d, 2H), 7.33 (m, 4H), 7.28 (t, 1H), 7.20 (t, 2H), 7.14 (dd, 1H), 6.85 (d, 1H), 5.46 (d, 1H), 5.24 (d, 1H), 3.93 (dq, 1H), 3.63 (s, 3H), 1.12 (d, 3H).

Example 49

3,5-Dimethylisooxazole-4-sulfonic acid N-[(1R,2S)-1-[1-(4-fluorophenyl)indazol-5-yl]oxy-1-phenyl-propan-2-yl]amide

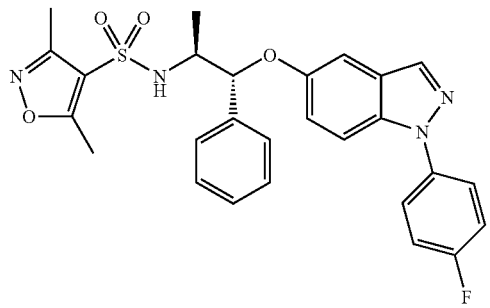

To (1R,2S)-1-[1-(4-fluorophenyl)indazol-5-yl]oxy-1-phenylpropan-2-amine (1a, 60 mg, 0.14 mmol) 130 μmol) in dichloromethane (6 mL) was added triethylamine (55 μl), followed by 3,5-dimethylisooxazole-4-sulfonyl chloride (39 mg, 200 μmol) and DMAP (2 mg, 17 μmol). The stirring was continued for 18 hours at room temperature and the reaction mixture was poured into water and extracted with dichloromethane. The combined organic phases were washed with brine, died over sodium sulphate, the solvent was removed i.vac., and the product purified by chromatography on silica gel.

Yield 31 mg (36%). MS (CI+): m/z 521 (MH+).

$^1$H-NMR (300 MHz, CDCl$_3$) δ=7.96 (s, 1H), 7.62 (dd, 2H), 7.54 (d, 1H), 7.35 (m, 3H), 7.28 (m, 1H), 7.21 (t, 2H), 7.04 (dd, 1H), 6.87 (d, 1H), 5.26 (d, 1H), 4.97 (d, 1H), 3.77 (dq, 1H), 2.64 (s, 3H), 2.38 (s, 3H), 1.22 (d, 3H).

Assay

Human Glucocorticoid Receptor (GR) Assay

The assay is based on a commercial kit from Panvera/Invitrogen (Part number P2893). The assay technology is fluorescence polarization. The kit utilises recombinant human GR (Panvera, Part number P2812), a Fluoromone™ labelled tracer (GS Red, Panvera, Part number P2894) and a Stabilizing Peptide 10X (Panvera, Part number P2815). The GR and Stabilizing Peptide reagents are stored at −70° C. while the GS Red is stored at −20° C. Also included in the kit are 1M DTT (Panvera, Part number P2325, stored at −20° C.) and GR Screening buffer 10X (Panvera, Part number P2814, stored at −70° C. initially but once thawed stored at room temperature). Avoid repeated freeze/thaws for all reagents. The GR Screening buffer 10X comprises 100 mM potassium phosphate, 200 mM sodium molybdate, 1 mM EDTA and 20% DMSO.

Test compounds (1 μL) and controls (1 μL) in 100% DMSO were added to black polystyrene 384-well plates (Greiner low volume black flat-bottom, part number 784076). 0% control was 100% DMSO and 100% control was 10 μM Dexamethasone. Background solution (8 μL; assay buffer 10X, Stabilizing Peptide, DTT and ice cold MQ water) was added to the background wells. GS Red solution (7 μL; assay buffer 10X, Stabilizing Peptide, DTT, GS Red and ice cold water) was added to all wells except background wells. GR solution (7 μL; assay buffer 10X, Stabilizing Peptide, DTT, GR and ice cold water) was added to all wells. The plate was sealed and incubated in a dark at room temperature for 2 hours. The plate was read in an Analyst plate reader (LJL Biosystems/Molecular Devices Corporation) or other similar plate reader capable of recording fluorescence polarization (excitation wavelength 530 nm, emission wavelength 590 nM and a dichroic mirror at 561 nm). The IC50 values were calculated using XLfit model 205.

| Example | GRhuFL_FP_v2 Mean IC50 (nM) |
|---|---|
| 1 | 6 |
| 2 | 6.9 |
| 3 | 90 |
| 4 | 4.9 |
| 5 | 2.3 |
| 6 | 5.9 |
| 7 | 4.6 |
| 8 | 4.6 |
| 9 | 3.2 |
| 10 | 6.5 |
| 11 | 6.9 |
| 12 | 2.8 |
| 13 | 5 |
| 14 | 4.3 |
| 15 | 5.4 |
| 16 | 6.4 |
| 17 | 5.7 |
| 18 | 4.3 |
| 19 | 5.1 |
| 20 | 8.7 |
| 21 | 9.9 |
| 22 | 2.7 |
| 23 | 9.5 |
| 24 | 7.6 |
| 25 | 7 |
| 26 | 77 |
| 27 | 6.3 |
| 28 | 6.3 |
| 29 | 21 |
| 30 | 330 |
| 31 | 6.4 |
| 32 | 7.6 |
| 33 | 170 |
| 34 | 2.5 |
| 35 | 6.2 |
| 36 | 4.3 |
| 37 | 17 |
| 38 | 4.8 |
| 39 | 280 |
| 40 | 13 |
| 41 | 250 |
| 42 | 3.6 |
| 43 | 2.3 |

The invention claimed is:

1. A compound of formula (I):

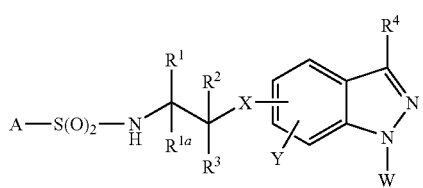

wherein:

A is $C_{1-10}$ alkyl, $C_{5-10}$ aryl, $C_{5-10}$ aryl$C_{1-6}$alkyl, $C_{5-10}$ heteroaryl, $C_{5-10}$ heteroaryl$C_{1-6}$alkyl, $C_{5-10}$ aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)OC$_{1-6}$alkyl, $C_{5-10}$ aryloxy$C_{1-10}$alkyl or NR$^5$R$^6$C$_{0-6}$alkyl whereby the aryl is optionally substituted with one or more substituents selected from B;

$R^1$ and $R^{1a}$ are independently selected from hydrogen, $C_{1-4}$alkyl, $C_{1-4}$haloalkyl, $C_{1-4}$hydroxyalkyl and $C_{1-4}$alkylOC$_{1-4}$alkyl;

$R^2$ is hydrogen or $C_{1-4}$alkyl;

$R^3$ is $C_{5-10}$ aryl$C_{0-3}$alkyl, $C_{5-10}$arylOC$_{0-3}$alkyl, or $C_{5-10}$heteroaryl$C_{0-3}$alkyl, each of which is optionally substituted by one or more B;

B is $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-3}$alkyl S(O)$_n$C$_{0-4}$alkyl, $C_{1-6}$haloalkyl, $C_{1-4}$haloalkoxy, halogen, nitro, cyano, $C_{1-4}$alkylOC$_{1-6}$alkyl, $C_{0-6}$alkyl OC$_{1-4}$alkylOC$_{0-4}$alkyl, $C_{0-6}$alkylC(O)C$_{0-6}$alkyl, $C_{0-4}$alkylC(O)OC$_{0-4}$alkyl, $C_{0-4}$alkylOC(O)C$_{0-4}$alkyl, NR$^5$R$^6$C$_{0-4}$alkyl, NR$^5$R$^6$C(O)C$_{0-4}$alkyl, NR$^5$R$^6$OC(O)C$_{0-4}$alkyl, NR$^5$R$^6$C(O)OC$_{0-4}$alkyl, R$^6$C(O)R$^5$NC$_{1-4}$alkyl, $C_{0-4}$alkylOC(O)C$_{0-4}$alkylNH, $C_{0-4}$alkylC(O)OC$_{0-4}$alkylNH, $C_{0-4}$alkylC(O)C$_{0-4}$alkylNH or NR$^5$R$^6$S(O)$_n$C$_{0-4}$alkyl;

$R^4$ is hydrogen, hydroxy, halogen, $C_{1-4}$ alkyl or $C_{1-4}$ haloalkyl;

W is hydrogen, $C_{3-7}$cycloalkyl, $C_{1-4}$alkyl, phenyl, thienyl, isoxazolyl, pyrazolyl, pyridinyl or pyrimidinyl all of optionally substituted with one or more substituents selected from halogen, $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl $C_{0-4}$thioalkyl, $C_{0-4}$alkylS(O)$_n$C$_{0-4}$alkyl, $C_{1-6}$haloalkyl, $C_{1-4}$haloalkoxy, halo, nitro, cyano, $C_{1-4}$alkyl OC$_{1-6}$alkyl, $C_{1-6}$alkylOC$_{1-6}$alkylOC$_{1-6}$alkyl, $C_{0-6}$alkylC(O)C$_{0-6}$alkyl, $C_{0-4}$alkylC(O)OC$_{0-4}$alkyl, $C_{1-4}$alkylOC(O)C$_{0-4}$alkyl, NR$^5$R$^6$C$_{0-4}$alkyl, NR$^5$R$^6$C(O)C$_{0-4}$alkyl, NR$^5$R$^6$C(O)OC$_{0-4}$alkyl, NR$^5$R$^6$OC(O)C$_{0-4}$alkyl, R$^6$C(O)R$^5$NC$_{0-4}$alkyl, $C_{0-4}$alkylOC(O)C$_{0-4}$alkylNH, $C_{0-4}$alkylC(O)C$_{0-4}$alkylNH and NR$^5$R$^6$S(O)$_n$C$_{0-4}$alkyl;

X is $CH_2$, O, S, S(O), S(O)$_2$ or NH;

Y is hydrogen, halogen, $C_{1-6}$ alkyl, $C_{1-4}$alkoxy, $C_{1-4}$thioalkyl, $C_{1-4}$haloalkyl, $C_{1-4}$alkoxyhalo, nitro, cyano, hydroxy, R$^5$C(O)$, R$^5$OC(O), R$^5$C(O)O, S(O)$_n$C$_{1-4}$alkyl, R$^5$R$^6$NS(O)$_n$, benzyloxy, imidazolyl, $C_{1-4}$alkylNHC(O), NR$^5$R$^6$C(O), $C_{1-4}$alkylC(O)NH or NR$^5$R$^6$;

$R^5$ and $R^6$ are independently selected from hydrogen, $C_{1-4}$ alkyl and $C_{3-7}$ cycloalkyl, or $R^5$ and $R^6$ form together a group (O)$C_{5-10}$ arylC(O)—; and n is 1 or 2, or a pharmaceutically acceptable salt thereof.

2. The compound according to claim 1, wherein A is $C_{5-10}$aryl, $C_{5-10}$aryl$C_{1-6}$alkyl, $C_{5-10}$aryl$C_{1-6}$alkoxy, or $C_{5-10}$ aryloxy$C_{1-10}$alkyl whereby the aryl is optionally substituted with one or more substituents selected from B.

3. The compound according to claim 1, wherein A is $C_{3-6}$cycloalkyl.

4. A compound of formula (I):

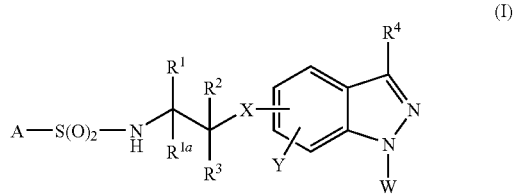

wherein:

A is $C_{1-10}$alkyl, $C_{5-10}$aryl, $C_{5-10}$aryl$C_{1-6}$, $C_{5-10}$ heteroaryl, $C_{5-10}$heteroaryl$C_{1-6}$alkyl, $C_{5-10}$aryl$C_{1-6}$alkoxy, $C_{1-10}$haloalkyl, $C_{3-7}$cycloalkyl, $C_{3-7}$cycloalkyl$C_{1-4}$alkyl, $C_{1-6}$alkylOC(O)$C_{1-6}$alkyl, $C_{1-6}$alkylC(O)O$C_{1-6}$alkyl, $C_{5-10}$ aryloxy$C_{1-10}$alkyl or NR$^5$R$^6$$C_{0-6}$alkyl whereby the aryl is optionally substituted with one or more substituents selected from B, wherein B is $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-3}$alkylS(O)$_n$$C_{0-4}$alkyl, $C_{1-6}$haloalkyl, $C_{1-4}$haloalkoxy, halogen, nitro, cyano, $C_{1-4}$alkylOC$_{1-6}$alkyl, $C_{0-6}$alkylOC$_{1-4}$-alkylOC$_{0-4}$alkyl, $C_{0-6}$alkylC(O)$C_{0-6}$alkyl, $C_{1-4}$alkylC(O)OC$_{0-4}$alkyl, $C_{1-4}$alkylOC(O)C$_{0-4}$alkyl, NR$^5$R$^6$$C_{0-4}$alkyl, NR$^5$R$^6$C(O)$C_{0-4}$alkyl, NR$^5$R$^6$OC(O)$C_{0-4}$alkyl, NR$^5$R$^6$C(O)OC$_{0-4}$alkyl, R$^6$C(O)R$^5$N$C_{0-4}$alkyl, $C_{0-4}$alkylOC(O)$C_{0-4}$alkylNH, $C_{0-4}$alkylC(O)OC$_{0-4}$alkylNH $C_{0-4}$alkylC(O)$C_{0-4}$alkylNH or NR$^5$R$^6$S(O)$_n$$C_{0-4}$alkyl;

R$^1$ and R$^{1a}$ are independently selected from hydrogen, $C_{1-4}$alkyl, $C_{1-4}$haloalkyl, $C_{1-4}$hydroxyalkyl and $C_{1-4}$alkylOC$_{1-4}$alkyl;

R$^2$ is hydrogen or $C_{1-4}$alkyl;

R$^3$ is phenyl or a dihydrobenzodioxinyl group;

wherein B is $C_{0-3}$hydroxyalkyl, $C_{1-4}$alkyl, $C_{1-4}$alkoxy, $C_{1-4}$alkylthio$C_{0-4}$alkyl, $C_{3-6}$cycloalkyl$C_{0-4}$thioalkyl, $C_{0-3}$alkylS(O)$_n$$C_{0-4}$alkyl, $C_{1-6}$haloalkyl, $C_{1-4}$haloalkoxy, halogen, nitro, cyano, $C_{1-4}$alkylOC$_{1-6}$alkyl, $C_{0-6}$alkylOC$_{1-4}$alkylOC$_{0-4}$alkyl, $C_{0-6}$alkylC(O)$C_{0-6}$alkyl, $C_{0-4}$alkylC(O)OC$_{0-4}$alkyl, $C_{0-4}$alkylOC(O)$C_{0-4}$alkyl, NR$^5$R$^6$$C_{0-4}$alkyl, NR$^5$R$^6$C(O)$C_{0-4}$alkyl, NR$^5$R$^6$OC(O)$C_{0-4}$alkyl, NR$^5$R$^6$C(O)OC$_{0-4}$alkyl, R$^6$C(O)R$^5$N$C_{0-4}$alkyl, $C_{0-4}$alkylOC(O)$C_{0-4}$alkylNH $C_{0-4}$alkylC(O)OC$_{0-4}$alkylNH, $C_{0-4}$alkylC(O)$C_{0-4}$alkylNH or NR$^5$R$^6$S(O)$_n$$C_{0-4}$alkyl; or B together with R3 form a dihydrobenzodioxinyl group;

R$^4$ is hydrogen, hydroxy, halogen, $C_{1-4}$ alkyl or $C_{1-4}$ haloalkyl;

W is hydrogen, $C_{3-7}$cycloalkyl, $C_{1-4}$alkyl, phenyl, thienyl, isoxazolyl, pyrazolyl, pyridinyl or pyrimidinyl all of optionally substituted with one or more substituents selected from halogen, $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl $C_{0-4}$thioalkyl, $C_{0-4}$alkylS(O)$_n$$C_{0-4}$alkyl, $C_{1-4}$haloalkyl, $C_{1-4}$haloalkoxy, halo, nitro, cyano, $C_{1-4}$alkyl OC$_{1-6}$alkyl, $C_{1-6}$alkylOC$_{1-6}$alkylOC$_{1-6}$alkyl, $C_{0-6}$alkylC(O)$C_{0-6}$alkyl, $C_{0-4}$alkylC(O)OC$_{0-4}$alkyl, $C_{0-4}$alkylOC(O)$C_{0-4}$alkyl, NR$^5$R$^6$$C_{0-4}$alkyl, NR$^5$R$^6$C(O)$C_{0-4}$alkyl, NR$^5$R$^6$C(O)OC$_{0-4}$alkyl, NR$^5$R$^6$OC(O)$C_{0-4}$alkyl, R$^6$C(O)R$^5$N$C_{0-4}$alkyl, $C_{0-4}$alkylOC(O)$C_{0-4}$alkylNH $C_{0-4}$alkylC(O)OC$_{0-4}$alkylNH, $C_{0-4}$alkylC(O)$C_{0-4}$alkylNH and NR$^5$R$^6$S(O)$_n$$C_{0-4}$alkyl;

X is CH$_2$, O, S(O), S(O)$_2$ or NH;

Y is hydrogen, halogen, $C_{1-6}$alkyl, $C_{1-4}$alkoxy, $C_{1-4}$thioalkyl, $C_{1-4}$haloalkyl, $C_{1-4}$alkoxyhalo, nitro, cyano, hydroxy, R$^5$C(O), R$^5$OC(O), R$^5$C(O)O, S(O)$_n$$C_{1-4}$alkyl, R$^5$R$^6$NS(O)$_n$, benzyloxy, imidazolyl, $C_{1-4}$alkylNHC (O), NR$^5$R$^6$C(O), $C_{1-4}$alkylC(O)NH or NR$^5$R$^6$;

R$^5$ and R$^6$ are independently selected from hydrogen, $C_{1-4}$ alkyl and $C_{3-7}$cycloalkyl, or R$^5$ and R$^6$ form together a group —(O)$C_{5-10}$arylC(O)—; and n is 1 or 2, or a pharmaceutically acceptable salt thereof.

5. The compound according to claim 1 or claim 4 wherein W is $C_{3-7}$cycloalkyl, $C_{1-4}$alkyl, phenyl or pyridinyl all of optionally substituted with one or more substituents selected from halogen.

6. The compound according to claim 1 or claim 4 wherein W is phenyl substituted with fluoro.

7. The compound according to claim 1 or claim 4 wherein R$^1$ is $C_{1-4}$alkyl, R$^{1a}$ is hydrogen, R$^2$ hydrogen, X is O and R$^3$ is $C_{5-10}$aryl, whereby aryl is optionally substituted by one or more B.

8. A compound selected from

N-[(1R,2S)-1-[1-(4-fluorophenyl)indazol-5-yl]oxy-1-phenyl-propan-2-yl]cyclopropanesulfonamide, N-[(1R,2S)-1-[1-(4-fluorophenyl)indazol-5-yl]oxy-1-phenyl-propan-2-yl]propane-1-sulfonamide, N-[(1R,2S)-1-[1-(4-fluorophenyl)indazol-4-yl]oxy-1-phenyl-propan-2-yl]cyclopropanesulfonamide, N-[(1R,2S)-1-[1-(6-fluoropyridin-3-yl)indazol-5-yl]oxy-1-phenyl-propan-2-yl]cyclopropanesulfonamide, N-[(1R,2S)-1-[1-(4-fluorophenyl)indazol-5-yl]oxy-1-phenyl-propan-2-yl]methanesulfonamide, N-[(1R,2S)-1-[1-(4-fluorophenyl)indazol-5-yl]oxy-1-phenyl-propan-2-yl]-1-phenyl-methanesulfonamide, 1,1,1-trifluoro-N-[(1R,2S)-1-[1-(4-fluorophenyl)indazol-5-yl]oxy-1-phenyl-propan-2-yl]methanesulfonamide, 5-[(1R,2S)-2-(dimethylsulfamoylamino)-1-phenyl-propoxy]-1-(4-fluorophenyl)indazole, N-[(1R,2S)-1-[1-(4-fluorophenyl)indazol-5-yl]oxy-1-phenyl-propan-2-yl]propane-2-sulfonamide, 2-(1,3-dioxoisoindol-2-yl)-N-[(1R,2S)-1-[1-(4-fluorophenyl)indazol-5-yl]oxy-1-phenyl-propan-2-yl]ethanesulfonamide, N-[(1R,2S)-1-[1-(4-fluorophenyl)indazol-5-yl]oxy-1-phenyl-propan-2-yl]-3-(4-methoxyphenoxy)propane-1-sulfonamide, N-[(1R,2S)-1-[1-(4-fluorophenyl)indazol-5-yl]oxy-1-phenyl-propan-2-yl]ethanesulfonamide, N-[(1R,2S)-1-[1-(4-fluorophenyl)indazol-5-yl]oxy-1-phenyl-propan-2-yl]pentane-2-sulfonamide N-[(1R,2S)-1-[1-(4-fluorophenyl)indazol-5-yl]oxy-1-phenyl-propan-2-yl]butane-2-sulfonamide, N-[(1R,2S)-1-[1-(4-fluorophenyl)indazol-5-yl]oxy-1-phenyl-propan-2-yl]butane-1-sulfonamide, N-[(1R,2S)-1-[1-(4-fluorophenyl)indazol-5-yl]oxy-1-phenyl-propan-2-yl]-2-methyl-propane-1-sulfonamide, N-[(1R,2S)-1-[1-(4-fluorophenyl)indazol-5-yl]oxy-1-phenyl-propan-2-yl]pentane-1-sulfonamide, 3,3,3-trifluoro-N-[(1R,2S)-1-[1-(4-fluorophenyl)indazol-5-yl]oxy-1-phenyl-propan-2-yl]propane-1-sulfonamide, methyl 3-[[(1R,2S)-1-[1-(4-fluorophenyl)indazol-5-yl]oxy-1-phenyl-propan-2-yl]sulfamoyl]propanoate, 1-cyclopentyl-N-[(1R,2S)-1-[1-(4-fluorophenyl)indazol-5-yl]oxy-1-phenyl-propan-2-yl]methanesulfonamide, N-[(1R,2S)-1-[1-(4-fluorophenyl)indazol-5-yl]oxy-1-phenyl-propan-2-yl]cyclopentanesulfonamide, 2,2,2-trifluoro-N-[(1R,2S)-1-[1-(4-fluorophenyl)indazol-5-yl]oxy-1-phenyl-propan-2-yl]ethanesulfonamide, 1-cyclohexyl-N-[(1R,2S)-1-[1-(4-fluorophenyl)indazol-5-yl]oxy-1-phenyl-propan-2-yl]methanesulfonamide, N-[(1R,2S)-1-[1-(4-fluorophenyl)indazol-5-yl]oxy-1-phenyl-propan-2-yl]hexane-1-sulfonamide, N-[(1R,2S)-1-[1-(4-fluorophenyl)indazol-5-yl]oxy-1-phenyl-propan-2-yl]pyridine-3-sulfonamide, N-[1-[1-(4-fluorophenyl)indazol-5-yl]oxy-2-methyl-1-phenyl-propan-2-yl]cyclopropanesulfonamide, N-[(1R,2S)-1-[1-(4-fluorophenyl)indazol-5-yl]oxy-1-(4-methylsulfanylphenyl)propan-2-yl]cyclopropanesulfonamide, N-[(1S,2S)-1-[1-(4-fluorophenyl)indazol-5-yl]oxy-1-(4-methylsulfanylphenyl)propan-2-yl]cyclopropanesulfonamide, N-[(1R,2S)-1-[1-(4-fluorophenyl)indazol-5-yl]oxy-1-(4-methylsulfanylphenyl)propan-2-yl]cyclopropanesulfonamide, N-[(1R,2S)-1-phenyl-1-(1-propan-2-ylindazol-5-yl)oxy-propan-2-yl]methanesulfonamide N-[(1R,2S)-1-[1-(4-fluorophenyl)indazol-5-yl]oxy-1-(4-methylsulfinylphenyl)propan-2-yl]cyclopropanesulfonamide, N-[(1R,2S)-1-(1-cyclopentylindazol-5-yl)oxy-1-phenyl-propan-2-yl]cyclopropanesulfonamide, N-[(1R,2S)-1-phenyl-1-(1-propan-2-ylindazol-5-yl)oxy-propan-2-yl]cyclopropanesulfonamide, N-[(1R,2S)-1-[1-(4-fluorophenyl)indazol-5-yl]oxy-1-(4-methylsulfonylphenyl)propan-2-yl]cyclopropanesulfonamide, N-[(1R,2S)-1-[6-chloro-1-(4-fluorophenyl)indazol-5-yl]oxy-1-(4-fluorophenyl)propan-2-yl]cyclopropanesulfonamide, N-[(1R,2R)-1-[6-chloro-1-(4-fluorophenyl)indazol-5-yl]oxy-1-(4-fluorophenyl)propan-2-yl]cyclopropanesulfonamide, N-[2-[1-(4-fluorophenyl)indazol-5-yl]sulfanyl-2-phenyl-ethyl]cyclopropanesulfonamide, N-[(1R,2S)-1-[1-(4-fluorophenyl)indazol-5-yl]sulfanyl-1-phenyl-propan-2-yl]methanesulfonamide, N-[(1R,2S)-1-[1-(4-fluorophenyl)indazol-5-yl]sulfonyl-1-phenyl-propan-2-yl]methanesulfonamide, N-[(2R)-2-[1-(4-fluorophenyl)indazol-5-yl]oxy-2-phenyl-ethyl]cyclopropanesulfonamide, N-[(2S)-2-[1-(4-fluorophenyl)indazol-5-yl]oxy-2-phenyl-ethyl]cyclopropanesulfonamide, N-[(1R,2S)-1-[1-(4-fluorophenyl)indazol-5-yl]oxy-1-quinolin-3-yl-propan-2-yl]cyclopropanesulfonamide, N-((1R,2S)-1-(2,3-dihydrobenzo[b][1,4]dioxin-6-yl)-1-(1-(4-fluorophenyl)-1H-indazol-5-yloxy)propan-2-yl)cyclopropanesulfonamide, Cyclopropanesulfonic acid N-{1-[6-methoxypyridin-3-yl]-1-[(1-pyridin-2-yl-1H-indazol-5-yl)oxy]propan-2-yl}amide, Cyclopropanesulfonic acid N-{1-[6-methoxypyridin-3-yl]-1-[(1-pyridin-3-yl-1H-indazol-5-yl)oxy]propan-2-yl}amide, Cyclopropanesulfonic acid N-{1-[2-methoxypyridin-4-yl]-1-[(1-pyridin-3-yl-1H-indazol-5-yl)oxy]propan-2-yl}amide, Cyclopropanesulfonic acid N-{1-[2-methoxypyridin-4-yl]-1-[(1-pyridin-2-yl-1H-indazol-5-yl)oxy]butan-2-yl}amide, 1-Methyl-1H-imidazole-4-sulfonic acid N-[(1R,2S)-1-[1-(4-fluorophenyl)indazol-5-yl]oxy-1-phenyl-propan-2-yl]amide, and 3,5-Dimethylisooxazole-4-sulfonic acid N-[(1R,2S)-1-[1-(4-fluorophenyl)indazol-5-yl]oxy-1-phenyl-propan-2-yl]amide, or a pharmaceutically acceptable salt thereof.

9. A pharmaceutical composition comprising a compound or formula (I) or a pharmaceutically acceptable salt thereof as claimed in claim 1 or claim 4, and a pharmaceutically acceptable adjuvant, diluent or carrier.

10. A method of treating an inflamatory condition, an asthmatic condition COPD, in a mammal, which comprises administering to a mammal in need of such treatment an effective amount of a compound of formula (I), or a pharmaceutically acceptable salt thereof as claimed in claim 1 or claim 4.

11. A combination of a compound of formula (I), or a pharmaceutically acceptable salt thereof, as claimed in claim 1, and one or more agents selected from the list comprising:
a PDE4 inhibitor;
a selective β.sub2. adrenoceptor agonist;
a muscarinic receptor antagonist;
a steroid;
a modulator of chemokine receptor function; or,
an inhibitor of p38 kinase function.

12. A process for the preparation of a compound of formula (I) by a) coupling a compound of formula (II):

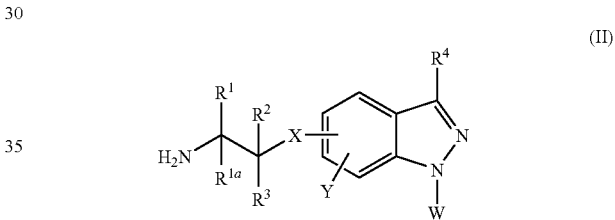

with a compound of formula (III):

wherein $L^1$ is a leaving group, in a suitable solvent, in the presence of a suitable base.

* * * * *

UNITED STATES PATENT AND TRADEMARK OFFICE
CERTIFICATE OF CORRECTION

PATENT NO. : 8,030,340 B2
APPLICATION NO. : 11/986555
DATED : October 4, 2011
INVENTOR(S) : Markus Berger et al.

Page 1 of 2

It is certified that error appears in the above-identified patent and that said Letters Patent is hereby corrected as shown below:

Title Page, Item (57) Abstract at line 3, "thereof," should read -- thereof; --.

Column 66, lines 19-20, "$R^6C(O)R^5NC_{1-4}alkyl$," should read -- $R^6C(O)R^5NC_{0-4}alkyl$, --.

Column 66, line 34, "$C_{1-4}alkylOC(O)C_{0-4}alkyl$," should read -- $C_{0-4}alkylOC(O)C_{0-4}alkyl$, --.

Column 66, line 37, after "$C_{0-4}alkylOC(O)C_{0-4}alkylNH$", insert -- $C_{0-4}alkylC(O)OC_{0-4}alkylNH$, --.

Column 66, line 47, "group(O)$C_{5-10}$", should read -- group –(O)$C_{5-10}$ --.

Column 67, line 12, "$C_{0-6}alkylOC_{1-4}$-alkyl$OC_{0-4}alkyl$," should read
-- $C_{0-6}alkylOC_{1-4}alkylOC_{0-4}alkyl$, --.

Column 67, line 13, "$C_{1-4}alkylC(O)OC_{0-4}alkyl$," should read -- $C_{0-4}alkylC(O)OC_{0-4}alkyl$, --.

Column 67, line 14, "$C_{1-4}alkylOC(O)C_{0-4}alkyl$," should read -- $C_{0-4}alkylOC(O)C_{0-4}alkyl$, --.

Column 67, line 18, "$C_{0-4}alkylC(O)OC_{0-4}alkylNH$" should read -- $C_{0-4}alkylC(O)OC_{0-4}alkylNH$, --.

Column 67, line 26, "$C_{1-4}alkylthioC_{0-4}alkyl$," should read -- $C_{0-4}alkylthioC_{0-4}alkyl$, --.

Column 67, line 33, "$C_{0-4}alkylOC(O)C_{0-4}alkylNH$" should read -- $C_{0-4}alkylOC(O)C_{0-4}alkylNH$, --.

Column 67, line 35, "R3" should read -- $R^3$ --.

Column 67, line 44, "$C_{1-4}haloalkyl$," should read -- $C_{1-6}haloalkyl$, --.

Column 67, line 51, "$C_{0-4}alkylOC(O)C_{0-4}alkylNH$" should read -- $C_{0-4}alkylOC(O)C_{0-4}alkylNH$, --.

Signed and Sealed this
Thirteenth Day of December, 2011

David J. Kappos
*Director of the United States Patent and Trademark Office*

CERTIFICATE OF CORRECTION (continued)
U.S. Pat. No. 8,030,340 B2

Column 67, line 53, after "O," insert -- S, --.

Column 68, line 4, after "R²", insert -- is --.

Column 68, line 36, "sulfonamide" should read -- sulfonamide, --.

Column 69, line 8, "methanesulfonamide", should read -- methanesulfonamide, --.

Claim 70, line 12, after "treating", delete "an inflammatory condition,".

Claim 70, line 13, after "condition", insert -- or --.

Claim 70, line 22, "β.sub2.", should read -- $β_2$ --.

UNITED STATES PATENT AND TRADEMARK OFFICE
CERTIFICATE OF CORRECTION

PATENT NO.       : 8,030,340 B2
APPLICATION NO.  : 11/986555
DATED            : October 4, 2011
INVENTOR(S)      : Markus Berger et al.

It is certified that error appears in the above-identified patent and that said Letters Patent is hereby corrected as shown below:

Title Page, Item (57) Abstract at line 3, "thereof," should read -- thereof; --.

Column 66, lines 19-20, "$R^6C(O)R^5NC_{1-4}alkyl$," should read -- $R^6C(O)R^5NC_{0-4}alkyl$, --.

Column 66, line 34, "$C_{1-4}alkylOC(O)C_{0-4}alkyl$," should read -- $C_{0-4}alkylOC(O)C_{0-4}alkyl$, --.

Column 66, line 37, after "$C_{0-4}alkylOC(O)C_{0-4}alkylNH$", insert -- $C_{0-4}alkylC(O)OC_{0-4}alkylNH$, --.

Column 66, line 47, "group(O)$C_{5-10}$", should read -- group –(O)$C_{5-10}$ --.

Column 67, line 12, "$C_{0-6}alkylOC_{1-4}$-$alkylOC_{0-4}alkyl$," should read
-- $C_{0-6}alkylOC_{1-4}alkylOC_{0-4}alkyl$, --.

Column 67, line 13, "$C_{1-4}alkylC(O)OC_{0-4}alkyl$," should read -- $C_{0-4}alkylC(O)OC_{0-4}alkyl$, --.

Column 67, line 14, "$C_{1-4}alkylOC(O)C_{0-4}alkyl$," should read -- $C_{0-4}alkylOC(O)C_{0-4}alkyl$, --.

Column 67, line 18, "$C_{0-4}alkylC(O)OC_{0-4}alkylNH$" should read -- $C_{0-4}alkylC(O)OC_{0-4}alkylNH$, --.

Column 67, line 26, "$C_{1-4}alkylthioC_{0-4}alkyl$," should read -- $C_{0-4}alkylthioC_{0-4}alkyl$, --.

Column 67, line 33, "$C_{0-4}alkylOC(O)C_{0-4}alkylNH$" should read -- $C_{0-4}alkylOC(O)C_{0-4}alkylNH$, --.

Column 67, line 35, "R3" should read -- $R^3$ --.

This certificate supersedes the Certificate of Correction issued December 13, 2011.

Signed and Sealed this
Tenth Day of January, 2012

David J. Kappos
*Director of the United States Patent and Trademark Office*

CERTIFICATE OF CORRECTION (continued)
U.S. Pat. No. 8,030,340 B2

Column 67, line 44, "$C_{1-4}$haloalkyl," should read -- $C_{1-6}$haloalkyl, --.

Column 67, line 51, "$C_{0-4}$alkylOC(O)$C_{0-4}$alkylNH" should read -- $C_{0-4}$alkylOC(O)$C_{0-4}$alkylNH, --.

Column 67, line 53, after "O," insert -- S, --.

Column 68, line 4, after "$R^2$", insert -- is --.

Column 68, line 36, "sulfonamide" should read -- sulfonamide, --.

Column 69, line 8, "methanesulfonamide", should read -- methanesulfonamide, --.

Column 70, line 12, (claim 10, line 1) after "treating", delete "an inflammatory condition,".

Column 70, line 13, (claim 10, line 2) after "condition", insert -- or --.

Column 70, line 22, (claim 11, line 5) "β.sub2.", should read -- $β_2$ --.